US012599580B2

(12) United States Patent
Hustvedt et al.

(10) Patent No.: US 12,599,580 B2
(45) Date of Patent: Apr. 14, 2026

(54) COMPOSITION COMPRISING A LIPID COMPOUND, A TRIGLYCERIDE, AND A SURFACTANT, AND METHODS OF USING THE SAME

(71) Applicant: BASF AS, Olso (NO)

(72) Inventors: Svein Olaf Hustvedt, Olso (NO); Preben Houlberg Olesen, København NV (DK); Annette Müllertz, Charlottenlund (DK)

(73) Assignee: BASF AS, Oslo (NO)

( * ) Notice: Subject to any disclaimer, the term of this patent is extended or adjusted under 35 U.S.C. 154(b) by 746 days.

(21) Appl. No.: 17/737,761

(22) Filed: May 5, 2022

(65) Prior Publication Data

US 2023/0090432 A1 Mar. 23, 2023

Related U.S. Application Data

(62) Division of application No. 14/770,862, filed as application No. PCT/IB2014/000823 on Feb. 28, 2014, now Pat. No. 11,351,139.

(60) Provisional application No. 61/770,646, filed on Feb. 28, 2013.

(51) Int. Cl.

| | |
|---|---|
| ***A61K 31/202*** | (2006.01) |
| ***A61K 9/00*** | (2006.01) |
| ***A61K 9/107*** | (2006.01) |
| ***A61K 9/48*** | (2006.01) |
| ***A61K 31/20*** | (2006.01) |
| ***A61K 47/10*** | (2017.01) |
| ***A61K 47/14*** | (2017.01) |
| ***A61K 47/26*** | (2006.01) |

(52) U.S. Cl.

CPC .......... *A61K 31/202* (2013.01); *A61K 9/0053* (2013.01); *A61K 9/107* (2013.01); *A61K 9/48* (2013.01); *A61K 31/20* (2013.01); *A61K 47/10* (2013.01); *A61K 47/14* (2013.01); *A61K 47/26* (2013.01)

(58) Field of Classification Search

CPC .................................................... A61K 31/202

See application file for complete search history.

(56) References Cited

U.S. PATENT DOCUMENTS

| | | | |
|---|---|---|---|
| 2,909,554 | A | 10/1959 | Doerr |
| 4,009,211 | A | 2/1977 | Onopchenko et al. |
| 4,032,564 | A | 6/1977 | Henrick et al. |
| 4,040,781 | A | 8/1977 | Lamberti et al. |
| 4,209,410 | A | 6/1980 | Baldwin |
| 4,214,088 | A | 7/1980 | Abeler et al. |
| 4,286,053 | A | 8/1981 | Ishikawa et al. |
| 4,297,268 | A | 10/1981 | Abeler et al. |
| 4,368,190 | A | 1/1983 | Shen et al. |
| 4,411,808 | A | 10/1983 | Gutierrez et al. |
| 4,444,766 | A | 4/1984 | Bosies et al. |
| 4,652,441 | A | 3/1987 | Okada et al. |
| 5,306,754 | A | 4/1994 | Yamamoto et al. |
| 5,328,953 | A | 7/1994 | Lynch |
| 5,445,832 | A | 8/1995 | Orsolini et al. |
| 5,447,820 | A | 9/1995 | Hayakawa et al. |
| 5,523,430 | A | 6/1996 | Patel et al. |
| 5,612,093 | A | 3/1997 | Braig et al. |
| 5,763,517 | A | 6/1998 | Yamamoto et al. |
| 5,770,584 | A | 6/1998 | Kucera |
| 5,990,173 | A | 11/1999 | Patoiseau et al. |
| 6,060,515 | A | 5/2000 | Elias et al. |
| 6,087,353 | A | 7/2000 | Stewart |
| 6,284,268 | B1 | 9/2001 | Mishra |
| 6,365,628 | B1 | 4/2002 | Berge |
| 6,376,688 | B1 | 4/2002 | Ferrante et al. |
| 6,511,670 | B1 | 1/2003 | Maignan et al. |
| 6,624,190 | B2 | 9/2003 | Khoury et al. |
| 6,723,717 | B1 | 4/2004 | Youngquist et al. |
| 6,835,750 | B1 | 12/2004 | Henderson |
| 7,250,456 | B2 | 7/2007 | Eigen et al. |
| 7,273,852 | B2 | 9/2007 | Tsuji et al. |
| 7,427,583 | B2 | 9/2008 | Couillet et al. |
| 7,517,858 | B1 | 4/2009 | Hostetler et al. |
| 7,902,399 | B2 | 3/2011 | Berge et al. |
| 7,968,617 | B2 | 6/2011 | Thalacker et al. |
| 8,173,831 | B2 | 5/2012 | Milne et al. |
| 8,304,551 | B2 | 11/2012 | Milne et al. |
| 8,735,436 | B2 | 5/2014 | Hovland et al. |
| 8,741,966 | B2 | 6/2014 | Holmeide |

(Continued)

FOREIGN PATENT DOCUMENTS

| | | | |
|---|---|---|---|
| CA | 2115345 | | 2/1993 |
| CA | 2667211 | A1 | 5/2008 |

(Continued)

OTHER PUBLICATIONS

Ahmad, J. et al., "Reactions in Monolayers: Base-Catalyzed Ester Hydrolysis Revisited," Langmuir (1990) 6:1797-1799.

Anby, M. et al., "Lipid Digestion as a Trigger for Supersaturation: Evaluation of the Impact of Supersaturation Stabilization on the in Vitro and in Vivo Performance of Self-Emulsifying Drug Delivery Systems," Molecular Pharmaceutics, 2012; 9(7): 2063-2079.

Bach et al. (The American Journal of Clinical Nutrition 36: Nov. 1982, pp. 950-962).

(Continued)

*Primary Examiner* — Rei Tsang Shiao

(74) *Attorney, Agent, or Firm* — Finnegan, Henderson, Farabow, Garrett & Dunner, LLP

(57) ABSTRACT

Compositions comprising 2-((5Z,8Z,11Z,14Z,17Z)-icosa-5,8,11,14,17-pentaenyloxy)butanoic acid, an ester derivative, or a pharmaceutically acceptable salt thereof; a triglyceride; and a surfactant, as well as methods for their use. The present disclosure further relates to self-emulsifying drug delivery systems, such as SEDDS, SMEDDS, or SNEDDS comprising 2-((5Z,8Z,11Z,14Z,17Z)-icosa-5,8,11,14,17-pentaenyloxy)butanoic acid.

20 Claims, 50 Drawing Sheets

(56) References Cited

U.S. PATENT DOCUMENTS

| | | | |
|---|---|---|---|
| 8,759,558 | B2 | 6/2014 | Holmeide et al. |
| 8,946,190 | B2 | 2/2015 | Gagnon |
| 9,394,228 | B2 | 7/2016 | Hovland et al. |
| 2002/0156124 | A1 | 10/2002 | Gao |
| 2003/0147814 | A1 | 8/2003 | Scherrer et al. |
| 2004/0126424 | A1 | 7/2004 | Jandacek et al. |
| 2005/0107503 | A1 | 5/2005 | Couillet et al. |
| 2006/0135785 | A1 | 6/2006 | Patoiseau et al. |
| 2006/0247458 | A1 | 11/2006 | Yamamoto et al. |
| 2006/0251685 | A1 | 11/2006 | Yu |
| 2007/0060497 | A1 | 3/2007 | Krahmer et al. |
| 2007/0088170 | A1 | 4/2007 | Bryhn et al. |
| 2007/0167529 | A1 | 7/2007 | Walton et al. |
| 2007/0254026 | A1 | 11/2007 | Stewart |
| 2007/0254862 | A1 | 11/2007 | Antel et al. |
| 2008/0124387 | A1 | 5/2008 | Spilburg |
| 2008/0317844 | A1 | 12/2008 | Dudley |
| 2009/0137567 | A1 | 5/2009 | Perrine et al. |
| 2010/0267828 | A1 | 10/2010 | Holmeide et al. |
| 2010/0280109 | A1 | 11/2010 | Holmeide |
| 2011/0054029 | A1 | 3/2011 | Kuhrts |
| 2011/0190395 | A1 | 8/2011 | Holmeide et al. |
| 2012/0122940 | A1 | 5/2012 | Hovland et al. |
| 2012/0252850 | A1 | 10/2012 | Milne et al. |
| 2012/0264791 | A1 | 10/2012 | Milne et al. |
| 2013/0046013 | A1 | 2/2013 | Hovland et al. |
| 2013/0345269 | A1 | 12/2013 | Hovland et al. |
| 2014/0221439 | A1 | 8/2014 | Hovland et al. |
| 2014/0316002 | A1 | 10/2014 | Holmeide et al. |
| 2016/0206585 | A1 | 7/2016 | Hustvedt et al. |

FOREIGN PATENT DOCUMENTS

| | | | |
|---|---|---|---|
| CA | 2667150 | A1 | 11/2008 |
| CN | 1248916 | A | 3/2000 |
| CN | 101213281 | A | 7/2008 |
| CN | 101225064 | | 7/2008 |
| CN | 1024241422 | A | 4/2012 |
| CN | 102459142 | A | 5/2012 |
| CN | 101213281 | B | 3/2013 |
| EP | 0 002 007 | | 5/1979 |
| EP | 0 050 327 | | 4/1982 |
| EP | 0 052 510 | A3 | 5/1982 |
| EP | 0 175 591 | | 3/1986 |
| EP | 0 346 879 | A1 | 12/1989 |
| EP | 0 399 183 | | 11/1990 |
| EP | 0 463 947 | | 1/1992 |
| EP | 2 248 798 | | 11/2010 |
| ES | 2 009 346 | | 9/1989 |
| GB | 1038723 | | 8/1966 |
| GB | 1 393 805 | | 5/1975 |
| GB | 1523276 | A | 8/1978 |
| GB | 2 209 937 | A | 6/1989 |
| JP | 48-039001 | B | 11/1973 |
| JP | 04-051149 | | 2/1992 |
| JP | 11-180929 | | 7/1999 |
| JP | 2000-344 736 | A | 12/2000 |
| JP | 2003-527364 | T | 9/2003 |
| JP | 2009-520797 | A | 5/2009 |
| JP | 2014-505017 | A | 2/2014 |
| TW | 201233388 | A | 8/2012 |
| WO | WO 96/11908 | A | 4/1996 |
| WO | WO 1997 /38688 | | 10/1997 |
| WO | WO 98/032444 | | 7/1998 |
| WO | WO 1999/16804 | | 4/1999 |
| WO | WO 00/072920 | | 12/2000 |
| WO | WO 01/68582 | | 9/2001 |
| WO | WO 01/098328 | | 12/2001 |
| WO | WO 03/014073 | | 2/2003 |
| WO | WO 03/063878 | | 8/2003 |
| WO | WO 2005/073164 | | 8/2005 |
| WO | WO 2006/025246 | | 3/2006 |
| WO | WO 2006/094915 | | 9/2006 |
| WO | WO 2006/117664 | A1 | 11/2006 |
| WO | WO 2006/117668 | A1 | 11/2006 |
| WO | WO 2007/072061 | A2 | 6/2007 |
| WO | WO 2007 /116027 | | 10/2007 |
| WO | WO 2008/053331 | | 5/2008 |
| WO | WO 2008/053340 | | 5/2008 |
| WO | WO 2008/125241 | | 10/2008 |
| WO | WO 2009/056983 | | 5/2009 |
| WO | WO 2009/061208 | | 5/2009 |
| WO | WO 2009/149496 | | 12/2009 |
| WO | WO 2009/156621 | | 12/2009 |
| WO | WO 2010/006085 | | 1/2010 |
| WO | WO 2010/008299 | | 1/2010 |
| WO | WO 2010/103402 | A1 | 9/2010 |
| WO | WO 2010/103404 | A1 | 9/2010 |
| WO | WO 2010/128401 | * | 11/2010 |
| WO | WO 2010/128401 | A1 | 11/2010 |
| WO | WO 2011 /089529 | | 7/2011 |
| WO | WO 2012/032415 | A2 | 3/2012 |
| WO | WO 2012/059818 | A1 | 5/2012 |
| WO | WO 2012/115695 | | 8/2012 |
| WO | WO 2013/016531 | | 1/2013 |

OTHER PUBLICATIONS

Berge et al., "Metabolic effects ofthia fatty acids." Current Opinion in Lipidology. (2002) 13(3): 295-304.

Berge, S.M et al., "Pharmaceutical Salts," J. Pharmaceutical Sciences (1977) 66(1):1-19.

Brain, E.G et al., "Derivatives of 6-Aminopenicillanic Acid. Part II." Trisubstituted Acetyl Derivatives, J. Chemical Society (1962) 1445-1453.

Burness, D.M. "Decarboxylation of Thietin Salts," J. Organic Chemistry, (1959) 24(6):849-852.

Buyukozturk, F. et al., "Impact of emulsion-based drug delivery systems on intestinal permeability and drug release kinetics," Journal of Controlled Release, 201 O; 142: 22-30.

Cao, G. Selected topics of pharmaceutical chemistry. China Medical Science Press, 1993. pp. 123-125.

Chen, et al. Basic Drug Design, 1st Edition, Huazhong University of Science and Technology (HUST) Press, 1995, pp. 162-169.

Derzhinskii, A.R. et al., "Functional Sulfur-Containing Compounds. Part 4. Preparation of Chloro(Bromo) Alkyl Sulfones by Oxidative Halogenation of Hydroxyalkyl Sulfides and Sulfoxides with Mixtures of Hydrogen Peroxide and a Hydrohalic Acid," IzvestiyaAkademii Nauk SSSR Seriya Khimicheskaya (1982) 31(5):995-1001.

English language abstract for CN 101225064.

English language abstract for CN 102421422.

English language abstract for CN 102459142.

English language abstract for EP O 463 947.

English language abstract for JP 04-051149.

English language abstract of ES 2 009 346, Sep. 16, 1989.

English language translation of Microcarrier Drug Delivery System, Huazhong University of Science and Technology Press, (ed. Cheng Fang), copyright 2009, pp. 217-219 (8 pages).

English machine translation of JP 11-180929.

English translation of JP 48-039001 B.

English translation, Cao, G. Selected topics of pharmaceutical chemistry. China Medical Science Press, 1993. pp. 123-125.

English translation, Chen, et al. Basic Drug Design, 1st Edition (Huazhong University of Science and Technology (HUST) Press, 1995), p. 162-169.

English Translation, Silverman, R.B., The Organic Chemistry of Drug Design and Drug Action, 2nd Edition, 19-20, (Chemical Industry Press, 2008).

Ferrell, W.J., "Synthesis and Properties of 35S, 14C and 3H Labeled S-Alkyl Glycerol Ethers and Derivatives," Chemistry and Physics of Lipids (1976) 16:276-284.

Ferrucci, L. et al., "Relationship of Plasma Polyunsaturated Fatty Acids to Circulating Inflammatory Markers," J. Clin. Endocrin. & Metab. (2006) 91 (2):439-446.

Flock et al., "Syntheses of Some Polyunsaturated Sulfur- and Oxygen-Containing Fatty Acids Related to Eicosapentaenoic and Docosahexaenoic Acids," Acta Chemica Scandinavica (1999) 53:436-445.

(56) References Cited

OTHER PUBLICATIONS

Geleijnse, J.M. et al., "Blood Pressure Response to Fish Oil Supplementation: Metaregression Analysis of Randomized Trials," J. Hypertension (2002) 20(8):1493-1499.
Goldsworthy, L.J. et al., "Some Sulphides Containing the 2-Chloroethyl Group," Journal of the Chemical Society (1948) 2177-2179.
Granlund, L. et al., "Effects of Structural Changes of Fatty Acids on Lipid Accumulation in Adipocytes and Primary Hepatocytes," Biochemica et Biophysica Acta (2005) 1687:23-30.
Grupp, I.L. et al., "Protection Against Hypoxia-Reoxygenation in the Absence of Poly (ADP-Ribose) Synthetase in Isolated Working Hearts," J. Mol. Cell Cardiol. (1999) 31 :297-303.
Heckmann, B. et al., "Grignard Additions to a,!3-Unsaturated Dioxolanones: Preparation of Chiral Allylic Alcohols and Protected a-Hydroxy Aldehydes," Tetrahedron Letters (1996) 37:1421-1424.
Hermetter, A. & Pal Tauf, F., "A Facile Procedure for the Synthesis of Saturated Phosphatidylcholines," Chemistry & Physics of Lipids (1981) 28: 111-115.
Hernandez, V. A et al., "Thiazolidinediones and Risk of Heart Failure in Patients with or at High Risk or Type 2 Diabetes Mellitus," Am J Cardiovasc Drugs 2011; 11 (2) pp. 115-128.
Hill, A.J. & Fager, E.W., "Some a-Alkylthio Aliphatic Acids," Journal of the American Chemical Society (1943) 65(12):2300-2301.
Holmeide, A.K. & Skattenbol, L., "Syntheses of Some Polyunsaturated Trifluoromethyl Ketones as Potential Phospholipase A2 Inhibitors," J. Chem. Soc., Perkin Trans. (2000) 1 :2271-2276.
Hosokawa, M. et al., "Preparation of Therapeutic Phospholipids Through Porcine Pancreatic Phospholipase A2-Mediated Esterification and Lipozyme-Mediated Acidolysis," J. Am. Oil Chem. Soc. (1995) 72(11):1287-1291.
International Search Report for International Application No. PCT/IB2010/001251, dated Oct. 4, 2010.
International Search Report for International Application No. PCT/IB2011/000250, dated May 31, 2011.
International Search Report for International Application No. PCT/IB2011/002925, dated Mar. 5, 2012.
International Search Report for International Application No. PCT/NO2008/000391, dated Feb. 4, 2009.
International Search Report for International Application No. PCT/NO2009/000262, dated Oct. 23, 2009.
International Search Report of International Application No. PCT/IB2014/000823, Jul. 17, 2014.
Jones, P.B. et al., "A New Class of Antituberculosis Agents," J. Med. Chem. (2003) 43: 3304-3314.
Kameyama, E. et al., "Alkylcarboxymethyl Sulphoxides," American Chemical Society Chemical Abstracts (1971) 7 4(23):401.
Kasai, Y. et al., "Synthesis of Diphenylalkane Sulfonate and Its Surface Activity," Yes Kogyo Kagaku Zasshi (1965) 68(11):2073-2077.
Lamango, N.S. et al., "Inhibition Mechanism of S-Adenosylmethionine-Induced Movement Deficits by Prenylcysteine Analogs," Pharmacology, Biochemistry, & Behavior (2003) 43:433-442.
Larsen et al., "a- and Is- Alkyl-Substituted Eicosapentaenoic Acids: Incorporation into Phospholipids and Effects on Prostaglandin H Synthase and 5-Lipoxygenase," Biochemical Pharmacology (1998) 55:405-11.
Larsen, L.N. et al., "Polyunsaturated Thia- and Oxa-Fatty Acids: Incorporation into Cell-Lipids and Their Effects on Arachidonic Acid- and Eicosanoid Syntheses," Biochemica et Biophysica Acta (1997) 1348:346-354.
Larsen, L.N. et al., "Sulfur Substituted and a-Methylated Fatty Acids as Peroxisome Proliferator-Activated Receptor Activators," Lipids (2005) 40:49-57.
Lilja-Hallberg, M. & Harrod, M., "Enzymatic Esterification of Long Polyunsaturated Fatty Acids and Lyso-Phosphatidylcholine in Isooctane and Ethanol," Biocatalysis (1994) 9:195-207.
Livingston, J.R. & Drogin, R., "The Synthesis and Some Surface Active Properties of Alkylthioalkyl and Alkoxyalkyl Sulfates," The Journal of the American Oil Chemists' Society (1965) 42:720-723.
Manallack DT et al., "The significance of acid/base properties in drug discovery," *Chem Soc Rev.* 2013; 42(2): 485-496, PMC Author's Manuscript. (23 pages).
Masson, M. et al., "Marine Lipids for Prodrugs, Soft Compounds and Other Pharmaceutical Applications," Pharmazie (2000) 55(3):172-177.
Matsumoto, M. et al., Orally Administered Eicosapentaenoic Acid Reduces and Stabilizes Atherosclerotic Lesions in ApoE-Deficient Mice, Atherosclerosis (2008) 197:524-533.
Meyer, K.L. et al., "In Vivo Evaluation of Phosphocholine and Quaternary Ammonium Containing Lipids as Novel Anti-HIV Agents," J. Med. Chem. (1991) 34(4): 1377-1383.
Microcarrier Drug Delivery System, Huazhong University of Science and Technology Press, (ed. Cheng Fang), copyright 2009, pp. 217-219 (5 pages).
MIGLYOL® 812 and MIGLYOL® 810 product descriptions, http://www.petercremerna.com/products/159339301, accessed Jun. 4, 2019. (3 pages).
Müllertz A et al., "New perspectives on lipid and surfactant based drug delivery systems for oral delivery of poorly soluble drugs," *J Pharm Pharmacol.* 2010, 62(11): 1622-1636 (15 pages).
Notice of Allowance in U.S. Appl. No. 12/741,890, issued Jan. 17, 2014.
Notice of Allowance in U.S. Appl. No. 13/054,212, issued Jan. 29, 2014.
Notice of Allowance in U.S. Appl. No. 13/319,101, issued Jan. 13, 2014.
Notice of Allowance in U.S. Appl. No. 13/883,405, issued Mar. 14, 2016.
Notice of Allowance in U.S. Appl. No. 14/770,086 issued Feb. 8, 2022.
Notice of Allowance in U.S. Appl. No. 14/770,086 issued Mar. 9, 2022.
Nystrom, R.F. & Brown, W.G., "Reduction of Organic Compounds by Lithium Aluminum Hydride. II. Carboxylic Acids," Journal of the American Chemical Society (1947) 69(10):2548-2549.
Office Action (Restriction Requirement) for U.S. Appl. No. 13/574,132 dated Jan. 20, 2015.
Office Action dated Apr. 1, 2013, from U.S. Appl. No. 13/054,212.
Office Action dated Apr. 24, 2013, from U.S. Appl. No. 13/319,101.
Office Action dated Aug. 3, 2012, from U.S. Appl. No. 12/741,890.
Office Action dated Aug. 6, 2013, from U.S. Appl. No. 12/741,890.
Office Action dated Dec. 10, 2012, from U.S. Appl. No. 12/741,890.
Office Action dated Jan. 28, 2015, from U.S. Appl. No. 13/883,405.
Office Action dated Jan. 31, 2013, from U.S. Appl. No. 13/319,101.
Office Action dated Jul. 1, 2013, from U.S. Appl. No. 13/054,212.
Office Action dated Jul. 17, 2014, from U.S. Appl. No. 13/883,405.
Office Action for U.S. Appl. No. 14/263,793 dated Aug. 11, 2015.
Office Action from U.S. Appl. No. 13/319,101, dated Oct. 2, 2013.
Office Action (Restriction Requirement) from U.S. Appl. No. 14/770,862, dated Aug. 18, 2016.
Office Action from U.S. Appl. No. 14/770,862, dated Feb. 10, 2017.
Office Action from U.S. Appl. No. 14/770,862, dated Nov. 14, 2017.
Office Action from U.S. Appl. No. 14/770,862, dated Dec. 14, 2018.
Office Action from U.S. Appl. No. 14/770,862, dated Nov. 15, 2019.
Okoronkwo, A.E. et al., "Synthesis of w-Hydroxy-a-Alkyl/Aryl-y-Organo-Selenium and y-Organo-Tellurium: A New Class of Organochalcogen Compounds with Antinociceptive Activity," Tetrahedron Letters (2008) 49:3252-3256.
Parkkari, T. et al., "a-Methylated Derivatives of 2-Arachidonoyl Glycerol: Synthesis, CB1 Receptor Activity, and Enzymatic Stability," Bioorg. & Med. Chem. Lett. (2006) 16:2437-2440.
Patent Trial and Appeal Board Decision from U.S. Appl. No. 14/770,862 issued Oct. 18, 2021.
Pitt, M.J. et al., "Synthesis of Polyunsaturated is-Oxa Fatty Acids Via Rhodium Mediated Carbenoid Insertion," Synthesis (1997) 7:1240-42.
Registry Copyright 2008 ACS on STN (RN 785712-42-7, 714185-72-5, 45247-37-8).
Ringbom, T. et al., "COX-2 Inhibitory Effects of Naturally Occurring and Modified Fatty Acids," J. Nat. Prod. (2001) 64:745-749.

(56) References Cited

OTHER PUBLICATIONS

Rossmeisl, Martin et al., Prevention and Reversal o Obesity and Glucose Intolerance in Mice by DHA Derivatives, OBesity, vol. 17, No. 5, pp. 1023-1031 (2009).
Shchepin, R. et al., "Quorum Sensing in Candida albicans: Probing Farnesol's Mode of Action with 40 Natural and Synthetic Farnesol Analogs," (2003) Chemistry & Biology 10:7 43-750.
Shirley, D.A. et al., "Alkylation with Long Chain p-Toluenesulfonates. IV. Alkylation of Alcohols and Amines with n-Octadecyl p-Toluenesulfonate," Journal of Organic Chemistry (1953) 18:378-381.
Silverman, R.B., The Organic Chemistry of Drug Design and Drug Action, (Academic Press 1992), pp. 4, 14-28.
Silverman, R.B., The Organic Chemistry of Drug Design and Drug Action, 2nd Yes Edition, 19-20, (Chemical Industry Press, 2008) (Chinese).
Simopoulos, A.P., "Essential Fatty Acids in Health and Chronic Disease," Am. J. Clin. Nutr. (1999) 70(Suppl):560S-569S.
Srisiri, W. et al., "Syntheses of Polymerizable Monoacylglycerols and 1,2-Diacylsn-Glycerols," J. Org. Chem. (1996) 61 (16):5911-5915.
Stahl, P.H. & Wermuth, C.G., "Chapter 12: Monographs on Acids and Bases," at 265-327, in "Handbook of Pharmaceutical Salts: Properties, Selection, and Use."
Storlien, L.H. et al., "Polyunsaturated Fatty Acids, Membrane Function and Metabolic Diseases Such as Diabetes and Obesity," Curr. Opin. Clin. Nutr. & Metab. Care (1998) 1 (6):559-563.
Supplementary European Search Report for European Patent Application No. 11 83 7647, dated Feb. 13, 2014.
Togashi, N. et al., "Antibacterial Activity of Long-Chain Fatty Alcohols Against Staphylococcus aureus," Molecules (2007) 12: 139-148.
Tran, P.O.T. et al., "Inhibition of Interleukin-1 is-Induced COX-2 and EP3 Gene Expression by Sodium Salicylate Enhances Pancreatic Islet is-Cell Function," Diabetes (2002) 51: 1772-78.
Tsotinis, A. et al., "Synthesis and Antiretroviral Evaluation of New Alkoxy and Aryloxy Phosphate Derivatives of 3'-Azido-3' Deoxythymidine," J. Med Chem (1996) 39:3418-3422.
Udding, J. et al., "Xanthate Transfer Cyclization of Glycolic Acid-Derived Radicals. Synthesis of Five-to Eight-Membered Ring Ethers," J. Org. Chem. (1994) 59:6671-6682.
U.S. Appl. No. 62/84268 B1 filed by Awadhesh Mirshra, dated Sep. 2001.
Vaagenes, H. et al., "Methylated Eicosapentaenoic Acid and Tetradecylathioacetic Acid: Effects on Fatty Acid Metabolism," Biochem. Pharmacol. (1999) 58:1133-1143._D.
Wang, P. et al., "Synthesis of Phospholipid-Inhibitor Conjugates by Enzymatic Transphosphatidylation with Phospholipase D," J. Am. Chem. Soc. (1993) 115:10487-10491.
Weizmann, C. et al., "The Synthesis of a-Alkoxyisobutyric Acids and Alkyl Methacrylates from Acetonechloroform," J. Am. Chem. Soc. (1948) 70:1153-1158.
Willumsen, N. et al., "Enhanced Hepatic Fatty Acid Oxidation and Upregulated Carnitine Palmitoyltransferase II Gene Expression by Methyl 3-Thiaoctadeca-6, 9, 12, 15-Tetraenoate in Rats," J. Lipid Mediators Cell Signaling (1997) 17:115-134.
Willumsen, N. et al., "On the Effect of 2-Deuterium- and 2-Methyl-Eicosapentaenoic Acid Derivatives on Triglyerides, Peroxisomal is-Oxidation and Platelet Aggregation in Rats," Biochimica et Biophysica Acta (1998) 1369: 193-203.
Woodbury, D.M. & Fingle, E., "Drugs Effective in the Therapy of the Epilepsies," Basis of Therapeutics 201-26 (5th Ed. 1975).
Zeinalov, B.K., "Synthesis and Investigation of Esters of Alkyl Selenium Ethanols," Azerbajdzanskij Chimiceskij Zurnal (1981) 5:41-43.

* cited by examiner

Particle Size Distribution for Composition No. 2 in Water

Particle Size Distribution for Composition No. 4 in Water

Particle Size Distribution for Composition No. 5 in Water

Particle Size Distribution for Composition No. 6 in Water

Particle Size Distribution for Composition No. 9 in Intestinal Media

Particle Size Distribution for Composition No. 17 in Intestinal Media

Particle Size Distribution for Composition No. 18 in Intestinal Media

Particle Size Distribution for Composition No. 23 in Gastric Media

Particle Size Distribution for Composition No. 22 in Intestinal Media

Particle Size Distribution for Composition No. 23 in Intestinal Media

Particle Size Distribution for Composition No. 27 in Intestinal Media

Particle Size Distribution for Composition No. 38 in Gastric Media

Particle Size Distribution for Composition No. 38 in Intestinal Media

Particle Size Distribution for Composition No. 73 in Milli-Q Water

Particle Size Distribution for Composition No. 74 in Milli-Q Water

Particle Size Distribution for Composition No. 75 in Milli-Q Water

Particle Size Distribution for Composition No. 77 in Milli-Q Water

Emulsions Formed for Sample Nos. 73-77 (Vials 9, 10, 11, 14, 15, Respectively)

Particle Size Distribution for Composition No. 63 in Milli-Q Water

Particle Size Distribution for Composition No. 64 in Milli-Q Water

Particle Size Distribution for Composition No. 66 in Milli-Q Water

Particle Size Distribution for Composition No. 69 in Milli-Q Water

Particle Size Distribution for Composition No. 72 in Milli-Q Water

COMPOSITION COMPRISING A LIPID COMPOUND, A TRIGLYCERIDE, AND A SURFACTANT, AND METHODS OF USING THE SAME

This is a divisional application of U.S. application Ser. No. 14/770,862, filed Aug. 27, 2015, now U.S. Pat. No. 11,351,139, which is a national stage filing under 35 U.S.C. § 371 of International Application No. PCT/IB2014/000823, filed on Feb. 28, 2014, which claims priority to U.S. Provisional Application No. 61/770,646, filed on Feb. 28, 2013, all of which are incorporated herein by reference in their entireties.

TECHNICAL FIELD

The present disclosure relates generally to compositions comprising 2-((5Z,8Z,11Z,14Z,17Z)-icosa-5,8,11,14,17-pentaenyloxy)butanoic acid, an ester derivative, or a pharmaceutically acceptable salt thereof; a triglyceride; and a surfactant; as well as methods for their use. More particularly, the present disclosure relates to compositions comprising 2-((5Z,8Z,11Z,14Z,17Z)-icosa-5,8,11,14,17-pentaenyloxy)butanoic acid; a triglyceride; and a surfactant; as well as methods for their use. The present disclosure further relates to self-microemulsifying drug delivery systems (SMEDDS), self-nanoemulsifying drug delivery system (SNEDDS), or self-emulsifying drug delivery system (SEDDS) comprising 2-((5Z,8Z,11Z,14Z,17Z)-icosa-5,8,11,14,17-pentaenyloxy)butanoic acid, an ester derivative, or a pharmaceutically acceptable salt thereof; a triglyceride; and a surfactant.

BACKGROUND

Long-chain omega-3 fatty acids, such as EPA and DHA, are well established in the treatment of hypertriglyceridemia (HTG) and have beneficial effects upon other risk factors associated with chronic heart disease, such as hypertension and a prothrombotic state. Omega-3 fatty acids, such as EPA and DHA, may also regulate immune functions, insulin action, neuronal development, and visual function. Further, omega-3 fatty acids are generally well-tolerated, without giving rise to severe side effects. However, due to their limited biological effects upon other cardiovascular risk factors, such as lowering LDL-cholesterol, there is a need to develop new omega-3 fatty acid derivatives with improved biological effects. Rossmeisl and coworkers have studied the biological effects of omega-3 fatty acid derivatives, such as alpha-substituted EPA and DHA derivatives. See Rossmeisl et al. (Obesity (2009) 17: 1023-1031).

International Patent Application Publication No. WO 2010/128401 discloses that 2-((5Z,8Z,11Z,14Z,17Z)-icosa-5,8,11,14,17-pentaenyloxy)butanoic acid favorably influences lipid profiles and inhibits the development of atherosclerosis in the APOE*3Leiden.CETP transgenic mouse model. Specifically, 2-((5Z,8Z,11Z,14Z,17Z)-icosa-5,8,11,14,17-pentaenyloxy)butanoic acid decreased total cholesterol and increased HDL cholesterol as compared to a control. It also decreased atherosclerotic lesion areas in the aorta as compared to a control. Those results demonstrate that 2-((5Z,8Z,11Z,14Z,17Z)-icosa-5,8,11,14,17-pentaenyloxy)butanoic acid and its derivatives may be useful in the prevention or treatment of various conditions, such as inflammation, hyperlipidemic conditions, obesity, fatty liver disease, atherosclerosis, peripheral insulin resistance, and/or diabetic conditions. Reference is made to pages 54-58 of WO 2010/128401 and pages 14-16 of WO2012/059818 describing the biological testing of 2-((5Z,8Z,11Z,14Z,17Z)-icosa-5,8,11,14,17-pentaenyloxy)butanoic acid and the corresponding Figures mentioned therein.

To be effective in such prevention or treatment regimes, the active ingredient, 2-((5Z,8Z,11Z,14Z,17Z)-icosa-5,8,11,14,17-pentaenyloxy)butanoic acid, an ester derivative, or a pharmaceutically acceptable salt thereof must reach its biological target. Evidence suggests, however, that such targeting is complicated by enzymes that interconvert long chain fatty acids and alcohols in vivo. Moreover, the carboxylic acid functional group of fatty acid molecules targets cellular binding, but this ionizable group may hinder the molecule from crossing the cell membranes, such as that of the intestinal wall. As a result, carboxylic acid functional groups are often protected as esters, which are then hydrolyzed by plasma enzymes. This process may not occur quickly enough in the blood and may predominantly occur in the liver, keeping the active ingredient from reaching its cellular target.

Ideally, a formulation will assist or support the active pharmaceutical ingredient (API) in reaching its target organ, in this case the liver, and also will improve the bioavailability of the API by increasing the portal vein uptake and improve the pharmacokinetics properties leading to enhanced benefit-risk properties of the API due to lower systemic exposure and thus reduced risk of systemic adverse events.

Documents such as WO 2010/103402 and US 2011/0054029 disclose fatty acid compositions comprising surfactants but do not specifically disclose 2-((5Z,8Z,11Z,14Z,17Z)-icosa-5,8,11,14,17-pentaenyloxy)butanoic acid. Even though both documents describe formulations stated to improve bioavailability of omega-3 fatty acids, such as EPA and DHA, no teaching is given with respect to formulations improving the pharmacokinetic properties, such as lack of gender differences, low individual variability or dose proportional exposure. Nor do the above mentioned patent applications address the problem of achieving food independent bioavailability of the active ingredients.

Thus, there remains a need for compositions comprising 2-((5Z,8Z,11Z,14Z,17Z)-icosa-5,8,11,14,17-pentaenyloxy)butanoic acid, an ester derivative, or a pharmaceutically acceptable salt thereof that improve or enhance solubilization, digestion, bioavailability, and/or absorption in vivo, while maintaining the ability for 2-((5Z,8Z,11Z,14Z,17Z)-icosa-5,8,11,14,17-pentaenyloxy)butanoic acid, an ester derivative, or a pharmaceutically acceptable salt thereof to cross cell membranes and reach its biological targets. Furthermore, there remains a need for a composition that has improved pharmacokinetics properties, such as lack of gender differences, low individual variability or dose proportional exposure, and does not exhibit food effects, of 2-((5Z,8Z,11Z,14Z,17Z)-icosa-5,8,11,14,17-pentaenyloxy)butanoic acid, an ester derivative, or a pharmaceutically acceptable salt thereof, in a desirably fashion.

DESCRIPTION

The present disclosure relates to compositions comprising 2-((5Z,8Z,11Z,14Z,17Z)-icosa-5,8,11,14,17-pentaenyloxy)butanoic acid, an ester derivative, or a pharmaceutically acceptable salt thereof; a triglyceride; and a surfactant. In one embodiment, the present disclosure relates to a composition comprising from 5% to 60% by weight of the total composition of 2-((5Z,8Z,11Z,14Z,17Z)-icosa-5,8,11,14,17-pentaenyloxy)butanoic acid, an ester derivative, or a pharmaceutically acceptable salt thereof; from 15% to 60% by weight of the total composition of a medium-chain triglyceride (MCT) oil; and from 10% to 60% by weight of the total composition of a nonionic surfactant. In one embodiment the present disclosure relates to compositions comprising 2-((5Z,8Z,11Z,14Z,17Z)-icosa-5,8,11,14,17-pentaenyloxy)butanoic acid, a $C_1$-$C_6$-alkyl or phenyl ester derivative, or a pharmaceutically acceptable salt thereof; a triglyceride chosen from medium-chain triglyceride (MCT) oils or long-chain triglyceride (LCT) oils; and a nonionic surfactant. More particularly, the present disclosure relates to compositions comprising 2-((5Z,8Z,11Z,14Z,17Z)-icosa-5,8,11,14,17-pentaenyloxy)butanoic acid; a triglyceride; and a surfactant. More particularly, the present disclosure relates to compositions comprising 2-((5Z,8Z,11Z,14Z,17Z)-icosa-5,8,11,14,17-pentaenyloxy)butanoic acid; a triglyceride chosen from MCT oils or LCT oils; and a nonionic surfactant. The present disclosure further relates to such a composition, which is a self-microemulsifying drug delivery system (SMEDDS) and forms micro emulsions in contact with aqueous media. Furthermore, the present disclosure relates to such a composition, which is a self-nanoemulsifying drug delivery system (SNEDDS) and forms nanoemulsions in contact with aqueous media.

It has surprisingly been shown that the compositions or preconcentrates of the present disclosure will increase the concentration of the compounds according to the present disclosure in the micellar phase by more than 50%, compared to a standard oil formulation. Thus, these SMEDDS increase the rate and extent of amount active pharmaceutical ingredient (API) available for absorption in an in-vivo situation.

The compositions presently disclosed may be administered orally, for example in capsule or tablet form, to a subject for the treatment, prevention, or regulation of at least one condition including, for example, activation or modulation of at least one of the human peroxisome proliferator-activated receptor (PPAR) isoforms α, γ or δ, wherein said composition acts as a pan-agonist or modulator; for the prevention and/or treatment of a dyslipidemic condition, for example hypertriglyceridemia (HTG), dyslipidemia, and mixed dyslipidemia; the prevention and/or treatment of elevated triglyceride levels, non-HDL cholesterol levels, LDL cholesterol levels, and/or VLDL cholesterol levels; the increase of HDL cholesterol; the treatment and/or the prevention of obesity or an overweight condition; the reduction of body weight and/or for preventing body weight gain; the treatment and/or the prevention of a fatty liver disease, such as for example non-alcoholic fatty liver disease (NAFLD); the treatment and/or the prevention of an inflammatory disease or condition; the treatment and/or the prevention of atherosclerosis; the treatment and/or the prevention of peripheral insulin resistance and/or a diabetic condition; the treatment and/or prevention of type 2 diabetes; the reduction of plasma insulin, blood glucose and/or serum triglycerides, and/or any combination thereof.

It is to be understood that both the foregoing general description and the following detailed description are exemplary and explanatory only and are not restrictive of the present disclosure, as claimed.

DETAILED DESCRIPTION

Figure 1:
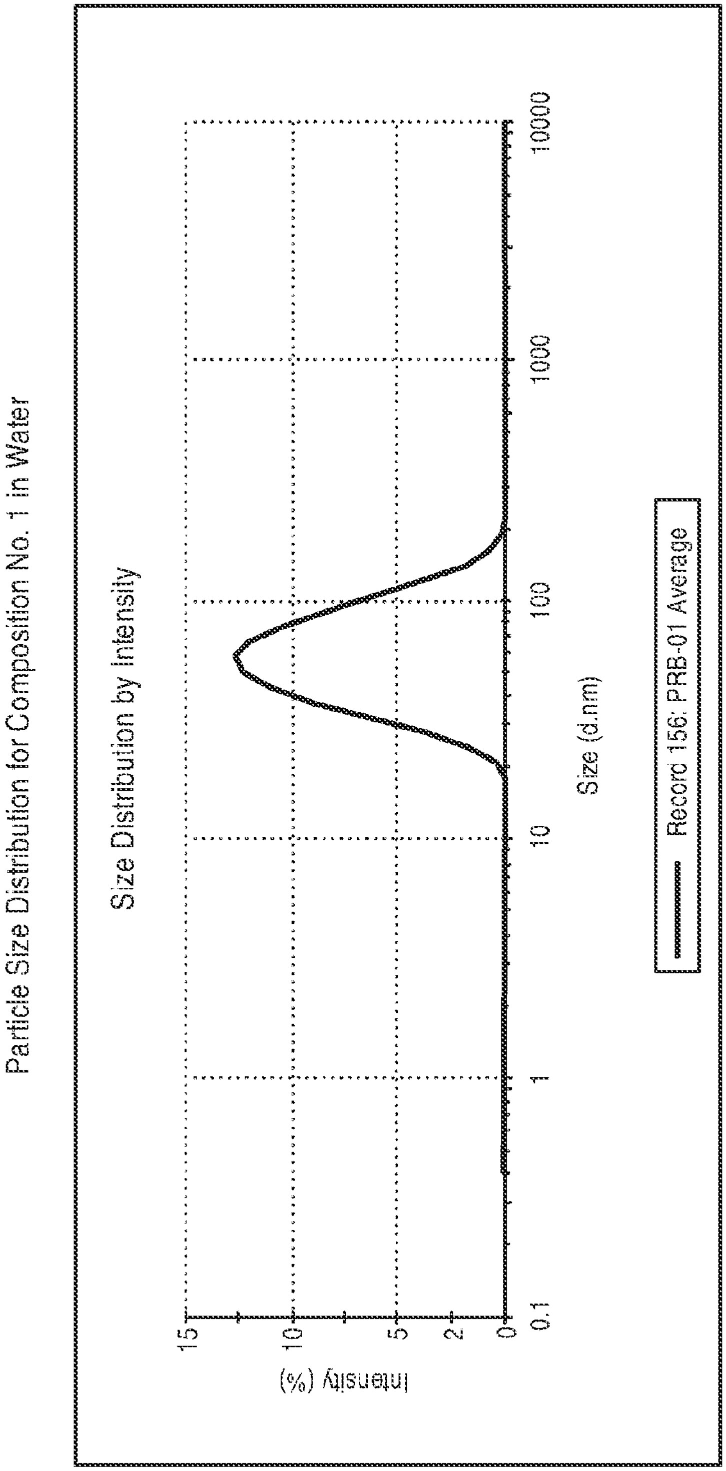
FIG. 1 shows particle size distributions for Composition Nos. 1-8.
Figure 1:
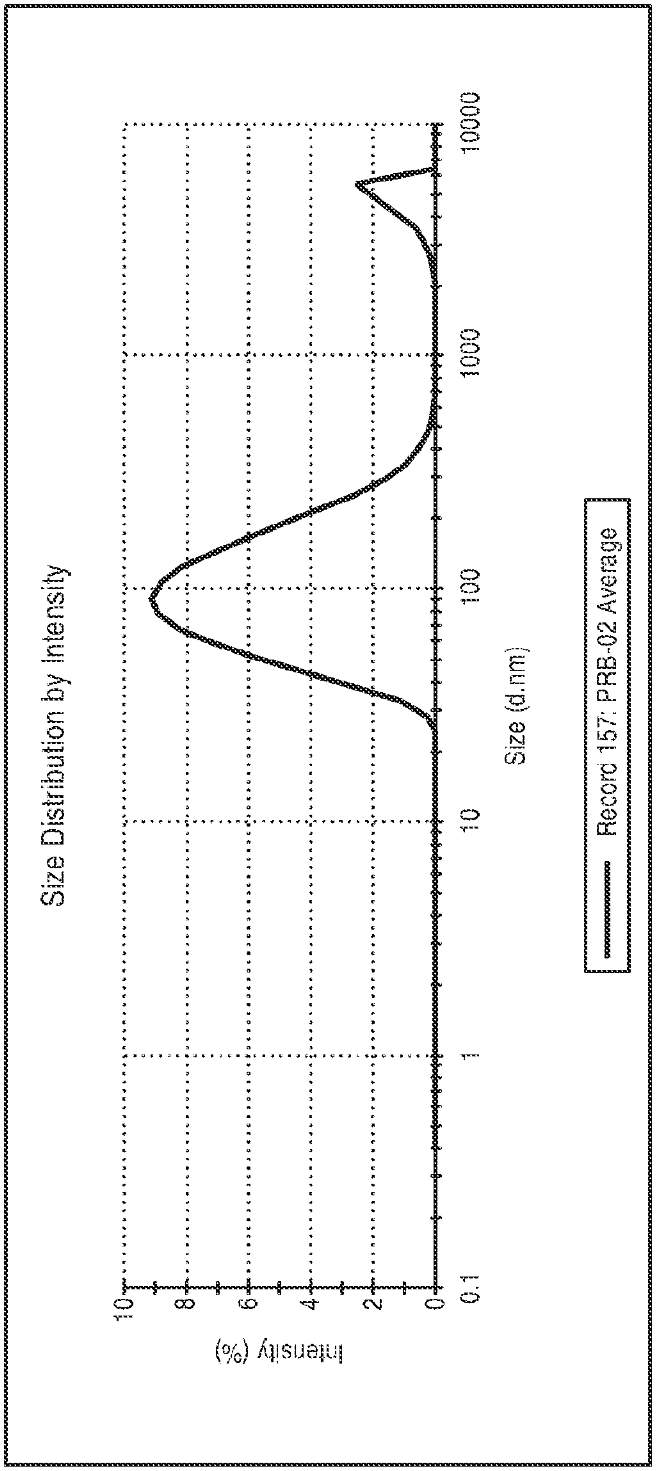
Figure 1:
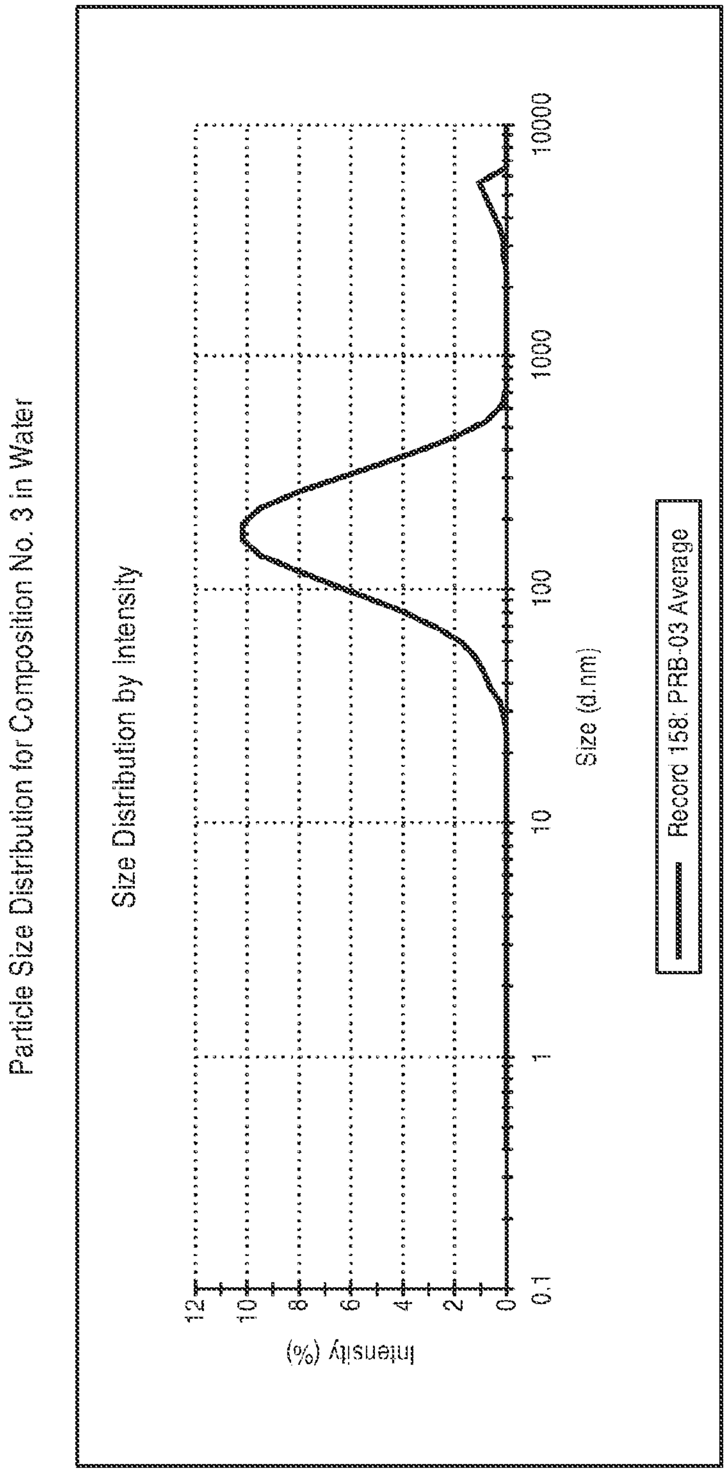
Figure 1:
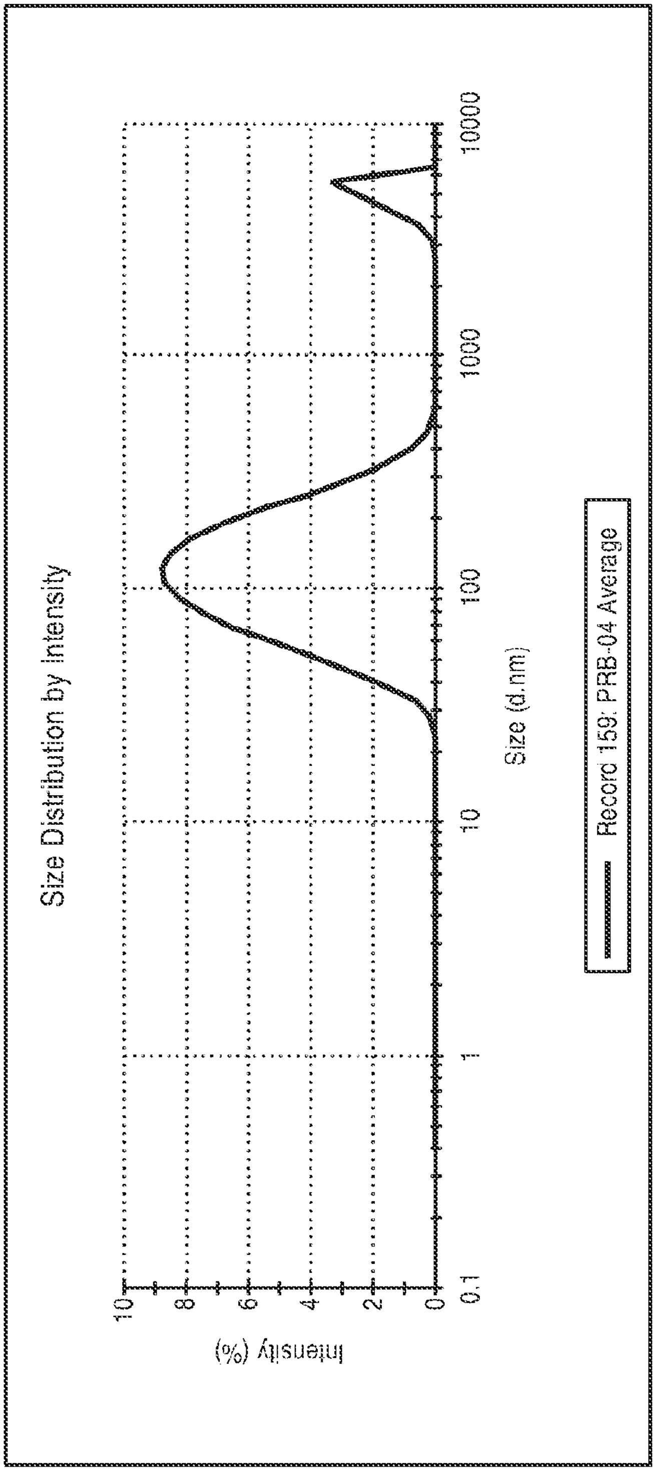
Figure 1:
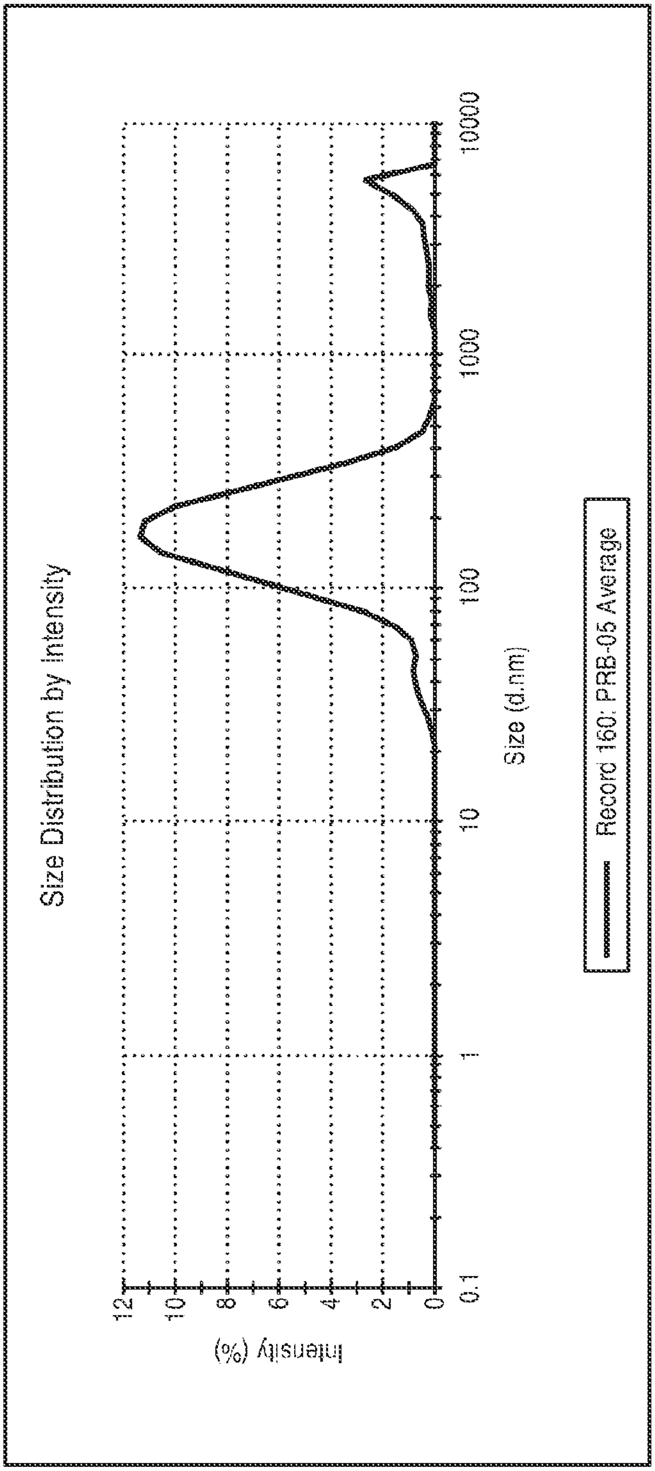
Figure 1:
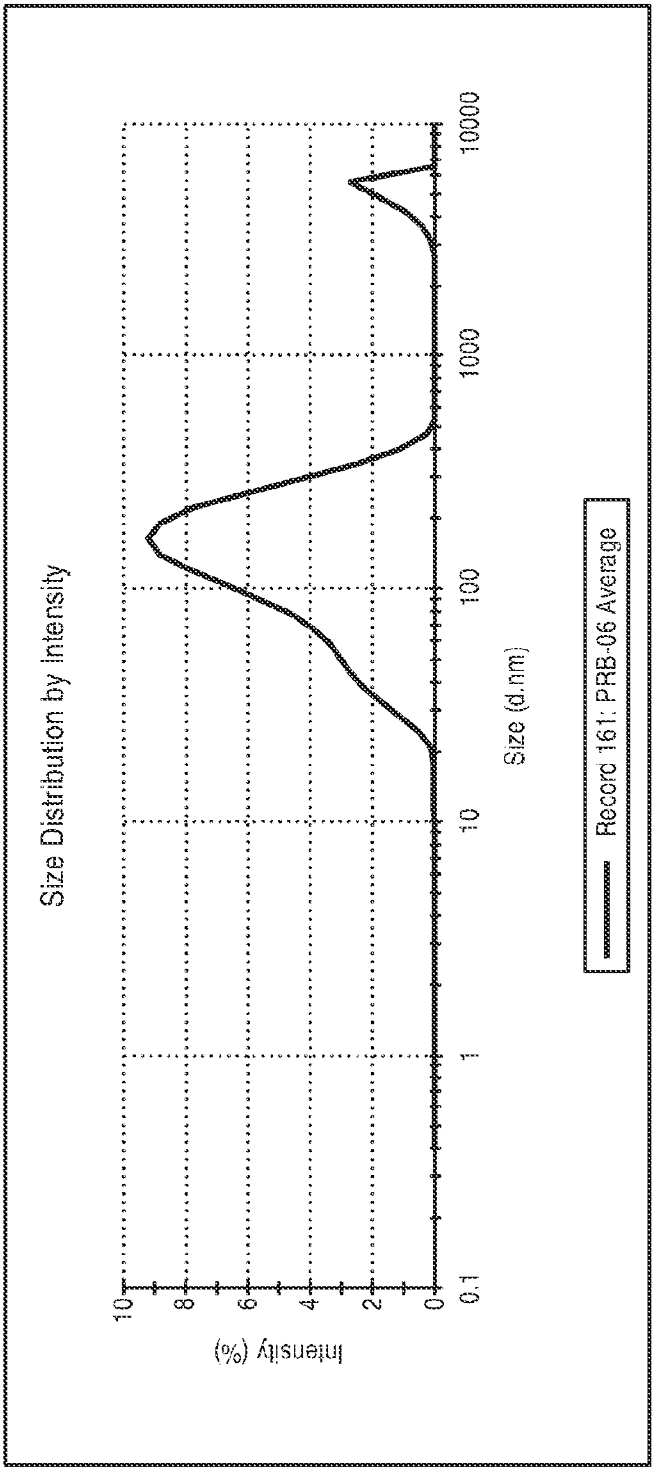
Figure 1:
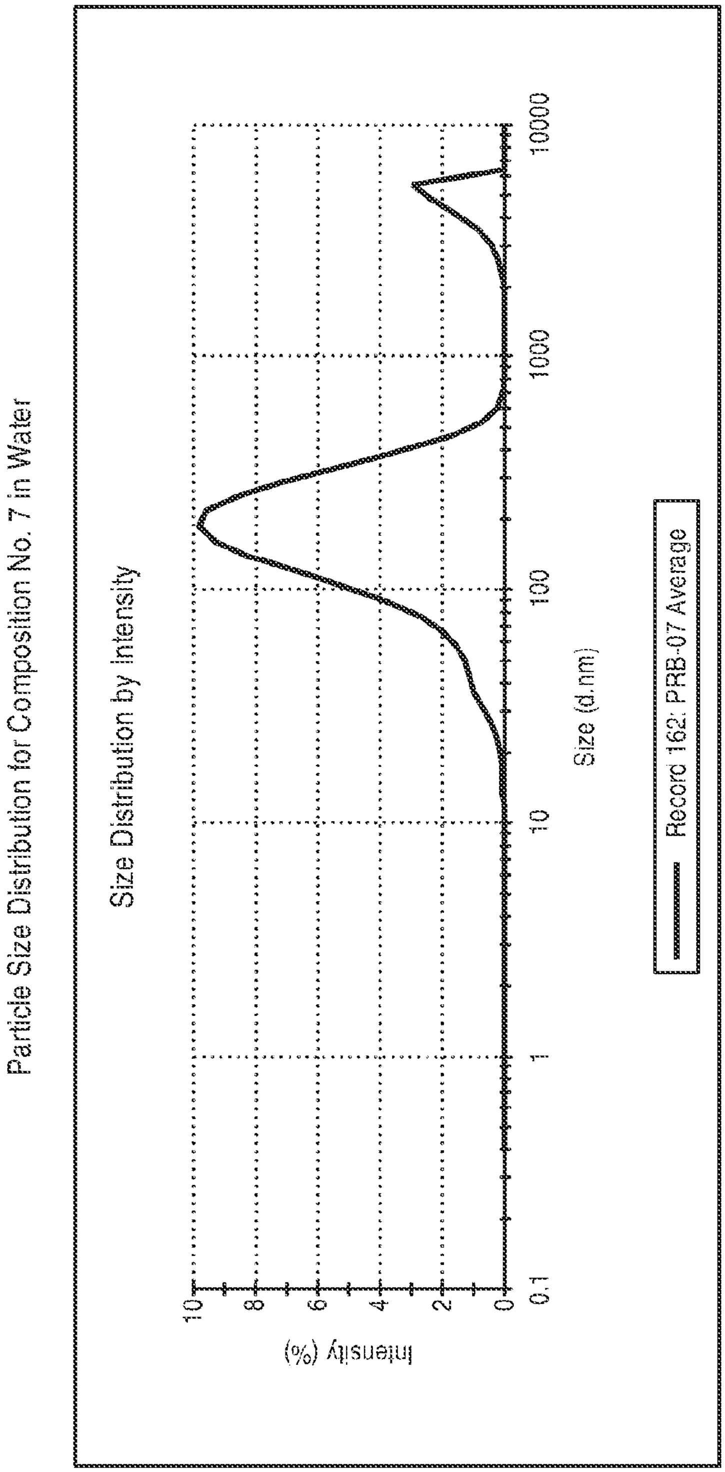
Figure 1:
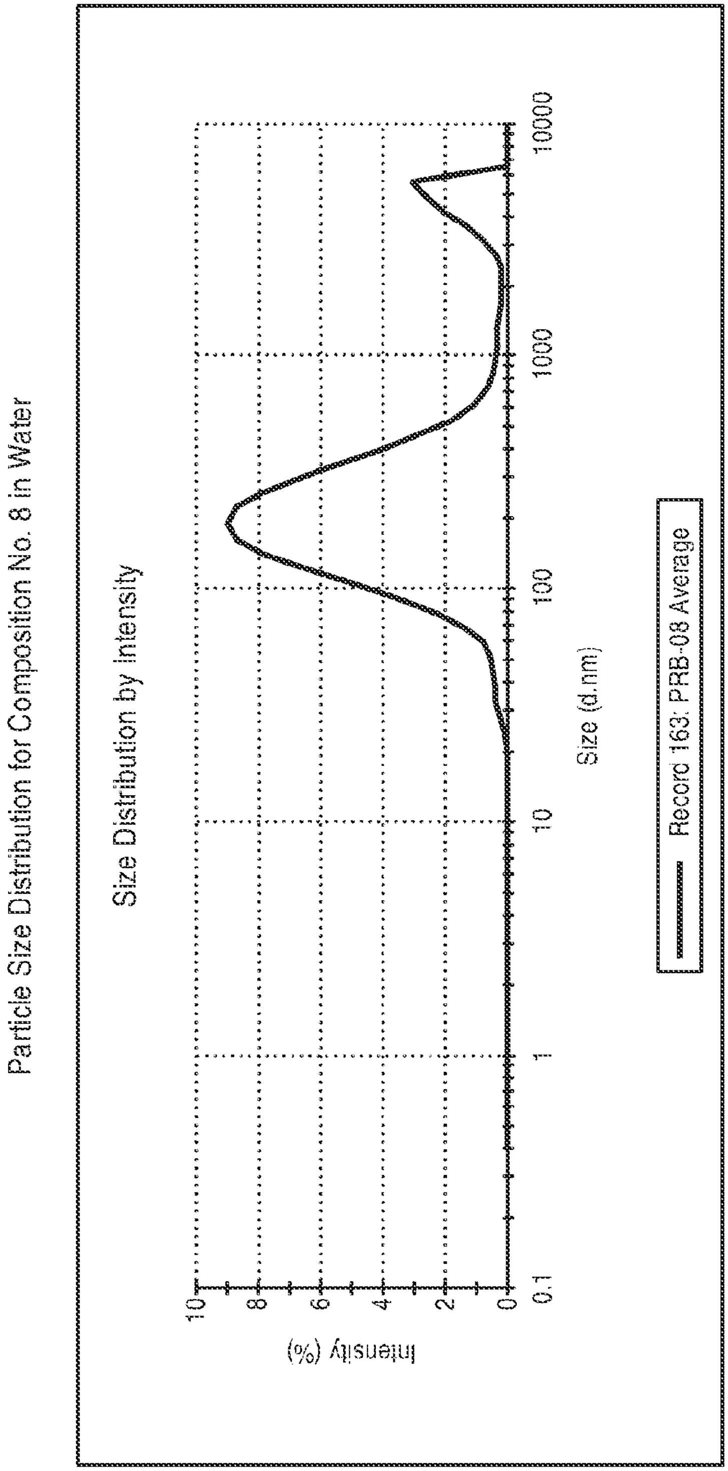

Particular aspects of the disclosure are described in greater detail below. The terms and definitions as used in the present application and as clarified herein are intended to represent the meaning within the present disclosure.

The singular forms "a," "an," and "the" include plural reference unless the context dictates otherwise.

The terms "approximately" and "about" mean nearly the same as a referenced number or value. As used herein, the terms "approximately" and "about" should be generally understood to encompass ±10% of a specified amount, frequency, or value.

The terms "treat," "treating," and "treatment" include any therapeutic application that can benefit a human or non-human mammal. Both human and veterinary treatments are within the scope of the present disclosure. Treatment may be responsive to an existing condition or it may be prophylactic, that is, preventative.

The terms "administer," "administration," or "administering" as used herein refer to (1) providing, giving, dosing, and/or prescribing by either a health practitioner or under his direction a composition according to the disclosure, and (2) putting into, taking, or consuming by the patient or person himself or herself, a composition according to the disclosure.

2-((5Z,8Z,11Z,14Z,17Z)-Icosa-5,8,11,14,17-pentaenyloxy)butanoic acid, an ester derivative, or a pharmaceutically acceptable salt thereof may exist in various stereoisomeric forms, including its enantiomers. In one embodiment, the present disclosure provides for all optical isomers of 2-((5Z,8Z,11Z,14Z,17Z)-icosa-5,8,11,14,17-pentaenyloxy) butanoic acid and mixtures thereof.

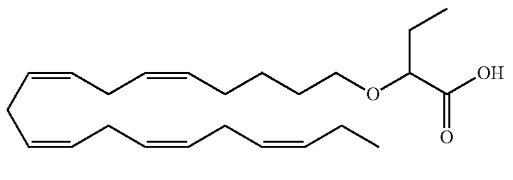 [SMILES: CC/C=C\C/C=C\C/C=C\C/C=C\C/C=C\CCCCOC(CC)C(=O)O]

2-((5Z,8Z,11Z,14Z,17Z)-icosa-5,8,11,14,17-pentaenyloxy)butanoic acid

In another embodiment, the compound of the present disclosure is (S)-2-((5Z,8Z,11Z,14Z,17Z)-icosa-5,8,11,14, 17-pentaenyloxy)butanoic acid, an ester derivative, or a pharmaceutically acceptable salt thereof. In still another embodiment the compound of the present disclosure is (S)-2-((5Z,8Z,11Z,14Z,17Z)-icosa-5,8,11,14,17-pentaenyloxy)butanoic acid.

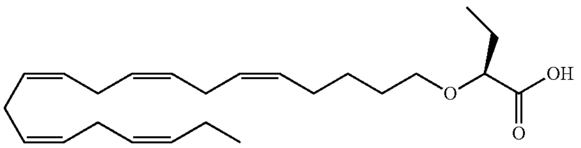 [SMILES: CC/C=C\C/C=C\C/C=C\C/C=C\C/C=C\CCCCO[C@@H](CC)C(=O)O]

(S)-2-((5Z,8Z,11Z,14Z,17Z)-icosa-5,8,11,14,17-pentaenyloxy)butanoic acid

In yet another embodiment, the compound of the present disclosure is (R)-2-((5Z,8Z,11Z,14Z,17Z)-icosa-5,8,11,14,17-pentaenyloxy)butanoic acid, an ester derivative, or a pharmaceutically acceptable salt thereof. In still another embodiment the compound of the present disclosure is (R)-2-((5Z,8Z,11Z,14Z,17Z)-icosa-5,8,11,14,17-pentaenyloxy)butanoic acid.

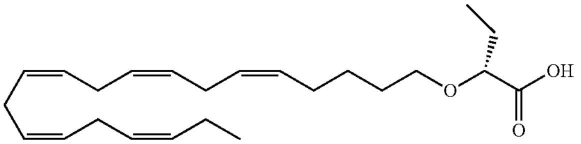 [SMILES: CC/C=C\C/C=C\C/C=C\C/C=C\C/C=C\CCCCO[C@H](CC)C(=O)O]

(R)-2-((5Z,8Z,11Z,14Z,17Z)-icosa-5,8,11,14,17-pentaenyloxy)butanoic acid

In at least one embodiment, 2-((5Z,8Z,11Z,14Z,17Z)-icosa-5,8,11,14,17-pentaenyloxy)butanoic acid is present as an ester derivative, such as for example as a $C_1$-$C_6$-alkyl ester wherein the alkyl chain may be linear or branched.

In at least one embodiment, 2-((5Z,8Z,11Z,14Z,17Z)-icosa-5,8,11,14,17-pentaenyloxy)butanoic acid is present as an ester derivative, such as for example as a methyl, ethyl, or phenyl ester derivative.

In at least one embodiment, the composition of the present disclosure comprises ethyl 2-((5Z,8Z,11Z,14Z,17Z)-icosa-5,8,11,14,17-pentaenyloxy)butanoate

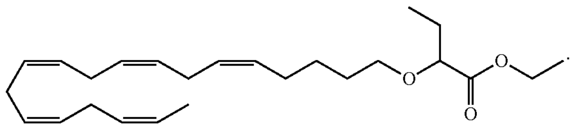 [SMILES: C/C=C\C/C=C\C/C=C\C/C=C\C/C=C\CCCCOC(CC)C(=O)OCC]

In at least one embodiment, the composition of the present disclosure comprises methyl 2-((5Z,8Z,11Z,14Z,17Z)-icosa-5,8,11,14,17-pentaenyloxy)butanoate.

In at least one embodiment, the composition of the present disclosure comprises phenyl 2-((5Z,8Z,11Z,14Z,17Z)-icosa-5,8,11,14,17-pentaenyloxy)butanoate.

In one embodiment, the present disclosure provides for a composition comprising 2-((5Z,8Z,11Z,14Z,17Z)-icosa-5,8,11,14,17-pentaen-1-yloxy)butanoic acid, an ester derivative, or a pharmaceutically acceptable salt thereof; a triglyceride; and a surfactant.

In at least one embodiment, 2-((5Z,8Z,11Z,14Z,17Z)-icosa-5,8,11,14,17-pentaenyloxy)butanoic acid, an ester derivative, or a pharmaceutically acceptable salt thereof is present in racemic form or any ratio of (R)- and (S)-enantiomers.

In embodiments, where 2-((5Z,8Z,11Z,14Z,17Z)-icosa-5,8,11,14,17-pentaenyloxy)butanoic acid is present as a salt, having a counter-ion with at least one stereogenic center, or the ester of an alcohol with at least one stereogenic center, the compound may have multiple stereocenters. In those situations, the compounds of the present disclosure may exist as diastereomers. Thus, in at least one embodiment, the compound of the present disclosure may be present as at least one diastereomer.

2-((5Z,8Z,11Z,14Z,17Z)-Icosa-5,8,11,14,17-pentaenyloxy)butanoic acid can be prepared as described, for example, in International Patent Application Publication No. WO 2010/128401. 2-((5Z,8Z,11Z,14Z,17Z)-Icosa-5,8,11,14,17-pentaenyloxy)butanoic acid may be in the form of a pharmaceutically acceptable salt or ester. For example, 2-((5Z,8Z,11Z,14Z,17Z)-icosa-5,8,11,14,17-pentaenyloxy) butanoic acid may be in the form of an ester, such as a phospholipid, a triglyceride, a 1,2-diglyceride, a 1,3-diglyceride, a 1-monoglyceride, or a 2-monoglyceride. Additional esters may include, but are not limited to, ethyl, methyl, propyl, butyl, and phenyl esters, and mixtures thereof. In one embodiment 2-((5Z,8Z,11Z,14Z,17Z)-icosa-5,8,11,14,17-pentaenyloxy)butanoic acid may be in the form of a methyl, ethyl, propyl or n-butyl ester.

Salts suitable for the present disclosure include, but are not limited to, salts of $NH_4^+$; metal ions such as $Li^+$, $Na^+$, $K^+$, $Mg^{2+}$, or $Ca^{2+}$; a protonated primary amine, such as tert-butyl ammonium, (3S,5S,7S)-adamantan-1-ammonium, 1,3-dihydroxy-2-(hydroxymethyl)propan-2-ammonium; a protonated aminopyridine, such as pyridine-2-ammonium; a protonated secondary amine, such as diethylammonium, 2,3,4,5,6-pentahydroxy-N-methylhexan-1-ammonium, N-ethylnaphthalen-1-ammonium; a protonated tertiary amine such as 4-methylmorpholin-4-ium; and a protonated guanidine such as amino((4-amino-4-carboxybutyl)amino) methaniminium or a protonated heterocycle, such as 1H-imidazol-3-ium. Additional examples of suitable salts include quaternized ions of meglumine, tris(hydroxymethyl) aminomethane, arginine, ethylenediamine, piperazine, and salts of a diprotonated diamine such as ethane-1,2-diammonium$^{2+}$ or piperazine-1,4-diium$^{2+}$. Other salts according to the present disclosure may comprise protonated Chitosan:

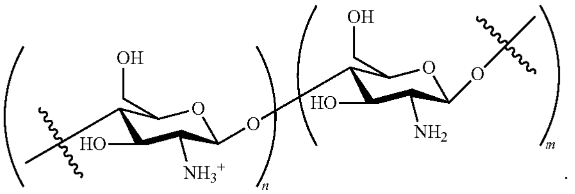

In at least one embodiment of the present disclosure compositions comprise a pharmaceutically effective amount of 2-((5Z,8Z,11Z,14Z,17Z)-icosa-5,8,11,14,17-pentaenyloxy)butanoic acid and a pharmaceutically acceptable salt thereof, wherein the salt is a monovalent salt; a triglyceride; and a surfactant. In one embodiment of the present disclosure, the salt is sodium 2-((5Z,8Z,11Z,14Z,17Z)-icosa-5,8,11,14,17-pentaenyloxy)butanoate

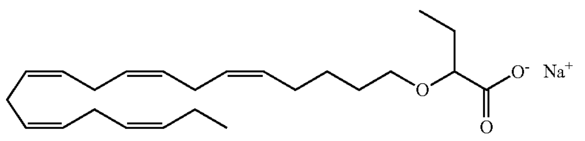 [SMILES: CC/C=C\C/C=C\C/C=C\C/C=C\C/C=C\CCCCOC(CC)C(=O)[O-] ; [Na+]]

In at least one embodiment of the present disclosure compositions comprise a pharmaceutically effective amount of 2-((5Z,8Z,11Z,14Z,17Z)-icosa-5,8,11,14,17-pentaenyloxy)butanoic acid and a pharmaceutically acceptable salt thereof, wherein the salt is a divalent salt; a triglyceride; and a surfactant. In one embodiment of the present disclosure, the salt is magnesium 2-((5Z,8Z,11Z,14Z,17Z)-icosa-5,8,11,14,17-pentaenyloxy)butanoate

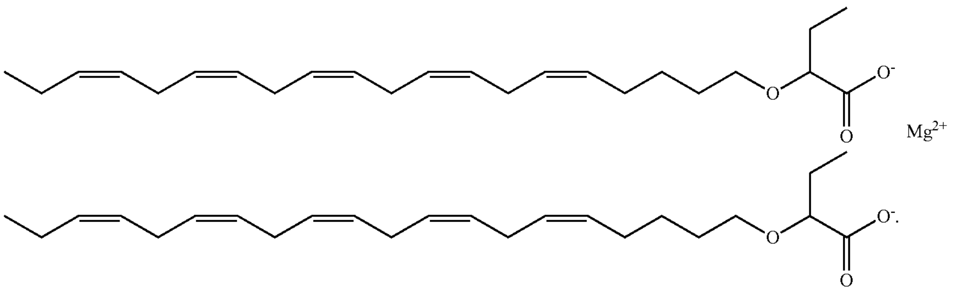

In at least one embodiment of the present disclosure, the salt is calcium 2-((5Z,8Z,11Z,14Z,17Z)-icosa-5,8,11,14,17-pentaenyloxy)butanoate

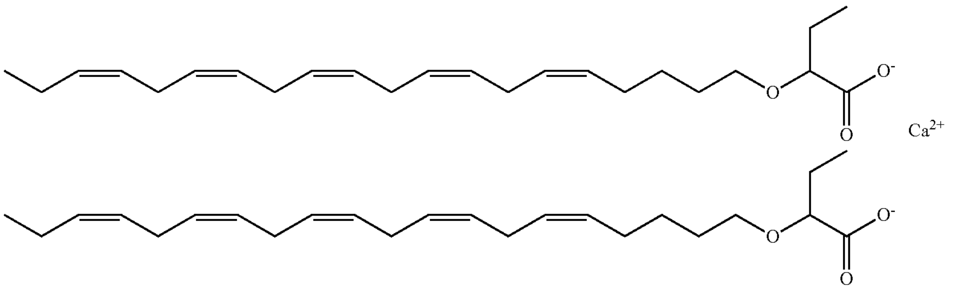

As used herein, the term "pharmaceutically-effective amount" means an amount sufficient to treat, for example, reduce and/or alleviate the effects and/or symptoms of at least one health problem in a subject in need thereof.

The term "pharmaceutical composition" means a compound according to the present disclosure in any form suitable for medical use.

The compositions presently disclosed may further comprise at least one non-active pharmaceutical ingredient, such as for example additional excipients. Such excipients may solubilize, suspend, thicken, dilute, emulsify, stabilize, preserve, protect, color, flavor, and/or fashion active ingredients into an applicable and efficacious preparation, such that it may be safe, convenient, and/or otherwise acceptable for use. In at least one embodiment the non-active pharmaceutical ingredient may be chosen from colloidal silicon dioxide, crospovidone, lactose monohydrate, lecithin, microcrystalline cellulose, polyvinyl alcohol, povidone, sodium lauryl sulfate, sodium stearyl fumarate, talc, titanium dioxide, and xanthum gum.

The composition presently disclosed may further comprise an antioxidant. Examples of antioxidants suitable for the present disclosure include, but are not limited to, α-tocopherol (vitamin E), calcium disodium EDTA, alpha tocopheryl acetates, butylhydroxytoluenes (BHT), and butylhydroxyanisoles (BHA).

The compositions presently disclosed may be administered orally. For oral administration, the compositions may be in the forms of capsules, tablets, beads, or in another forms suitable for oral administration, such as for example liquid loaded tables (LLT). In one embodiment the beads are present in form of a sachet. In one embodiment such capsules, beads or tablets may optionally be coated with a gastroresistant coating. In at least one embodiment of the present disclosure, the composition is in the form of a gelatin capsule. Such gelatin capsules can be made from type-A gelatin, type-B gelatin, and any combinations thereof, manufactured from the collagen of animal skin and bone, for example from sources such as fish, pigs, or cattle. In at least one embodiment gelatin capsules may be selected from both hard and soft capsules. In one embodiment the capsule is a hard gelatin capsule. In another embodiment the capsule is a soft gelatin capsule. In another embodiment of the present disclosure the composition is in form of an alginate capsule made from M-alginate, G-alginate, or combinations of M- and G-alginate. In one embodiment the composition is in form of a capsule made from hydroxypropyl methylcellulose (HPMC). In another embodiment the capsule is a capsule-in-capsule. In still another embodiment the capsule is an acid resistant capsule.

In some embodiments, the 2-((5Z,8Z,11Z,14Z,17Z)-icosa-5,8,11,14,17-pentaenyloxy)butanoic acid, an ester derivative, such as a methyl, ethyl, propyl or butyl ester, or a pharmaceutically acceptable salt, such as magnesium, thereof is present in the pharmaceutical composition in an amount ranging from about 5% to 60% by weight of the total composition, such as from about 5% to about 46% by weight of the total composition, such as from about 5% to about 40% by weight of the total composition, such as from about 10% to about 30% by weight of the total composition, such as from about 10% to about 25% by weight of the total composition, such as from about 15% to about 48% by weight of the total composition, such as from about 20% to about 40% by weight of the total composition, such as from about 40% to about 48% by weight of the total composition, such as from about 20% to about 30% by weight of the total composition. In another embodiment, the 2-((5Z,8Z,11Z,14Z,17Z)-icosa-5,8,11,14,17-pentaenyloxy)butanoic acid, an ester derivative, or a pharmaceutically acceptable salt thereof is present in the pharmaceutical composition in a pharmaceutically effective amount. In one embodiment 2-((5Z,8Z,11Z,14Z,17Z)-icosa-5,8,11,14,17-pentaenyloxy)butanoic acid, an ester derivative, or a pharmaceutically acceptable salt thereof is the sole active ingredient in the composition.

In one embodiment the pharmaceutical composition comprises at least 11% by weight of the total composition of 2-((5Z,8Z,11Z,14Z,17Z)-icosa-5,8,11,14,17-pentaenyloxy)butanoic acid, an ester derivative, such as a methyl, ethyl, propyl or butyl ester, or a pharmaceutically acceptable salt, such as magnesium, thereof. In one embodiment the pharmaceutical composition comprises about 30% by weight of the total composition of 2-((5Z,8Z,11Z,14Z,17Z)-icosa-5,8,11,14,17-pentaenyloxy)butanoic acid, an ester derivative, or a pharmaceutically acceptable salt thereof. That is, the composition comprises about 100 mg of 2-((5Z,8Z,11Z,14Z,17Z)-icosa-5,8,11,14,17-pentaenyloxy)butanoic acid, an ester derivative, or a pharmaceutically acceptable salt thereof per 333 mg of the total composition. In one embodiment the pharmaceutical composition comprises about 15% by weight of the total composition of 2-((5Z,8Z,11Z,14Z,17Z)-icosa-5,8,11,14,17-pentaenyloxy)butanoic acid, an ester derivative, or a pharmaceutically acceptable salt thereof. That is, the composition comprises about 50 mg of 2-((5Z,8Z,11Z,14Z,17Z)-icosa-5,8,11,14,17-pentaenyloxy)butanoic acid, an ester derivative, or a pharmaceutically acceptable salt thereof per 333 mg of the total composition. In one embodiment the pharmaceutical composition comprises about 46% by weight of the total composition of 2-((5Z,8Z,11Z,14Z,17Z)-icosa-5,8,11,14,17-pentaenyloxy)butanoic acid, an ester derivative, or a pharmaceutically acceptable salt thereof. That is, the composition comprises about 153 mg of 2-((5Z,8Z,11Z,14Z,17Z)-icosa-5,8,11,14,17-pentaenyloxy)butanoic acid, an ester derivative, or a pharmaceutically acceptable salt thereof per 333 mg of the total composition. In at least one embodiment the composition comprises about 50 mg to about 500 mg of 2-((5Z,8Z,11Z,14Z,17Z)-icosa-5,8,11,14,17-pentaenyloxy)butanoic acid, an ester derivative, or a pharmaceutically acceptable salt thereof of the total composition, such as about 50 mg, such as about 100 mg, such as about 150 mg, such as about 200 mg, such as about 250 mg, such as about 300 mg, such as about 350 mg, such as about 400 mg, and such as about 450 mg, of the total composition in the fill volume of the dosage form, such as a capsule, being in the range of 150-1000 mg.

In some embodiments, the 2-((5Z,8Z,11Z,14Z,17Z)-icosa-5,8,11,14,17-pentaenyloxy)butanoic acid is present in the pharmaceutical composition in an amount ranging from about 5% to about 60%, such as from about 5% to about 46% by weight of the total composition, such as from about 5% to about 40% by weight of the total composition, such as from about 10% to about 30% by weight of the total composition, such as from about 10% to about 25% by weight of the total composition, such as from about 15% to about 48% by weight of the total composition, such as from about 20% to about 40% by weight of the total composition, such as from about 40% to about 48% by weight of the total composition, such as from about 20% to about 30% by weight of the total composition. In another embodiment, the 2-((5Z,8Z,11Z,14Z,17Z)-icosa-5,8,11,14,17-pentaenyloxy)butanoic acid is present in the composition in a pharmaceutically effective amount.

In one embodiment the pharmaceutical composition comprises about 30% by weight of the total composition of 2-((5Z,8Z,11Z,14Z,17Z)-icosa-5,8,11,14,17-pentaenyloxy)butanoic acid. That is, the composition comprises about 100 mg of 2-((5Z,8Z,11Z,14Z,17Z)-icosa-5,8,11,14,17-pentaenyloxy)butanoic acid, per 333 mg of the total composition. In one embodiment the pharmaceutical composition comprises about 15% by weight of the total composition of 2-((5Z,8Z,11Z,14Z,17Z)-icosa-5,8,11,14,17-pentaenyloxy)butanoic acid. That is, the composition comprises about 50 mg of 2-((5Z,8Z,11Z,14Z,17Z)-icosa-5,8,11,14,17-pentaenyloxy)butanoic acid, per 333 mg of the total composition. In one embodiment the pharmaceutical composition comprises about 46% by weight of the total composition of 2-((5Z,8Z,11Z,14Z,17Z)-icosa-5,8,11,14,17-pentaenyloxy)butanoic acid. That is, the composition comprises about 153 mg of 2-((5Z,8Z,11Z,14Z,17Z)-icosa-5,8,11,14,17-pentaenyloxy)butanoic acid, per 333 mg of the total composition. In at least one embodiment the composition comprises about 50 mg to about 500 mg of 2-((5Z,8Z,11Z,14Z,17Z)-icosa-5,8,11,14,17-pentaenyloxy)butanoic acid, of the total composition, such as about 50 mg, such as about 100 mg, such as about 150 mg, such as about 200 mg, such as about 250 mg, such as about 300 mg, such as about 350 mg, such as about 400 mg, and such as about 450 mg, of the total composition in the fill volume of the dosage form, such as a capsule, being in the range of 150-1000 mg.

In some embodiments, magnesium 2-((5Z,8Z,11Z,14Z,17Z)-icosa-5,8,11,14,17-pentaenyloxy)butanoate is present in the pharmaceutical composition in an amount ranging from about 5% to about 60%, such as from about 20% to about 60% by weight of the total composition. In another embodiment, magnesium 2-((5Z,8Z,11Z,14Z,17Z)-icosa-5,8,11,14,17-pentaenyloxy)butanoate is present in the composition in a pharmaceutically effective amount.

In one embodiment the pharmaceutical composition comprises about 30% by weight of the total composition of magnesium 2-((5Z,8Z,11Z,14Z,17Z)-icosa-5,8,11,14,17-pentaenyloxy)butanoate. That is, the composition comprises about 100 mg of the magnesium salt, per 333 mg of the total composition. In one embodiment the pharmaceutical composition comprises about 15% by weight of the total composition of the magnesium salt of the active ingredient. That is, the composition comprises about 50 mg of magnesium 2-((5Z,8Z,11Z,14Z,17Z)-icosa-5,8,11,14,17-pentaenyloxy)butanoate, per 333 mg of the total composition. In one embodiment the pharmaceutical composition comprises about 46% by weight of the total composition of magnesium 2-((5Z,8Z,11Z,14Z,17Z)-icosa-5,8,11,14,17-pentaenyloxy)butanoate. That is, the composition comprises about 153 mg of magnesium 2-((5Z,8Z,11Z,14Z,17Z)-icosa-5,8,11,14,17-pentaenyloxy)butanoate, per 333 mg of the total composition. In at least one embodiment the composition comprises about 50 mg to about 500 mg of magnesium 2-((5Z,8Z,11Z,14Z,17Z)-icosa-5,8,11,14,17-pentaenyloxy)butanoate, of the total composition, such as about 50 mg, such as about 100 mg, such as about 150 mg, such as about 200 mg, such as about 250 mg, such as about 300 mg, such as about 350 mg, such as about 400 mg, and such as about 450 mg, of the total composition in the fill volume of the dosage form, such as a capsule, being in the range of 150-1000 mg. In at least one embodiment, capsules of other sizes such as for example 150 mg, 300 mg, 500 mg, 600 mg, 700 mg, 800, and 900 mg may be convenient.

In some embodiments of the present disclosure, the capsule fill content ranges from about 0.150 g to about 1.200 g. For example, in some embodiments, the capsule fill content ranges from about 0.300 g to about 0.900 g, from about 0.600 g to about 0.900 g, from about 0.600 g to about 0.800 g, from about 0.800 g to about 1.000, from about 1.000 g to about 1.200 g, or any amount in between. For example, in some embodiments the capsule fill content is about 0.600 g, about 0.800 g, about 1.000 g, or about 1.200 g.

The capsules or other pharmaceutical compositions presently disclosed may be manufactured in low oxygen conditions to inhibit oxidation during the manufacturing process. Preparation of capsules and/or microcapsules in accordance with the present disclosure may be carried out following methods described in the literature. Examples of such methods include, but are not limited to, simple coacervation methods (see, e.g., ES 2009346, EP 0052510, and EP 0346879), complex coacervation methods (see, e.g., GB 1393805), double emulsion methods (see, e.g., U.S. Pat. No. 4,652,441), simple emulsion methods (see, e.g., U.S. Pat. No. 5,445,832), and solvent evaporation methods (see, e.g., GB 2209937). Those methods may, for example, provide for continuous processing and flexibility of batch size.

The present disclosure provides for a pharmaceutical composition comprising 2-((5Z,8Z,11Z,14Z,17Z)-icosa-5,8,11,14,17-pentaenyloxy)butanoic acid, an ester derivative, or pharmaceutically acceptable salt thereof; a triglyceride chosen from MCT oils or LCT oils; and a nonionic surfactant. For example, the present disclosure provides for a pharmaceutical composition comprising 2-((5Z,8Z,11Z,14Z,17Z)-icosa-5,8,11,14,17-pentaenyloxy)butanoic acid; a triglyceride chosen from MCT oils; and a nonionic surfactant. For example, the present disclosure provides for a pharmaceutical composition comprising magnesium 2-((5Z,8Z,11Z,14Z,17Z)-icosa-5,8,11,14,17-pentaenyloxy)butanoate; a triglyceride chosen from MCT oils; and a nonionic surfactant or a pharmaceutical composition comprising 2-((5Z,8Z,11Z,14Z,17Z)-icosa-5,8,11,14,17-pentaenyloxy)butanoic acid in the form of a methyl, ethyl, propyl or butyl ester; a triglyceride chosen from MCT oils; and a nonionic surfactant.

The compositions of the present disclosure can produce dispersions of low or very low mean particle size when mixed with an aqueous medium. Such dispersions can be characterized as nano- or microemulsions. For example, upon delivery, the compositions are thought to produce dispersions or emulsions with gastric or other physiological fluids and are thus considered to be self-nanoemulsifying drug delivery systems (SNEDDS) or self-microemulsifying drug delivery systems (SMEDDS).

Absorption of 2-((5Z,8Z,11Z,14Z,17Z)-icosa-5,8,11,14,17-pentaenyloxy)butanoic acid, an ester derivative, or a pharmaceutically acceptable salt thereof is enhanced by administering to a human a pharmaceutical composition comprising from 5% to 60% by weight of the total composition of 2-((5Z,8Z,11Z,14Z,17Z)-icosa-5,8,11,14,17-pentaenyloxy)butanoic acid, an ester derivative, or a pharmaceutically acceptable salt thereof; from 15% to 60% by weight of the total composition of a medium-chain triglyceride; and from 10% to 60% by weight of the total composition of a nonionic surfactant, which is a self-nanoemulsifying drug delivery system (SNEDDS) or self-microemulsifying drug delivery system (SMEDDS) and forms an emulsion in contact with aqueous media as disclosed herein. In another embodiment absorption of 2-((5Z,8Z,11 Z,14Z,17Z)-icosa-5,8,11,14,17-pentaenyloxy)butanoic acid is enhanced by administering to a human a pharmaceutical composition comprising from 5% to 60% by weight of the total composition of 2-((5Z,8Z,11Z,14Z,17Z)-icosa-5,8,11,14,17-pentaenyloxy)butanoic acid; from 15% to 60% by weight of the total composition of a medium chain triglyceride; and from 10% to 60% by weight of the total composition of a nonionic surfactant, which is a SNEDDS or SMEDDS and forms an emulsion in contact with aqueous media as disclosed herein.

Triglycerides

Suitable triglycerides are chosen from medium-chain triglyceride (MCT) oils or long-chain triglyceride (LCT) oils.

"MCT" as used herein means medium-chain (6 to 12 carbons) aliphatic fatty acid esters of glycerol. In at least one embodiment the MCT oil comprises mainly C8-C10 triglycerides such as capric and caprylic triglyceride. Thus, in at least one embodiment, the MCT oil is derived from capric acid and caprylic acid. In at least one embodiment the MTC oil comprises between 50 and 80% caprylic acid and between 20 to 50% capric acid. In one embodiment the MTC comprises from about 50 to 60% caprylic acid and about 40 to 50% capric acid, such as for example about 56% caprylic acid and about 44% capric acid. In one embodiment the MCT is liquid at room temperature. In at least one embodiment the triglyceride is a MTC in accordance with the European or the US Pharmacopeia. An example of a suitable MCT oil is Miglyol 812 N.

"LCT" as used herein means triglycerides of fatty acids with aliphatic tails longer than 12 carbons. Limited upwards to less than 25 carbons. Suitable LCT oils include, but are not limited to, sesame oil, castor oil, soybean oil, and safflower seed oil.

In at least one embodiment, a MCT oil is used as the triglyceride. In another embodiment a mixture of medium-chained and long-chained oils is used as the triglyceride.

The triglyceride is present in the composition in an amount ranging from for example 15% to 60% by weight of the total composition, such as ranging from 15% to 50% by weight of the total composition, such as ranging from 20% to 49% by weight of the total composition, such as from 20% to 40% by weight of the total composition, such as ranging from 20% to 30% by weight of the total composition, such as ranging from 35% to 40% by weight of the total composition, such as from 30% to 40% by weight of the total composition.

Although preconcentrates with an active pharmaceutical ingredient content ranging from 40-60% and a nonionic surfactant but without MCT could be clear, such pre-concentrates did not demonstrate either homogenous emulsion in the gastrointestinal medium or mono-disperse micelle size distribution.

Surfactants

A surfactant may, for example, lower the surface tension of a liquid or the surface tension between two liquids. For example, surfactants according to the present disclosure may lower the surface tension between the 2-((5Z,8Z,11Z,14Z,17Z)-icosa-5,8,11,14,17-pentaenyloxy)butanoic acid, an ester derivative, or a pharmaceutically acceptable salt thereof and an aqueous solution.

Suitable surfactants include but are not limited to, polysorbates, such as for example, polyoxyethylene (POE)-20-sorbitan monooleate, Tween 80, Crillet 4, polyoxyethylene (POE)-20-sorbitan monolaurate, Tween 60, Tween 40, Tween 20, and Crillet 1; sorbitan esters, such as for example, sorbitan monolaurate, Span 20, and Crill 1; ((Poly(ethylene oxide))-(poly(propylene oxide)) (PEO-PPO)-block copolymers, such as for example, Poloxamer 188, Pluronic/Lutrol F 68; polyoxyethylene (POE) alkyl ethers, such as for example, polyoxyethylene (POE)-10-oleyl ether and Brij 96 V; polyoxyethylene (POE) castor oil, such as for example, polyoxyethylene (POE)-35-castor oil, Cremophor-EL (also named Kolliphor EL), and Etocas 35 HV; polyoxyethylene (POE) hydrogenated castor oil, such as for example, polyoxyethylene (POE)-40-hydrogenated castor oil, Cremophore RH 40 (also named Kolliphor RH 40), hydrogenated castor oil (HCO)-40, and Croduret 40 LD; polyoxyethylene (POE)-60-hydrogenated castor oil, such as for example, Cremophore RH 60, hydrogenated castor oil (HCO)-60; polyoxyethylene (POE)-stearate, such as for example, polyethyleneglycol (PEG)-660-12-hydroxystearate and Solutol HS 15 (also named Kolliphor HS15); phospholipids, such as for example, soybean lecithin, egg lecithin, diolelyl phosphatidyl choline, and distearoyl phosphatidyl glycerol; polyethyleneglycol (PEG)ylated phospholipids; dimyristoyl phosphatidyl choline; Span 80; and Brij 97; or mixtures thereof.

In at least one embodiment, the surfactant is chosen from Solutol HS 15, Cremophor-EL, Cremophore RH 60, Tween 20, Tween 40, Tween 60, Tween 80, Span 80, Brij 97, and mixtures thereof.

In another embodiment, the surfactant is chosen from Tween 20, Tween 40, Tween 60, Tween 80, and mixtures thereof.

In one embodiment, more than one surfactant is used.

In one embodiment, the composition comprises a mixture of Tween 20, Tween 80, and Solutol HS 15 as surfactants.

In another embodiment, the composition comprises a mixture of Tween 80 and Solutol HS 15 as surfactants.

In another embodiment, the composition comprises a mixture of Tween 20 and Solutol HS 15 as surfactants.

The surfactant is present in the composition in an amount ranging from 10% to 60% by weight of the total composition, such as 30% to 60% by weight of the total composition, such as from 30% to 50% by weight of the total composition, such as from 30% to 40% by weight of the total composition, such as from 35% to 50% by weight of the total composition, such as from 35% to 45% by weight of the total composition.

In at least one embodiment of the present disclosure, the composition comprises a surfactant chosen from nonionic, anionic, cationic, and zwitterionic surfactants.

Non-limiting examples of nonionic surfactants suitable for the present disclosure are mentioned below.

Pluronic® surfactants are nonionic copolymers composed of a central hydrophobic polymer (polyoxypropylene(poly(propylene oxide))) with a hydrophilic polymer (polyoxyethylene(poly(ethylene oxide))) on each side. Various commercially-available Pluronic® products are listed in Table 1.

TABLE 1

Examples of Pluronic ® surfactants.

| | Type | Average Molecular Weight (D) | HLB Value |
|---|---|---|---|
| Pluronic ® L-31 | Non-ionic | 1100 | 1.0-7.0 |
| Pluronic ® L-35 | Non-ionic | 1900 | 18.0-23.0 |
| Pluronic ® L-61 | Non-ionic | 2000 | 1.0-7.0 |
| Pluronic ® L-81 | Non-ionic | 2800 | 1.0-7.0 |
| Pluronic ® L-64 | Non-ionic | 2900 | 12.0-18.0 |
| Pluronic ® L-121 | Non-ionic | 4400 | 1.0-7.0 |
| Pluronic ® P-123 | Non-ionic | 5800 | 7-9 |
| Pluronic ® F-68 | Non-ionic | 8400 | >24 |
| Pluronic ® F-108 | Non-ionic | 14600 | >24 |

Brij® are nonionic surfactants comprising polyethylene ethers. Various commercially-available Brij® products are listed in Table 2.

TABLE 2

Examples of Brij ® surfactants.

| | Type | Compound | HLB Value |
|---|---|---|---|
| Brij ® 30 | Non-ionic | Polyoxyethylene(4) lauryl ether | 9.7 |
| Brij ® 35 | Non-ionic | polyoxyethylene (23) lauryl ether | 16.9 |
| Brij ® 52 | Non-ionic | Polyoxyethylene (2) cetyl ether | 5.3 |
| Brij ® 56 | Non-ionic | Polyoxyethylene (10) cetyl ether | 12.9 |
| Brij ® 58 | Non-ionic | Polyoxyethylene (20) cetyl ether | 15.7 |
| Brij ® 72 | Non-ionic | polyoxyethylene (2) stearyl ether | 4.9 |
| Brij ® 76 | Non-ionic | polyoxyethylene (10) stearyl ether | 12.4 |
| Brij ® 78 | Non-ionic | polyoxyethylene (20) stearyl ether | 15.3 |
| Brij ® 92V | Non-ionic | Polyoxyethylene (2) oleyl ether | 4.9 |
| Brij ® 93 | Non-ionic | Polyoxyethylene (2) oleyl ether | 4 |
| Brij ® 96V | Non-ionic | polyethylene glycol oleyl ether | 12.4 |
| Brij ® 97 | Non-ionic | Polyoxyethylene (10) oleyl ether | 12 |
| Brij ® 98 | Non-ionic | Polyoxyethylene (20) oleyl ether | 15.3 |
| Brij ® 700 | Non-ionic | polyoxyethylene (100) stearyl ether | 18 |

Span® are nonionic surfactants comprising sorbitan esters. Span® is available from different sources including Aldrich. Various commercially-available Span® products are listed in Table 3.

TABLE 3

Examples of Span ® surfactants.

| | Type | Compound | HLB Value |
|---|---|---|---|
| Span ® 20 | Non-ionic | sorbitan monolaurate | 8.6 |
| Span ® 40 | Non-ionic | sorbitan monopalmitate | 6.7 |
| Span ® 60 | Non-ionic | sorbitan monostearate | 4.7 |
| Span ® 65 | Non-ionic | sorbitan tristearate | 2.1 |
| Span ® 80 | Non-ionic | sorbitan monooleate | 4.3 |
| Span ® 85 | Non-ionic | Sorbitan trioleate | 1.8 |

Tween® (polysorbates) are nonionic surfactants comprising polyoxyethylene sorbitan esters. Various commercially-available Tween® products are listed in Table 4.

TABLE 4

Examples of Tween ® surfactants.

| | Type | Compound | HLB Value |
|---|---|---|---|
| Tween ® 20 | Non-ionic | polyoxyethylene (20) sorbitan monolaurate | 16.0 |
| Tween ® 40 | Non-ionic | polyoxyethylene (20) sorbitan monopalmitate | 15.6 |
| Tween ® 60 | Non-ionic | polyoxyethylene sorbitan monostearate | 14.9 |
| Tween ® 65 | Non-ionic | polyoxyethylene sorbitan tristearate | 10.5 |

TABLE 4-continued

| Examples of Tween ® surfactants. | | | |
|---|---|---|---|
| | Type | Compound | HLB Value |
| Tween ® 80 | Non-ionic | polyoxyethylene(20)sorbitan monooleate | 15.0 |
| Tween ® 85 | Non-ionic | polyoxyethylene sorbane trioleate | 11.0 |

Myrj® are nonionic surfactants comprising polyoxyethylene fatty acid esters. Various commercially-available Myrj® products are listed in Table 5.

TABLE 5

| Examples of Myrj ® surfactants. | | | |
|---|---|---|---|
| | Type | Compound | HLB Value |
| Myrj ® 45 | Non-ionic | polyoxyethylene monostearate | 11.1 |
| Myrj ® 49 | Non-ionic | polyoxyethylene monostearate | 15.0 |
| Myrj ® 52 | Non-ionic | polyoxyethylene monostearate | 16.9 |
| Myrj ® 53 | Non-ionic | polyoxyethylene monostearate | 17.9 |

Cremophor® are nonionic surfactants. Various commercially-available Cremophor® products are listed in Table 6.

TABLE 6

| Examples of Cremophor ® surfactants. | | | |
|---|---|---|---|
| | Type | Compound | HLB Value |
| Cremophor ® REL | Non-ionic | polyoxyethylated castor oil | 2-14 |
| Cremophor ® RH40 | Non-ionic | hydrogenated polyoxyethylated castor oil | 14-16 |
| Cremophor ® RH60 | Non-ionic | hydrogenated polyoxyethylated castor oil | 15-17 |
| Cremophor ® RO | Non-ionic | hydrogenated polyoxyethylated castor oil | 16.1 |

According to the present disclosure, other exemplary nonionic surfactants include, but are not limited to, diacetyl monoglycerides; diethylene glycol monopalmitostearate; ethylene glycol monopalmitostearate; glyceryl behenate; glyceryl distearate; glyceryl monolinoleate; glyceryl monooleate; glyceryl monostearate; macrogol cetostearyl ether, such as cetomacrogol 1000 and polyoxy 20 cetostearyl ether; macrogol 15 hydroxystearate; macrogol lauril ethers, such as laureth 4 and lauromacrogol 400; macrogol monomethyl ethers; macrogol oleyl ethers, such as polyoxyl 10 oleyl ether; macrogol stearates, such as polyoxyl 40 stearate; menfegol; mono and diglycerides; nonoxinols, such as nonoxinol-9, nonoxinol-10, and nonoxinol-11; octoxinols, such as octoxinol 9 and oxtoxinol 10; polyoxamers, such as polyoxalene, polyoxamer 188, and polyoxamer 407; polyoxyl castor oil, such as polyoxyl 35 castor oil; polyoxyl hydrogenated castor oil, such as polyoxyl 40 hydrogenated castor oil; propylene glycol diacetate; and propylene glycol laurates, such as propylene glycol dilaurate and propylene glycol monolaurate. Further examples include propylene glycol monopalmitostearate; quillaia; sorbitan esters; and sucrose esters.

Anionic surfactants suitable for the present disclosure include, for example, salts of perfluorocarboxylic acids and perfluorosulphonic acid; alkyl sulphate salts, such as sodium dodecyl sulphate and ammonium lauryl sulphate; sulphate ethers, such as sodium lauryl ether sulphate; and alkyl benzene sulphonate salts.

Cationic surfactants suitable for the present disclosure include, for example, quaternary ammonium compounds, such as benzalkonium chloride; cetylpyridinium chlorides; benzethonium chlorides; and cetyl trimethylammonium bromides or other trimethylalkylammonium salts.

Zwitterionic surfactants include, but are limited to, for example dodecyl betaines; coco amphoglycinates; and cocamidopropyl betaines.

In some embodiments of the present disclosure, the surfactant may comprise a phospholipid, derivative thereof, or analogue thereof. Such surfactants may, for example, be chosen from natural, synthetic, and semisynthetic phospholipids, derivatives thereof, and analogues thereof. Exemplary phospholipids surfactants include phosphatidylcholines with saturated, unsaturated and/or polyunsaturated lipids, such as dioleoylphosphatidylcholine, dipentadecanoylphosphatidylcholine, dilauroylphosphatidylcholine, dimyristoylphosphatidylcholine, dipalmitoylphosphatidylcholine, distearoylphosphatidylcholine, di-eicopentaenoyl (EPA)choline, didocosahexaenoyl(DHA)choline, phosphatidylethanolamines; phosphatidylglycerols; phosphatidylserines; and phosphatidylinositols. Other exemplary phospholipid surfactants include soybean lecithin; egg lecithin; diolelyl phosphatidylcholine; distearoyl phosphatidyl glycerol; PEG-ylated phospholipids; and dimyristoyl phosphatidylcholine.

Phospholipids may be "natural" or from a marine origin chosen from, for example, phosphatidylcholine; phosphatidylethanolamine; phosphatidylserine; and phosphatidylinositol. The fatty acid moiety may be chosen from 14:0, 16:0, 16:1n-7, 18:0, 18:1n-9, 18:1n-7, 18:2n-6, 18:3n-3, 18:4n-3, 20:4n-6, 20:5n-3, 22:5n-3 and 22:6n-3, or any combinations thereof. In one embodiment, the fatty acid moiety is chosen from palmitic acid, EPA and DHA.

Other exemplary surfactants suitable for the present disclosure are listed in Table 7.

TABLE 7

| Other surfactants | | |
|---|---|---|
| Surfactant | Type | HBL Value |
| Ethylene glycol distearate | Nonionic | 1.5 |
| Glyceryl monostearate | Nonionic | 3.3 |
| Propylene glycol monostearate | Nonionic | 3.4 |
| Glyceryl monostearate | Nonionic | 3.8 |
| Diethylene glycol monolaurate | Nonionic | 6.1 |
| Acacia | Anionic | 8.0 |
| Cetrimonium bromide | Cationic | 23.3 |
| Cetylpyridinium chloride | Cationic | 26.0 |
| Polyoxamer 188 | Nonionic | 29.0 |
| Sodium lauryl sulphate | Anionic | 40 |

Examples of co-solvents suitable for the present disclosure include, but are not limited to, short chain alcohols comprising from 1 to 6 carbons (for example, ethanol); benzyl alcohol; alkane diols and triols (for example, propylene glycol, glycerol, polyethylene glycols such as PEG and PEG 400); glycol ethers, such as tetraglycol and glycofurol (for example, tetrahydrofurfuryl PEG ether); pyrrolidine derivatives, such as N-methyl pyrrolidone (for example, Pharmasolve®) and 2-pyrrolidone (for example, Soluphor® P); and bile salts, for example sodium deoxycholate. Further examples include ethyl oleate.

In at least one embodiment, the co-solvent is chosen from ethanol, benzyl alcohol, tetraglycol, PEG 400, and triacetin. In another embodiment the surfactant is chosen from PEG 400 and benzyl alcohol.

In some embodiments, the co-solvent is present in the composition in an amount ranging from 0% to 20% by weight of the total composition, such as from 0% to 15% by weight of the total composition, such as from 0% to 10% by weight of the total composition.

SMEDDS/SNEDDS/SEDDS

The compositions of the present disclosure may be in a form of a self-nanoemulsifying drug delivery system (SNEDDS), self-microemulsifying drug delivery system (SMEDDS), or self-emulsifying drug delivery system (SEDDS), wherein the compositions form emulsions in an aqueous solution.

Examples of aqueous solutions include but are not limited to water, gastric media, and intestinal media.

Without being bound by theory, it is believed that the disclosed SNEDDS, SMEDDS, or SEDDS compositions form an emulsion upon contact with gastric and/or intestinal media in the body, comprising micelle particles. The emulsion may, for example, provide for increased or improved stability of the 2-((5Z,8Z,11Z,14Z,17Z)-icosa-5,8,11,14,17-pentaenyloxy)butanoic acid, an ester derivative, or a pharmaceutically acceptable salt thereof for uptake in the body and/or provide increased or improved surface area for absorption. SNEDDS, SMEDDS and SEDDS may thus provide for enhanced or improved hydrolysis, solubility, bioavailability, absorption, or any combinations thereof of 2-((5Z,8Z,11Z,14Z,17Z)-icosa-5,8,11,14,17-pentaenyloxy) butanoic acid, an ester derivative, or a pharmaceutically acceptable salt thereof in vivo.

The SNEDDS, SMEDDS or SEDDS compositions presently disclosed may comprise a particle size, that is a particle diameter, ranging from about 5 nm to about 5 μm. For example, in some embodiments, the particle size ranges from about 5 nm to about 1 m, such as from about 10 nm to about 750 nm, from about 50 nm to about 500 nm, or from about 150 nm to about 350 nm, as measured using a Malvern Zetasizer (Malvern Instrument, Worcestershire, UK) with particle size measuring range of 0.6-6000 nm and Zeta potential of particle range of 3 nm-5 μm.

Methods or Uses

The present disclosure further provides for a method of treating, preventing, and/or regulating at least one health problem in a subject in need thereof comprising administering to the subject a composition comprising 2-((5Z,8Z,11Z,14Z,17Z)-icosa-5,8,11,14,17-pentaenyloxy)butanoic acid, as an ester derivative, or a pharmaceutically acceptable salt thereof; a triglyceride; and a surfactant, wherein the at least one health problem is chosen from a disorder responding to the activation or modulation of at least one of the human peroxisome proliferator-activated receptor (PPAR) isoforms α, γ or δ; a dyslipidemic condition, for example hypertriglyceridemia (HTG); dyslipidemia; mixed dyslipidemia; elevated triglyceride levels, non-HDL cholesterol levels, LDL cholesterol levels, and/or VLDL cholesterol levels; the increase of HDL cholesterol; obesity or an overweight condition; the reduction of body weight and/or for preventing body weight gain; a fatty liver disease, for example non-alcoholic fatty liver disease (NAFLD); an inflammatory disease or condition; atherosclerosis; peripheral insulin resistance and/or a diabetic condition; type 2 diabetes; and the reduction of plasma insulin, blood glucose and/or serum triglycerides.

Because the active ingredient is highly lipophilic and thus demonstrates very low water solubility, several experiments were performed to find optimal solvents or SMEDDS that would increase the solubility and/or form stable emulsions in water and bio-relevant media, such as gastric juice and intestinal content. Surprisingly, the inventors found that compositions within certain ranges of components could form emulsions at fast or medium speed-in such a way that emulsions could be formed in an in vivo setting. In addition, compositions according to the present disclosure form both micro- and nano-emulsions with particle size as low as 10 nm to 150 nm, that were stable in both gastric juice and intestinal fluid. Thus, the presently disclosed compositions may be used in a pharmaceutical formulation with or without enteric capabilities. A SNEDDS formulation was even shown to improve the in vivo bioavailability by at least 30%. This improvement was demonstrated by a predominant increase in the Port-vein uptake, thereby possibly increasing the pharmacological activity by increasing liver uptake as compared to increased lymph uptake, and thus without increasing the systemic adverse-effects.

The present disclosure is also directed to a self-microemulsifying drug delivery system (SMEDDS), self-nanoemulsifying drug delivery system (SNEDDS), or self-emulsifying drug delivery system (SEDDS) comprising 2-((5Z,8Z,11Z,14Z,17Z)-icosa-5,8,11,14,17-pentaenyloxy) butanoic acid, an ester derivative, or a pharmaceutically acceptable salt thereof, a triglyceride; and a surfactant, wherein the composition forms an emulsion in an aqueous solution for the treatment and/or regulation of at least one health problem chosen from a disorder responding to the activation or modulation of at least one of the human peroxisome proliferator-activated receptor (PPAR) isoforms α, γ or δ; a dyslipidemic condition, for example hypertriglyceridemia (HTG); dyslipidemia; mixed dyslipidemia; elevated triglyceride levels, non-HDL cholesterol levels, LDL cholesterol levels, and/or VLDL cholesterol levels; the increase of HDL cholesterol; obesity or an overweight condition; the reduction of body weight and/or for preventing body weight gain; a fatty liver disease, for example non-alcoholic fatty liver disease (NAFLD); an inflammatory disease or condition; atherosclerosis; peripheral insulin resistance and/or a diabetic condition; type 2 diabetes; and the reduction of plasma insulin, blood glucose and/or serum triglycerides.

In one embodiment, the present disclosure provides for a method of treating at least one health problem in a subject in need thereof, comprising administering to the subject a composition comprising a pharmaceutically-effective amount of 2-((5Z,8Z,11Z,14Z,17Z)-icosa-5,8,11,14,17-pentaenyloxy)butanoic acid, an ester derivative, or a pharmaceutically acceptable salt thereof; a triglyceride; and a surfactant. In some embodiments, the method treats at least one of elevated triglyceride levels, non-HDL cholesterol levels, LDL cholesterol levels and/or VLDL cholesterol levels. For example, the method may reduce triglyceride levels from about 30% to about 80%, such as from about 40% to about 70%, such as from about 40% to about 60%, or from about 30% to about 50%, in a subject with elevated triglyceride levels.

In at least one embodiment, at least one disease or condition is atherosclerosis. For example, the present disclosure further encompasses a method of reducing and/or slowing the progression of atherosclerosis development. The methods presently disclosed may, for example, reduce at least one of plasma insulin, blood glucose, and serum triglycerides in a subject in need thereof. The present disclosure also provides for a method of treating and/or preventing at least one of elevated triglyceride levels, elevated VLDL/LDL cholesterol levels and low HDL cholesterol levels in a subject in need thereof.

In still a further embodiment, the present disclosure provides for a method for enhancing at least one parameter chosen from hydrolysis, solubility, bioavailability, and/or absorption of 2-((5Z,8Z,11Z,14Z,17Z)-icosa-5,8,11,14,17-pentaenyloxy)butanoic acid, an ester derivative, or a pharmaceutically acceptable salt thereof, comprising administering to a human in need thereof a composition comprising 2-((5Z,8Z,11Z,14Z,17Z)-icosa-5,8,11,14,17-pentaenyloxy) butanoic acid, an ester derivative, or a pharmaceutically acceptable salt thereof; a triglyceride; and a surfactant; wherein the hydrolysis, solubility, bioavailability, and/or absorption of 2-((5Z,8Z,11Z,14Z,17Z)-icosa-5,8,11,14,17-pentaenyloxy)butanoic acid, an ester derivative, or a pharmaceutically acceptable salt thereof are enhanced when compared to 2-((5Z,8Z,11Z,14Z,17Z)-icosa-5,8,11,14,17-pentaenyloxy)butanoic acid, an ester derivative, or a pharmaceutically acceptable salt thereof without a triglyceride and/or surfactant. In addition, the composition can form an emulsion in an aqueous solution. In some embodiments, the aqueous solution is gastric media and/or intestinal media. The bioavailability may be increased by at least 20%, such as by about 30% or by at least 40% compared to the same fatty acid derivative not being formulated with a triglyceride and/or surfactant.

In yet another embodiment, the dosage for the composition comprising 2-((5Z,8Z,11Z,14Z,17Z)-icosa-5,8,11,14,17-pentaenyloxy)butanoic acid, an ester derivative, or a pharmaceutically acceptable salt thereof; a triglyceride; and a surfactant is about 0.150 g to about 2.5 g per day of the composition, such as about 0.200 g to about 2 g per day of the composition, including from about 0.300 g to about 1.2 g per day of the composition, and about 0.600 g to about 1.2 g per day of the composition.

The compositions presently disclosed may be administered in from 1 to 10 times per day, such as from 1 to 4 times a day, such as once, twice, three times, or four times per day. The administration may be oral, or any other form of administration that provides a dosage of 2-((5Z,8Z,11Z,14Z,17Z)-icosa-5,8,11,14,17-pentaenyloxy)butanoic acid, an ester derivative, or a pharmaceutically acceptable salt thereof to a subject, such as a human.

DESCRIPTION OF CERTAIN EMBODIMENTS

The present disclosure is directed to a composition comprising a therapeutically effective amount of 2-((5Z,8Z,11Z,14Z,17Z)-icosa-5,8,11,14,17-pentaenyloxy)butanoic acid, an ester derivative, or a pharmaceutically acceptable salt thereof; a triglyceride; and a surfactant.

In one embodiment, a composition comprising a therapeutically effective amount of 2-((5Z,8Z,11Z,14Z,17Z)-icosa-5,8,11,14,17-pentaenyloxy)butanoic acid, an ester derivative, or a pharmaceutically acceptable salt thereof; a triglyceride; a surfactant; and a co-solvent is provided. In one embodiment, a composition comprising a therapeutically effective amount of 2-((5Z,8Z,11Z,14Z,17Z)-icosa-5,8,11,14,17-pentaenyloxy)butanoic acid, a $C_1$-$C_6$-alkyl or phenyl ester derivative, or a pharmaceutically acceptable salt thereof; a triglyceride chosen from MCT or LCT oils; a nonionic surfactant; and a co-solvent is provided.

In one embodiment, a composition comprising a therapeutically effective amount of 2-((5Z,8Z,11Z,14Z,17Z)-icosa-5,8,11,14,17-pentaenyloxy)butanoic acid, an ester derivative, or a pharmaceutically acceptable salt thereof; a triglyceride, such as an MCT oil; a surfactant, chosen from polysorbates; and a co-solvent, such as PEG-400 is provided.

In one embodiment, a composition comprising a therapeutically effective amount of 2-((5Z,8Z,11Z,14Z,17Z)-icosa-5,8,11,14,17-pentaenyloxy)butanoic acid, an ester derivative, or a pharmaceutically acceptable salt thereof; a triglyceride, such as an MCT oil; and a mixture of Tween 80, Tween 20 and Solutol HS15 is provided.

In one embodiment, a composition comprising a therapeutically effective amount of 2-((5Z,8Z,11Z,14Z,17Z)-icosa-5,8,11,14,17-pentaenyloxy)butanoic acid, an ester derivative, or a pharmaceutically acceptable salt thereof; a triglyceride, such as an MCT oil; a mixture of Tween 80 and Solutol HS15; and PEG 400 is provided.

In one embodiment, a composition comprising a therapeutically effective amount of 2-((5Z,8Z,11Z,14Z,17Z)-icosa-5,8,11,14,17-pentaenyloxy)butanoic acid, an ester derivative, or a pharmaceutically acceptable salt thereof; a triglyceride, such as an MCT oil; a mixture of Tween 20 and Solutol HS15; and PEG 400 is provided.

In one embodiment, a composition comprising a therapeutically effective amount of 2-((5Z,8Z,11Z,14Z,17Z)-icosa-5,8,11,14,17-pentaenyloxy)butanoic acid, an ester derivative, or a pharmaceutically acceptable salt thereof; an MCT oil; and Tween 80 is provided.

In one embodiment, a composition comprising a therapeutically effective amount of 2-((5Z,8Z,11Z,14Z,17Z)-icosa-5,8,11,14,17-pentaenyloxy)butanoic acid, an ester derivative, or a pharmaceutically acceptable salt thereof; an MCT oil; and Tween 20 is provided.

In one embodiment, a composition comprising a therapeutically effective amount of 2-((5Z,8Z,11Z,14Z,17Z)-icosa-5,8,11,14,17-pentaenyloxy)butanoic acid, an ester derivative, or a pharmaceutically acceptable salt thereof; an MCT oil; Tween 80 and Tween 20 is provided.

In one embodiment, a composition comprising a therapeutically effective amount of 2-((5Z,8Z,11Z,14Z,17Z)-icosa-5,8,11,14,17-pentaenyloxy)butanoic acid; an MCT oil; Tween 80 and Tween 20 is provided.

In one embodiment, a composition comprising 40% by weight of 2-((5Z,8Z,11Z,14Z,17Z)-icosa-5,8,11,14,17-pentaenyloxy)butanoic acid, an ester derivative, or a pharmaceutically acceptable salt thereof; 30% by weight of an MCT oil; and 30% by weight of Tween 20 is provided.

In one embodiment, a composition comprising 30% by weight of 2-((5Z,8Z,11Z,14Z,17Z)-icosa-5,8,11,14,17-pentaenyloxy)butanoic acid, an ester derivative, or a pharmaceutically acceptable salt thereof; 30% by weight of an MCT oil; and 40% by weight of Tween 20 is provided.

In one embodiment, a composition comprising 30% by weight of ethyl 2-((5Z,8Z,11Z,14Z,17Z)-icosa-5,8,11,14,17-pentaenyloxy)butanoate; 30% by weight of an MCT oil, such as for example for example Miglyol 812N; and 40% by weight of Tween 20 is provided.

In one embodiment, a composition comprising magnesium 2-((5Z,8Z,11Z,14Z,17Z)-icosa-5,8,11,14,17-pentaenyloxy)butanoate; an MCT oil; and Tween 20 or Tween 80 is provided.

In one embodiment, a composition comprising 50% by weight of magnesium 2-((5Z,8Z,11Z,14Z,17Z)-icosa-5,8,11,14,17-pentaenyloxy)butanoate; 40% by weight of an MCT oil; and 10% by weight of Tween 20 is provided. In one embodiment, a composition comprising 30% by weight of magnesium 2-((5Z,8Z,11Z,14Z,17Z)-icosa-5,8,11,14,17-pentaenyloxy)butanoate; 50% by weight of an MCT oil; and 20% by weight of Tween 80 is provided.

In one embodiment, a composition comprising 46.2% by weight of 2-((5Z,8Z,11Z,14Z,17Z)-icosa-5,8,11,14,17-pentaenyloxy)butanoate; 23.1% by weight of an Miglyol 812N;

and 30.8% by weight of Tween 20, Tween 80, Chreomophor EL or Solutol HS15 is provided.

The compositions according to the present disclosure are preconcentrates. Accordingly these compositions or preconcentrates form nano- or microemulsions in contact with aqueous media.

The present disclosure is also directed to a self-nanoemulsifying drug delivery system (SNEDDS), self-microemulsifying drug delivery system (SMEDDS), or self-emulsifying drug delivery system (SEDDS) comprising 2-((5Z,8Z,11Z,14Z,17Z)-icosa-5,8,11,14,17-pentaenyloxy)butanoic acid, an ester derivative, or a pharmaceutically acceptable salt thereof; a triglyceride; and a surfactant; wherein the composition forms an emulsion in an aqueous solution. The present disclosure is also directed to a self-nanoemulsifying drug delivery system (SNEDDS), self-microemulsifying drug delivery system (SMEDDS), or self-emulsifying drug delivery system (SEDDS) comprising 2-((5Z,8Z,11Z,14Z,17Z)-icosa-5,8,11,14,17-pentaenyloxy)butanoic acid, a $C_1$-$C_6$-alkyl or phenyl ester derivative, or a pharmaceutically acceptable salt, such as a magnesium salt, thereof; a triglyceride chosen from MCT or LCT oils; and a nonionic surfactant; wherein the composition forms an emulsion in an aqueous solution.

In one embodiment the present disclosure relates to a self-nanoemulsifying drug delivery system (SNEDDS), self-microemulsifying drug delivery system (SMEDDS), or self-emulsifying drug delivery system (SEDDS) comprising a pharmaceutical composition comprising: from 5% to 60% by weight of the total composition of 2-((5Z,8Z,11Z,14Z,17Z)-icosa-5,8,11,14,17-pentaenyloxy)butanoic acid, an ester derivative, or a pharmaceutically acceptable salt thereof; from 15% to 60% by weight of the total composition of a medium-chain triglyceride (MCT) oil; and from 10% to 60% by weight of the total composition of a nonionic surfactant.

The present disclosure is also directed to a self-nanoemulsifying drug delivery system (SNEDDS), self-microemulsifying drug delivery system (SMEDDS) or self-emulsifying drug delivery system (SEDDS), comprising 2-((5Z,8Z,11Z,14Z,17Z)-icosa-5,8,11,14,17-pentaenyloxy)butanoic acid, an ester derivative, or a pharmaceutically acceptable salt thereof; a triglyceride; a surfactant; and a co-solvent, wherein the composition forms an emulsion in an aqueous solution. The present disclosure is also directed to a self-nanoemulsifying drug delivery system (SNEDDS), self-microemulsifying drug delivery system (SMEDDS) or self-emulsifying drug delivery system (SEDDS), comprising 2-((5Z,8Z,11Z,14Z,17Z)-icosa-5,8,11,14,17-pentaenyloxy)butanoic acid, a $C_1$-$C_6$-alkyl or phenyl ester derivative, or a pharmaceutically acceptable salt, such as a magnesium salt, thereof; a triglyceride chosen from MCT or LCT oils; a nonionic surfactant; and a co-solvent, wherein the composition forms an emulsion in an aqueous solution.

The active pharmaceutical ingredient in the SNEDDS, SMEDDS and SEDDS according to the present disclosure may be in the form of its (R)-enantiomer, (S)-enantiomer or as a mixture of its (R) and (S)-enantiomers.

In one embodiment, a self-nanoemulsifying drug delivery system (SNEDDS), self-microemulsifying drug delivery system (SMEDDS), or self-emulsifying drug delivery system (SEDDS), comprising a composition comprising 2-((5Z,8Z,11Z,14Z,17Z)-icosa-5,8,11,14,17-pentaenyloxy)butanoic acid, an ester derivative, or a pharmaceutically acceptable salt thereof; a triglyceride, such as an MCT oil; a surfactant, chosen from polysorbates; and a co-solvent, such as PEG-400, wherein the composition forms an emulsion in an aqueous solution is provided.

In one embodiment, a self-nanoemulsifying drug delivery system (SNEDDS), self-microemulsifying drug delivery system (SMEDDS), or self-emulsifying drug delivery system (SEDDS), comprising 2-((5Z,8Z,11Z,14Z,17Z)-icosa-5,8,11,14,17-pentaenyloxy)butanoic acid, an ester derivative, or a pharmaceutically acceptable salt thereof; a triglyceride, such as an MCT oil; and a mixture of Tween 80, Tween 20 and Solutol HS15, wherein the composition forms an emulsion in an aqueous solution is provided.

In one embodiment, a self-nanoemulsifying drug delivery system (SNEDDS), self-microemulsifying drug delivery system (SMEDDS), or self-emulsifying drug delivery system (SEDDS), comprising 2-((5Z,8Z,11Z,14Z,17Z)-icosa-5,8,11,14,17-pentaenyloxy)butanoic acid, an ester derivative, or a pharmaceutically acceptable salt thereof; a triglyceride, such as an MCT oil; a mixture of Tween 80 and Solutol HS15; and PEG 400, wherein the composition forms an emulsion in an aqueous solution is provided.

In one embodiment, a self-nanoemulsifying drug delivery system (SNEDDS), self-microemulsifying drug delivery system (SMEDDS), or self-emulsifying drug delivery system (SEDDS), comprising 2-((5Z,8Z,11Z,14Z,17Z)-icosa-5,8,11,14,17-pentaenyloxy)butanoic acid, an ester derivative, or a pharmaceutically acceptable salt thereof; a triglyceride, such as an MCT oil; a mixture of Tween 20 and Solutol HS15; and PEG 400, wherein the composition forms an emulsion in an aqueous solution is provided.

In one embodiment, a self-nanoemulsifying drug delivery system (SNEDDS), self-microemulsifying drug delivery system (SMEDDS), or self-emulsifying drug delivery system (SEDDS), comprising 2-((5Z,8Z,11Z,14Z,17Z)-icosa-5,8,11,14,17-pentaenyloxy)butanoic acid, an ester derivative, or a pharmaceutically acceptable salt thereof; an MCT oil; and Tween 80, wherein the composition forms an emulsion in an aqueous solution is provided.

In one embodiment, a self-nanoemulsifying drug delivery system (SNEDDS), self-microemulsifying drug delivery system (SMEDDS), or self-emulsifying drug delivery system (SEDDS), comprising 2-((5Z,8Z,11Z,14Z,17Z)-icosa-5,8,11,14,17-pentaenyloxy)butanoic acid, an ester derivative, or a pharmaceutically acceptable salt thereof; an MCT oil; and Tween 20, wherein the composition forms an emulsion in an aqueous solution is provided.

In one embodiment, a self-nanoemulsifying drug delivery system (SNEDDS), self-microemulsifying drug delivery system (SMEDDS), or self-emulsifying drug delivery system (SEDDS), comprising 40% by weight of 2-((5Z,8Z,11Z,14Z,17Z)-icosa-5,8,11,14,17-pentaenyloxy)butanoic acid, an ester derivative, or a pharmaceutically acceptable salt thereof; 30% by weight of an MCT oil; and 30% by weight of Tween 20, wherein the composition forms an emulsion in an aqueous solution is provided.

In one embodiment, a self-microemulsifying drug delivery system (SMEDDS) comprising 30% by weight of 2-((5Z,8Z,11Z,14Z,17Z)-icosa-5,8,11,14,17-pentaenyloxy)butanoic acid, an ester derivative, or a pharmaceutically acceptable salt thereof; 30% by weight of an MCT oil; and 40% by weight of Tween 20 is provided.

In one embodiment, a self-microemulsifying drug delivery system (SMEDDS) comprising 2-((5Z,8Z,11Z,14Z,17Z)-icosa-5,8,11,14,17-pentaenyloxy)butanoic acid, magnesium salt; an MCT oil; and Tween 20 or Tween 80 is provided.

In one embodiment, a self-microemulsifying drug delivery system (SMEDDS) comprising 50% by weight of 2-((5Z,8Z,11Z,14Z,17Z)-icosa-5,8,11,14,17-pentaenyloxy) butanoic acid, magnesium salt; 40% by weight of an MCT oil; and 10% by weight of Tween 20 is provided. In one embodiment, a self-microemulsifying drug delivery system (SMEDDS) comprising 30% by weight of 2-((5Z,8Z,11Z, 14Z,17Z)-icosa-5,8,11,14,17-pentaenyloxy)butanoic acid, magnesium salt; 50% by weight of an MCT oil; and 20% by weight of Tween 80 is provided.

The present disclosure is more particularly directed to a composition comprising a therapeutically effective amount of 2-((5Z,8Z,11Z,14Z,17Z)-icosa-5,8,11,14,17-pentaenyloxy)butanoic acid; a triglyceride; and a surfactant. The present disclosure is more particularly directed to a composition comprising a therapeutically effective amount of 2-((5Z,8Z,11Z,14Z,17Z)-icosa-5,8,11,14,17-pentaenyloxy) butanoic acid; a triglyceride chosen from a MCT or LTC oil; and a nonionic surfactant.

In one embodiment, a composition comprising a therapeutically effective amount of 2-((5Z,8Z,11Z,14Z,17Z)-icosa-5,8,11,14,17-pentaenyloxy)butanoic acid; a triglyceride; a surfactant; and a co-solvent is provided. In one embodiment, a composition comprising a therapeutically effective amount of 2-((5Z,8Z,11Z,14Z,17Z)-icosa-5,8,11, 14,17-pentaenyloxy)butanoic acid; a triglyceride chosen from a MCT or LCT oil; a nonionic surfactant; and a co-solvent is provided.

In one embodiment, a composition comprising a therapeutically effective amount of 2-((5Z,8Z,11Z,14Z,17Z)-icosa-5,8,11,14,17-pentaenyloxy)butanoic acid; a triglyceride, such as an MCT oil; a surfactant, chosen from polysorbates; and a co-solvent, such as PEG-400 is provided.

In one embodiment, a composition comprising a therapeutically effective amount of 2-((5Z,8Z,11Z,14Z,17Z)-icosa-5,8,11,14,17-pentaenyloxy)butanoic acid; a triglyceride, such as an MCT oil; and a mixture of Tween 80, Tween 20 and Solutol HS15 is provided.

In one embodiment, a composition comprising a therapeutically effective amount of 2-((5Z,8Z,11Z,14Z,17Z)-icosa-5,8,11,14,17-pentaenyloxy)butanoic acid; a triglyceride, such as an MCT oil; a mixture of Tween 80 and Solutol HS15; and PEG 400 is provided.

In one embodiment, a composition comprising a therapeutically effective amount of 2-((5Z,8Z,11Z,14Z,17Z)-icosa-5,8,11,14,17-pentaenyloxy)butanoic acid; a triglyceride, such as an MCT oil; a mixture of Tween 20 and Solutol HS15; and PEG 400 is provided.

In one embodiment, a composition comprising a therapeutically effective amount of 2-((5Z,8Z,11Z,14Z,17Z)-icosa-5,8,11,14,17-pentaenyloxy)butanoic acid; an MCT oil; and Tween 80 is provided.

In one embodiment, a composition comprising a therapeutically effective amount of 2-((5Z,8Z,11 Z,14Z,17Z)-icosa-5,8,11,14,17-pentaenyloxy)butanoic acid; an MCT oil; and Tween 20 is provided.

In one embodiment, a composition comprising 40% by weight of 2-((5Z,8Z,11Z,14Z,17Z)-icosa-5,8,11,14,17-pentaenyloxy)butanoic acid; 30% by weight of an MCT oil, such as for example Miglyol 812 N; and 30% by weight of Tween 20 is provided.

In one embodiment, a composition comprising 30% by weight of 2-((5Z,8Z,11Z,14Z,17Z)-icosa-5,8,11,14,17-pentaenyloxy)butanoic acid; 30% by weight of an MCT oil; and 40% by weight of Tween 20 is provided.

In one embodiment, the composition according to the present disclosure comprises from 5% to 46% by weight of the total composition of 2-((5Z,8Z,11Z,14Z,17Z)-icosa-5,8, 11,14,17-pentaenyloxy)butanoic acid; from 20% to 49% by weight of the total composition of a medium-chain triglyceride (MCT) oil; and from 30% to 60% by weight of the total composition of a nonionic surfactant.

In one embodiment, the composition according to the present disclosure comprises from 15% to 48% by weight of the total composition of 2-((5Z,8Z,11Z,14Z,17Z)-icosa-5,8, 11,14,17-pentaenyloxy)butanoic acid; from 20% to 40% by weight of the total composition of a medium-chain triglyceride (MCT) oil; and from 30% to 50% by weight of the total composition of a nonionic surfactant.

In one embodiment, the composition according to the present disclosure comprises from 40% to 48% by weight of the total composition of 2-((5Z,8Z,11Z,14Z,17Z)-icosa-5,8, 11,14,17-pentaenyloxy)butanoic acid; from 20% to 30% by weight of the total composition of a medium-chain triglyceride (MCT) oil; and from 30% to 40% by weight of the total composition of a nonionic surfactant.

In one embodiment disclosure the composition according to the present disclosure comprises from 10% to 25% by weight of the total composition of 2-((5Z,8Z,11Z,14Z,17Z)-icosa-5,8,11,14,17-pentaenyloxy)butanoic acid; from 35% to 49% by weight of the total composition of a medium-chain triglyceride (MCT) oil; and from 35% to 50% by weight of the total composition of a nonionic surfactant.

At least one embodiment of the present disclosure relates to the use of a composition comprising 2-((5Z,8Z,11Z,14Z, 17Z)-icosa-5,8,11,14,17-pentaenyloxy)butanoic acid, an ester derivative, or a pharmaceutically acceptable salt thereof, a triglyceride, and a surfactant, for enhancing the hydrolysis, solubility, bioavailability, and/or absorption of 2-((5Z,8Z,11Z,14Z,17Z)-icosa-5,8,11,14,17-pentaenyloxy) butanoic acid, an ester derivative, or a pharmaceutically acceptable salt thereof, in a human in need thereof, wherein the hydrolysis, solubility, bioavailability, and/or absorption of 2-((5Z,8Z,11Z,14Z,17Z)-icosa-5,8,11,14,17-pentaenyloxy)butanoic acid, an ester derivative, or a pharmaceutically acceptable salt thereof are enhanced when compared to 2-((5Z,8Z,11Z,14Z,17Z)-icosa-5,8,11,14,17-pentaenyloxy) butanoic acid, an ester derivative, or a pharmaceutically acceptable salt thereof without a triglyceride or surfactant. At least one embodiment of the present disclosure relates to the use of a composition comprising 2-((5Z,8Z,11Z,14Z, 17Z)-icosa-5,8,11,14,17-pentaenyloxy)butanoic acid, a $C_1$-$C_6$-alkyl or phenyl ester derivative, or a pharmaceutically acceptable salt, such as a magnesium salt, thereof, a triglyceride chosen from a MCT or LCT oil, and a nonionic surfactant, for enhancing the hydrolysis, solubility, bioavailability, and/or absorption of 2-((5Z,8Z,11Z,14Z,17Z)-icosa-5,8,11,14,17-pentaenyloxy)butanoic acid, a $C_1$-$C_6$-alkyl or phenyl ester derivative, or a pharmaceutically acceptable salt, such as a magnesium salt, thereof, in a human in need thereof, wherein the hydrolysis, solubility, bioavailability, and/or absorption of 2-((5Z,8Z,11Z,14Z,17Z)-icosa-5,8,11, 14,17-pentaenyloxy)butanoic acid, a $C_1$-$C_6$-alkyl or phenyl ester derivative, or a pharmaceutically acceptable salt, such as a magnesium salt, thereof are enhanced when compared to the active ingredient mentioned above without a triglyceride chosen from a MCT or LCT oil or nonionic surfactant.

In at least one embodiment the composition according to the present disclosure comprises 2-((5Z,8Z,11Z,14Z,17Z)-icosa-5,8,11,14,17-pentaenyloxy)butanoic acid, polysorbate 20, and Miglyol 812N in a weight ratio of about 2.5-3.5: 3.5-4.5:2.5-3.5.

In at least one embodiment the composition according to the present disclosure comprises 2-((5Z,8Z,11Z,14Z,17Z)- icosa-5,8,11,14,17-pentaenyloxy)butanoic acid, polysorbate 20, and Miglyol 812N in a weight ratio of about 3:4:3.

In at least one embodiment the composition according to the present disclosure comprises 2-((5Z,8Z,11Z,14Z,17Z)-icosa-5,8,11,14,17-pentaenyloxy)butanoic acid, polysorbate 20, and Miglyol 812N in a weight ratio of 3:4:3.

In at least one embodiment the composition according to the present disclosure comprises about 250 mg to about 350 mg 2-((5Z,8Z,11Z,14Z,17Z)-icosa-5,8,11,14,17-pentaenyloxy)butanoic acid, about 350 mg to about 450 mg polysorbate 20, and about 250 mg to about 350 mg Miglyol 812N per gram of the composition.

In at least one embodiment the composition according to the present disclosure comprises 250 mg to 350 mg 2-((5Z,8Z,11Z,14Z,17Z)-icosa-5,8,11,14,17-pentaenyloxy)butanoic acid, 350 mg to 450 mg polysorbate 20, and 250 mg to 350 mg Miglyol 812N per gram of the composition.

In at least one embodiment the composition according to the present disclosure comprises about 225 mg to about 325 mg 2-((5Z,8Z,11Z,14Z,17Z)-icosa-5,8,11,14,17-pentaenyloxy)butanoic acid, about 325 mg to about 425 mg polysorbate 20, and about 225 mg to about 325 mg Miglyol 812N per gram of the composition.

In at least one embodiment the composition according to the present disclosure comprises 225 mg to 325 mg 2-((5Z,8Z,11Z,14Z,17Z)-icosa-5,8,11,14,17-pentaenyloxy)butanoic acid, 325 mg to 425 mg polysorbate 20, and 225 mg to 325 mg Miglyol 812N per gram of the composition.

In at least one embodiment the composition according to the present disclosure comprises about 300 mg 2-((5Z,8Z,11Z,14Z,17Z)-icosa-5,8,11,14,17-pentaenyloxy)butanoic acid, about 400 mg polysorbate 20, and about 300 mg Miglyol 812N per gram of the composition.

In at least one embodiment the composition according to the present disclosure comprises 300 mg 2-((5Z,8Z,11Z,14Z,17Z)-icosa-5,8,11,14,17-pentaenyloxy)butanoic acid, 400 mg polysorbate 20, and 300 mg Miglyol 812N per gram of the composition.

In at least one embodiment, the composition according to the present disclosure comprises from 5% to 60% by weight of the total composition of magnesium 2-((5Z,8Z,11Z,14Z,17Z)-icosa-5,8,11,14,17-pentaenyloxy)butanoate; from 15% to 60% by weight of the total composition of a medium-chain triglyceride (MCT) oil; and from 10% to 60% by weight of the total composition of a nonionic surfactant.

In at least one embodiment, the composition according to the present disclosure comprises from 20% to 60% by weight of the total composition of magnesium 2-((5Z,8Z,11Z,14Z,17Z)-icosa-5,8,11,14,17-pentaenyloxy)butanoate; from 40% to 60% by weight of the total composition of a medium-chain triglyceride (MCT) oil; and from 10% to 25% by weight of the total composition of a nonionic surfactant.

In at least one embodiment, the composition according to the present disclosure comprises about 11-40% by weight of the total composition of 2-((5Z,8Z,11Z,14Z,17Z)-icosa-5,8,11,14,17-pentaenyloxy)butanoic acid in the form of a pharmaceutically acceptable salt, and about 60-89% by weight of the total composition of a mixture comprising a polysorbate and a medium-chain triglyceride, wherein the weight ratio of the polysorbate and the medium-chain triglyceride is about 2:3 to 3:2. In another embodiment the composition according to the present disclosure comprises about 30-38% by weight of the total composition of 2-((5Z,8Z,11Z,14Z,17Z)-icosa-5,8,11,14,17-pentaenyloxy)butanoic acid in the form of a pharmaceutically acceptable salt, and about 60-89% by weight of the total composition of a mixture comprising a polysorbate and a medium-chain triglyceride, wherein the weight ratio of the polysorbate and the medium-chain triglyceride is about 2:3 to 3:2.

In at least one embodiment, the composition according to the present disclosure comprising about 11-40% by weight of the total composition of 2-((5Z,8Z,11Z,14Z,17Z)-icosa-5,8,11,14,17-pentaenyloxy)butanoic acid in the form of a pharmaceutically acceptable salt, such as for example 30-38% by weight of the total composition, and about 60-89% by weight of the total composition or about 62-70% by weight of the total composition, as the case may be, of a mixture comprising a polysorbate and a medium-chain triglyceride, wherein the weight ratio of the polysorbate and the medium-chain triglyceride is about 2:3 to 3:2, further comprises from about 0-15% by weight of the total composition of a co-solvent, wherein the co-solvent replaces from 0-15% by weight of the mixture comprising a polysorbate and a medium-chain triglyceride. For example in one embodiment the co-solvent is benzyl alcohol. In at least one embodiment the salt is magnesium 2-((5Z,8Z,11Z,14Z,17Z)-icosa-5,8,11,14,17-pentaenyloxy)butanoate. In one embodiment the weight ratio of the polysorbate and the medium-chain triglyceride is about 3:2.

The above compositions according to the present disclosure are preconcentrates, and will form nano- or microemulsions in contact with aqueous media. Thus, in at least one embodiment the compositions/preconcentrates of the present disclosure described above are self-nanoemulsifying drug delivery systems (SNEDDS), self-microemulsifying drug delivery systems (SMEDDS), or self-emulsifying drug delivery systems (SEDDS).

The present disclosure is also directed to a self-microemulsifying drug delivery system (SMEDDS) comprising 2-((5Z,8Z,11Z,14Z,17Z)-icosa-5,8,11,14,17-pentaenyloxy) butanoic acid; a triglyceride; and a surfactant; wherein the composition forms an emulsion in an aqueous solution.

The present disclosure is also directed to a self-microemulsifying drug delivery system (SMEDDS) comprising 2-((5Z,8Z,11Z,14Z,17Z)-icosa-5,8,11,14,17-pentaenyloxy) butanoic acid; a triglyceride; a surfactant; and a co-solvent, wherein the composition forms an emulsion in an aqueous solution.

In one embodiment, a self-microemulsifying drug delivery system (SMEDDS) comprising a composition comprising 2-((5Z,8Z,11Z,14Z,17Z)-icosa-5,8,11,14,17-pentaenyloxy)butanoic acid; a triglyceride, such as an MCT oil; a surfactant, chosen from polysorbates; and a co-solvent, such as PEG-400, wherein the composition forms an emulsion in an aqueous solution is provided.

In one embodiment, a self-microemulsifying drug delivery system (SMEDDS) comprising 2-((5Z,8Z,11Z,14Z,17Z)-icosa-5,8,11,14,17-pentaenyloxy)butanoic acid; a triglyceride, such as an MCT oil; and a mixture of Tween 80, Tween 20 and Solutol HS15, wherein the composition forms an emulsion in an aqueous solution is provided.

In one embodiment, a self-microemulsifying drug delivery system (SMEDDS) comprising 2-((5Z,8Z,11Z,14Z,17Z)-icosa-5,8,11,14,17-pentaenyloxy)butanoic acid; a triglyceride, such as an MCT oil; a mixture of Tween 80 and Solutol HS15; and PEG 400, wherein the composition forms an emulsion in an aqueous solution is provided.

In one embodiment, a self-microemulsifying drug delivery system (SMEDDS) comprising 2-((5Z,8Z,11Z,14Z,17Z)-icosa-5,8,11,14,17-pentaenyloxy)butanoic acid; a triglyceride, such as an MCT oil; a mixture of Tween 20 and Solutol HS15; and PEG 400, wherein the composition forms an emulsion in an aqueous solution is provided.

In one embodiment, a self-microemulsifying drug delivery system (SMEDDS) comprising 2-((5Z,8Z,11Z,14Z,17Z)-icosa-5,8,11,14,17-pentaenyloxy)butanoic acid; an MCT oil; and Tween 80, wherein the composition forms an emulsion in an aqueous solution is provided.

In one embodiment, a self-microemulsifying drug delivery system (SMEDDS) comprising 2-((5Z,8Z,11Z,14Z,17Z)-icosa-5,8,11,14,17-pentaenyloxy)butanoic acid; an MCT oil; and Tween 20, wherein the composition forms an emulsion in an aqueous solution is provided.

In one embodiment, a self-microemulsifying drug delivery system (SMEDDS) comprising 40% by weight of 2-((5Z,8Z,11Z,14Z,17Z)-icosa-5,8,11,14,17-pentaenyloxy) butanoic acid; 30% by weight of an MCT oil; and 30% by weight of Tween 20, wherein the composition forms an emulsion in an aqueous solution is provided.

In one embodiment, a self-microemulsifying drug delivery system (SMEDDS) comprising 30% by weight of 2-((5Z,8Z,11Z,14Z,17Z)-icosa-5,8,11,14,17-pentaenyloxy) butanoic acid; 30% by weight of an MCT oil; and 40% by weight of Tween 20, wherein the composition forms an emulsion in an aqueous solution is provided.

In one embodiment, the composition comprises about 100 mg of 2-((5Z,8Z,11Z,14Z,17Z)-icosa-5,8,11,14,17-pentaenyloxy)butanoic acid, about 133 mg of Tween 20, about 100 mg of Miglyol 812N, and about 0.1 mg or 150-300 ppm butylated hydroxy anisole.

In one embodiment, a self-microemulsifying drug delivery system (SMEDDS) comprising about 100 mg of 2-((5Z,8Z,11Z,14Z,17Z)-icosa-5,8,11,14,17-pentaenyloxy)butanoic acid, about 133 mg of Tween 20, about 100 mg of Miglyol 812N, and about 0.1 mg or 150-300 ppm butylated hydroxy anisole, wherein the composition forms an emulsion in an aqueous solution is provided.

In one embodiment, the composition comprises about 50 mg of 2-((5Z,8Z,11Z,14Z,17Z)-icosa-5,8,11,14,17-pentaenyloxy)butanoic acid, about 162 mg of Tween 20, about 121 mg of Miglyol 812N, and about 0.1 mg or 150-300 ppm butylated hydroxy anisole.

In one embodiment, a self-microemulsifying drug delivery system (SMEDDS) comprising about 50 mg of 2-((5Z,8Z,11Z,14Z,17Z)-icosa-5,8,11,14,17-pentaenyloxy)butanoic acid, about 162 mg of polysorbate 20, about 121 mg of Miglyol 812N, and about 0.1 mg or 150-300 ppm butylated hydroxy anisole, wherein the composition forms an emulsion in an aqueous solution is provided.

A composition according to the present disclosure may improve the bioavailability of the API by significantly increasing the portal vein uptake and improving the pharmacokinetic properties, such as providing no gender differences, low individual variability and dose proportional exposure, and leading to enhanced benefit-risk properties of the API due to lower systemic exposure and thus reduced risk of systemic adverse events.

A composition comprising 30% by weight of 2-((5Z,8Z,11Z,14Z,17Z)-icosa-5,8,11,14,17-pentaenyloxy)butanoic acid; 30% by weight of Miglyol 812N; and 40% by weight of Tween 20 improved the systemic bioavailability of the API, as shown in the experimental section.

Surprisingly, as shown in the experimental section, a composition comprising 30% by weight of 2-((5Z,8Z,11Z,14Z,17Z)-icosa-5,8,11,14,17-pentaenyloxy)butanoic acid; 30% by weight of Miglyol 812N; and 40% by weight of Tween 20 enhanced the portal vein uptake of the API. Thereby possibly increasing the efficacy of the API without increasing in systemic exposure potentially leading to adverse events.

A composition comprising 30% by weight of 2-((5Z,8Z,11Z,14Z,17Z)-icosa-5,8,11,14,17-pentaenyloxy)butanoic acid; 30% by weight of Miglyol 812N; and 40% by weight of Tween 20 achieved food independent bioavailability of the API, as shown in the experimental section.

Surprisingly, as shown in the experimental section, a composition comprising 30% by weight of 2-((5Z,8Z,11Z,14Z,17Z)-icosa-5,8,11,14,17-pentaenyloxy)butanoic acid; 30% by weight of Miglyol 812N; and 40% by weight of Tween 20 provided very low individual pharmacokinetic variability of the API.

Furthermore, a composition comprising 30% by weight of 2-((5Z,8Z,11Z,14Z,17Z)-icosa-5,8,11,14,17-pentaenyloxy) butanoic acid; 30% by weight of Miglyol 812N; and 40% by weight of Tween 20 provided pharmacokinetic properties of the API that increased in a dose-proportional manner, as shown in the experimental section.

A composition comprising 30% by weight of 2-((5Z,8Z,11Z,14Z,17Z)-icosa-5,8,11,14,17-pentaenyloxy)butanoic acid; 30% by weight of Miglyol 812N; and 40% by weight of Tween 20 encapsulated in gelatin capsules shows stability within standard specification for more than 9 months.

The following examples are intended to illustrate the present disclosure without, however, being limiting in nature. It is understood that the skilled artisan will envision additional embodiments consistent with the disclosure provided herein.

EXAMPLES

General Procedures:

Different compositions were prepared as described in Tables 10-15. The active ingredient is 2-((5Z,8Z,11Z,14Z,17Z)-icosa-5,8,11,14,17-pentaenyloxy)butanoic acid. To prepare the compositions, the components were mixed according to the Tables identified below on a weight to weight basis. The compositions were visually inspected after mixing and again after being stored for 24 hours at room temperature. Under the Composition heading, a "clear" designation represents a transparent homogenous mixture; an "unclear" designation represents a nonhomogenous mixture, where some turbidity can be observed by visual inspection. The degree of turbidity was not determined.

All clear compositions were emulsified in the specified aqueous medium, by adding the aqueous medium (2 ml) to approximately 100 mg of the composition. The composition of the gastric media is shown in Table 8, and the composition of the intestinal media is shown in Table 9.

TABLE 8

| Composition of Gastric Media. Gastric Media | |
|---|---|
| Bile salts, Porcine (mM) | 0.08 |
| Lechitin (mM) | 0.02 |
| Sodium chloride (mM) | 34.2 |
| Pepsin (mg/ml) | 0.1 |
| pH | 1.6 (adjust with 1M HCl) |
| Osmolarity (mOsm/kg) | 120 |

TABLE 9

| Composition of Intestinal Media. Intestinal Media | |
|---|---|
| Bile salts, Porcine (mM) | 5 |
| Phospholipids, LIPOID S PC (mM) | 1.25 |

TABLE 9-continued

| Composition of Intestinal Media. Intestinal Media | |
|---|---|
| Trizma maleate (mM) | 2 |
| $Na^+$ (mM) | 150 |

The outcome of the emulsification was determined by visual inspection approximately 30 minutes after mixing. A majority of the compositions formed milky emulsions immediately after mixing. Emulsions that stayed milky and homogenous after 3 hours are described as "milky," under the Emulsion heading. Emulsions that separated or became nonhomogenous or where oil drops were observed are described as "separates," under the Emulsion heading.

Selected emulsions were further characterized by determining the particle size. Particle size was measured using a Malvern Zetasizer (Malvern Instrument, Worcestershire, UK) with particle size measuring range of 0.6-6000 nm and Zeta potential of particle range of 3 nm-10 μm.

The microemulsions formed can then be tested regarding distribution of API into the micellar, lipid and pellet fraction under lipolytic conditions. In Vitro lipolysis experiments was performed with a SMEDDS formulations, exemplified by formulation No. 27, in a biorelevant fasted state intestinal media. This SMEDDS formulation will increase the concentration of the compound in the micellar phase by more than 50%, compared to a standard oil formulation. Thus, this SMEDDS increases the rate and extent of amount available for absorption in an in-vivo situation.

Example 1: Compositions

Figure 2:
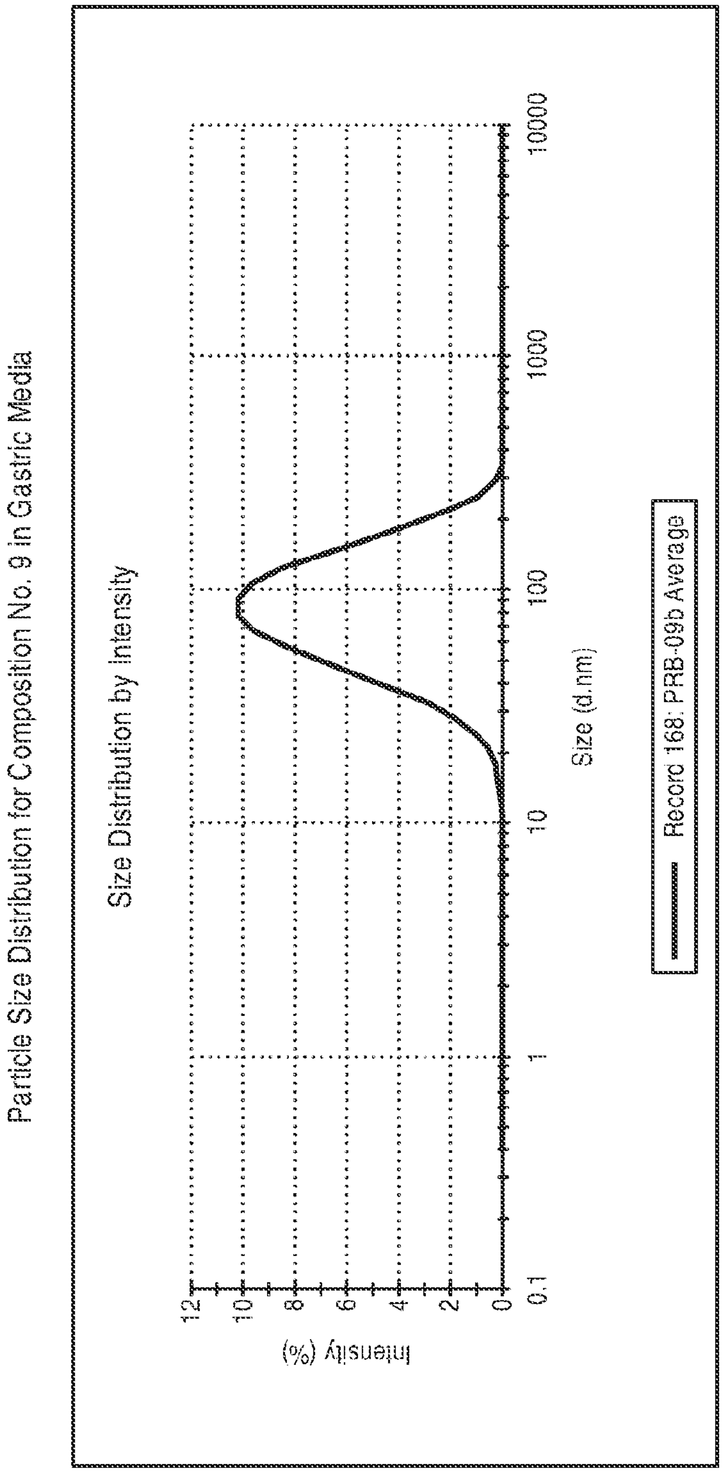
FIG. 2 shows particle size distributions for Composition Nos. 9, 14, 17 and 18.
Figure 2:
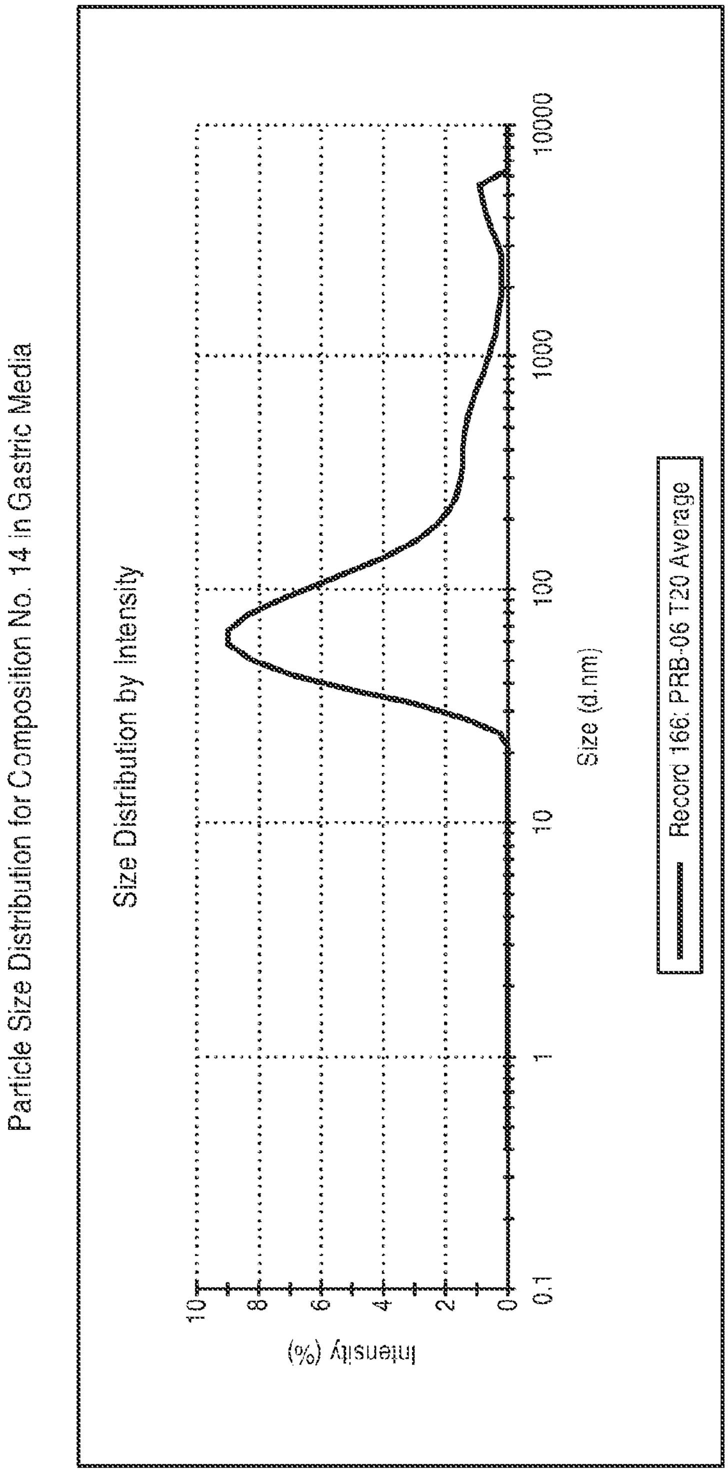
Figure 2:
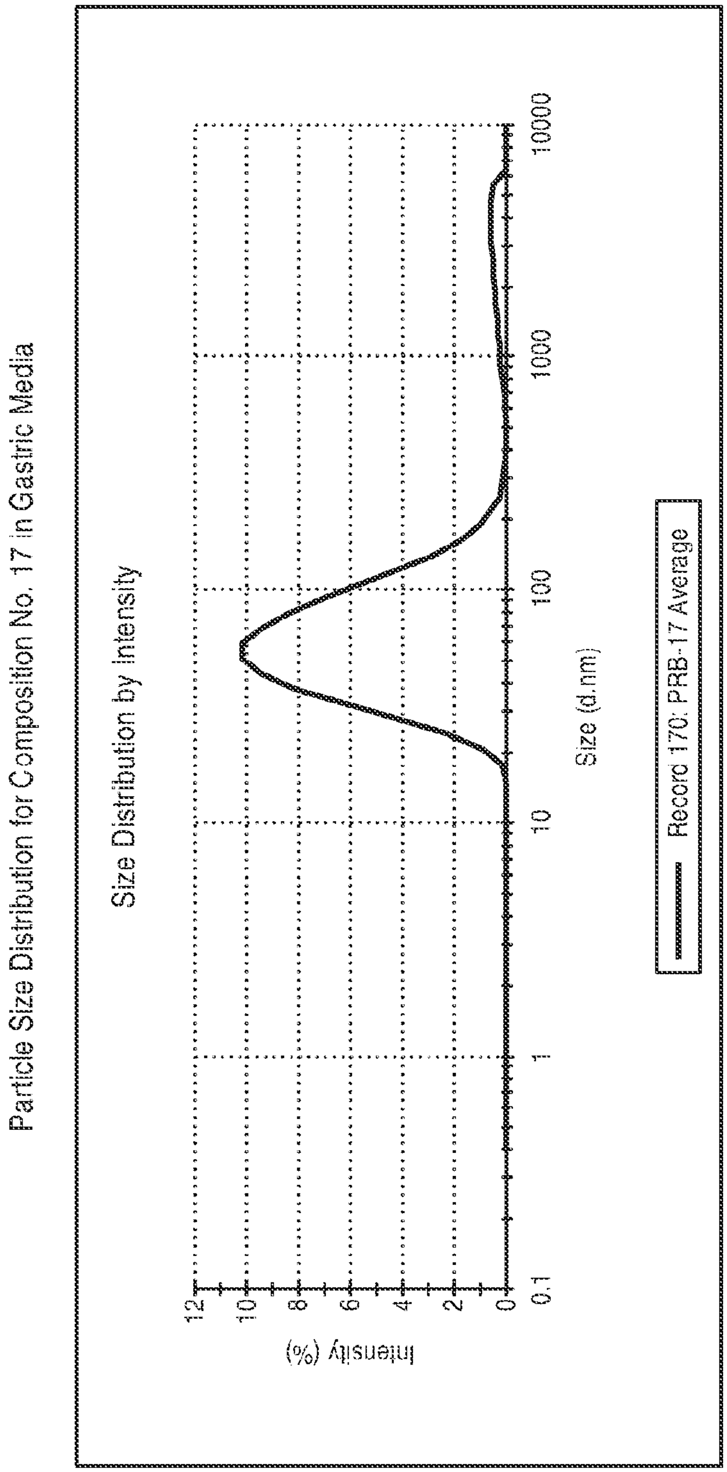
Figure 2:
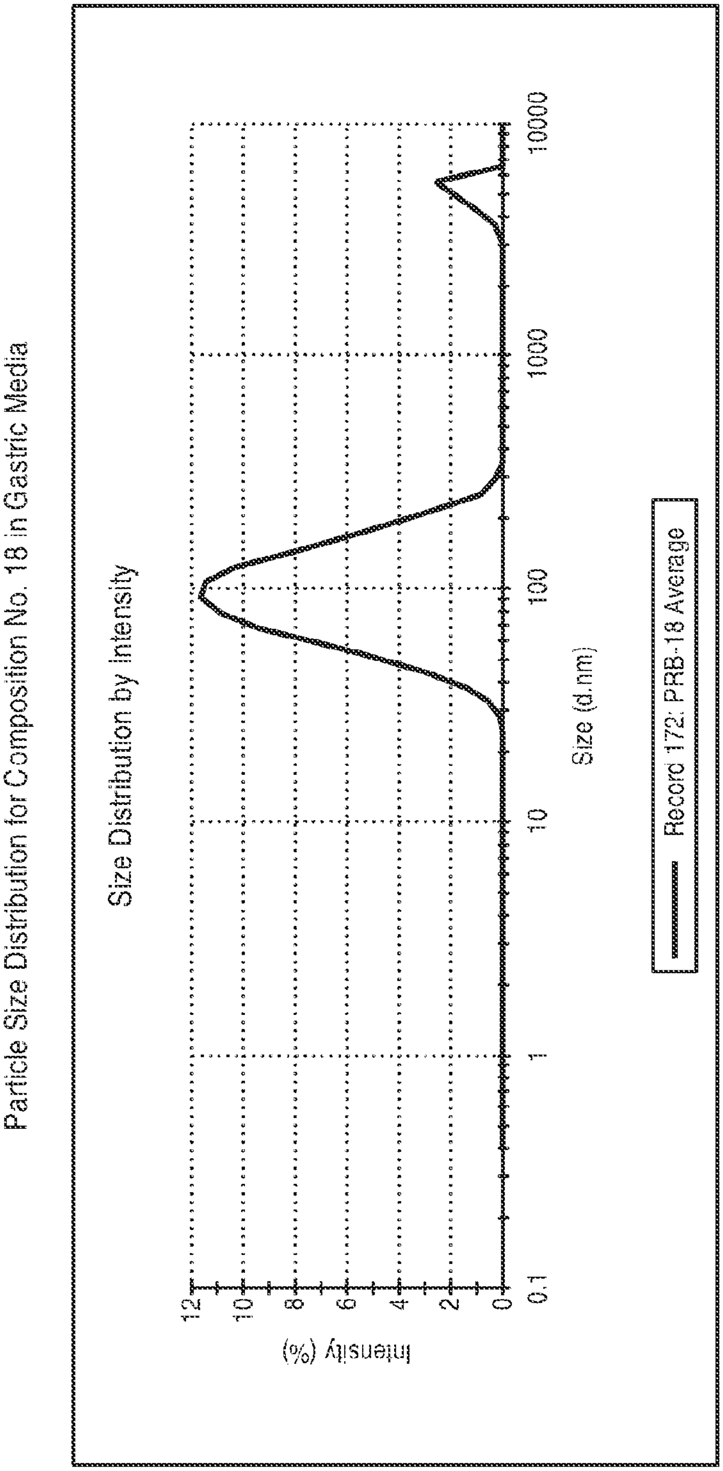
Figure 2:
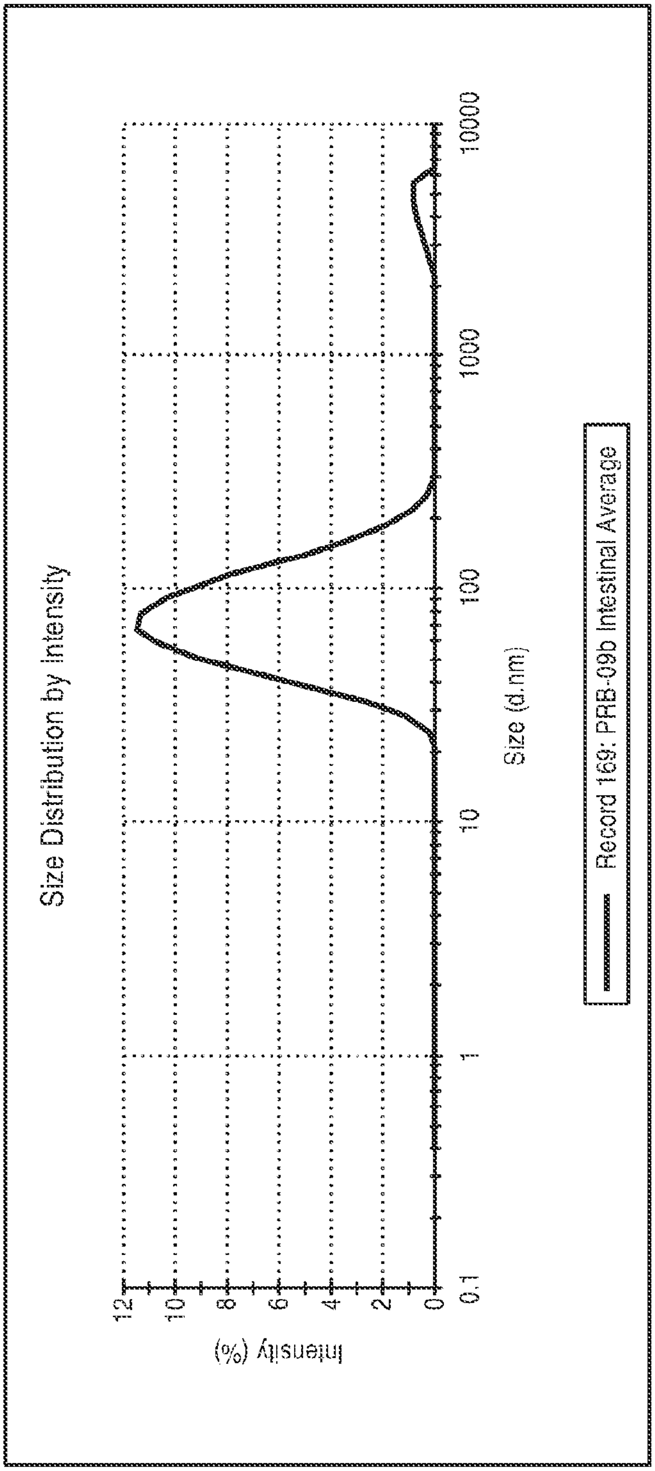
Figure 2:
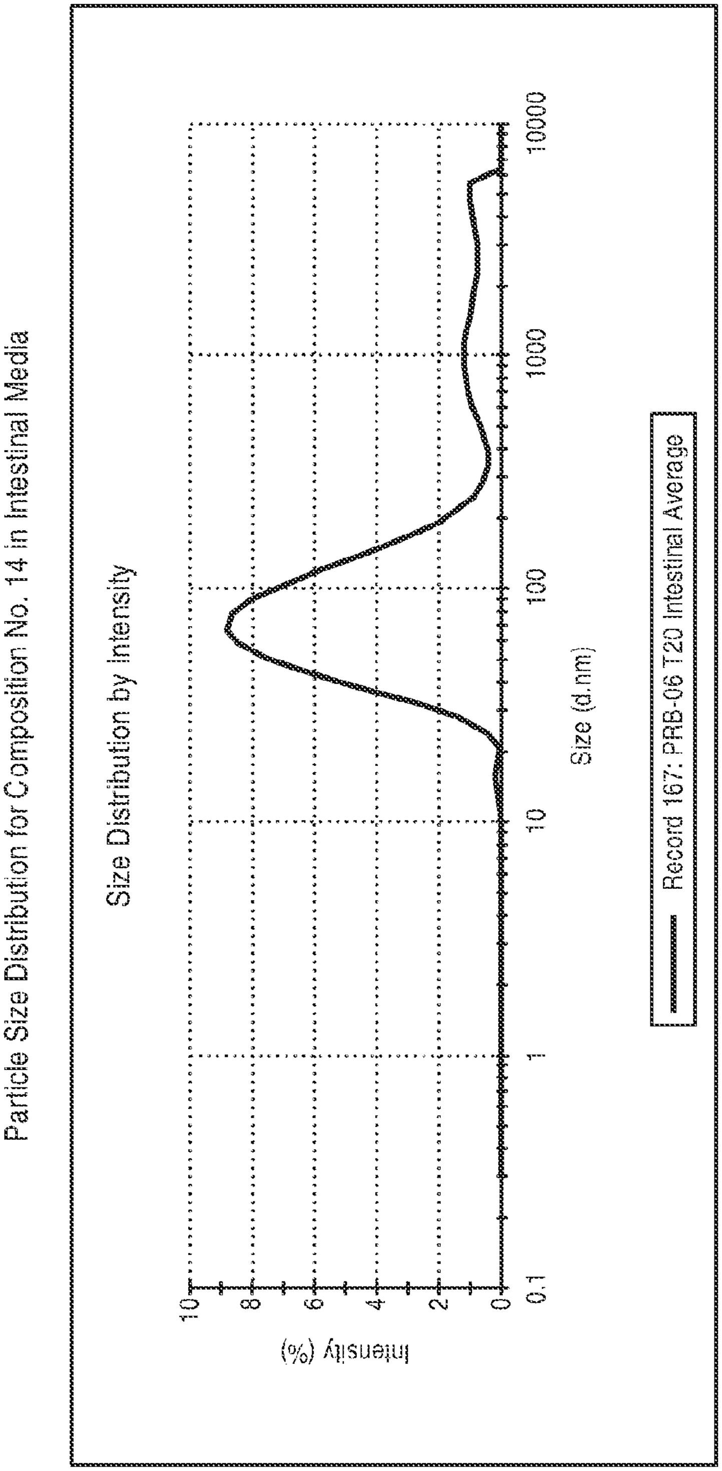
Figure 2:
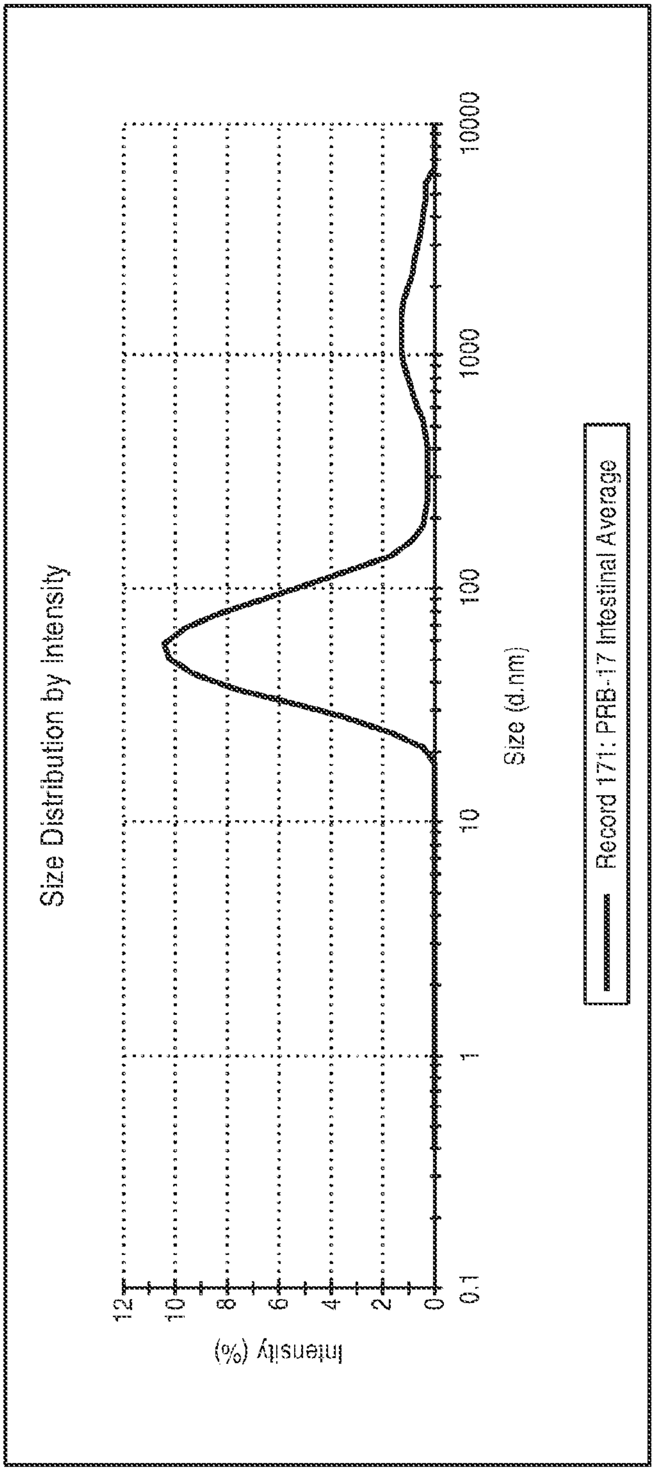
Figure 2:
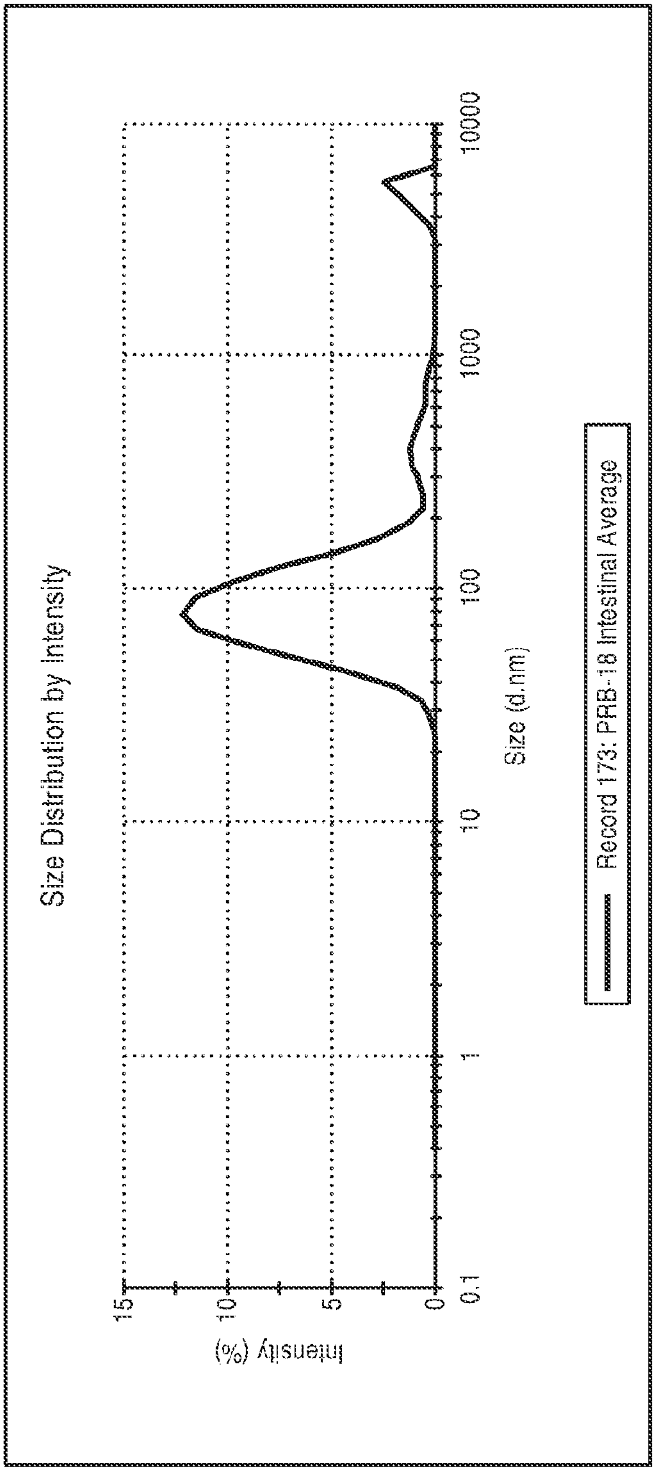
Figure 3:
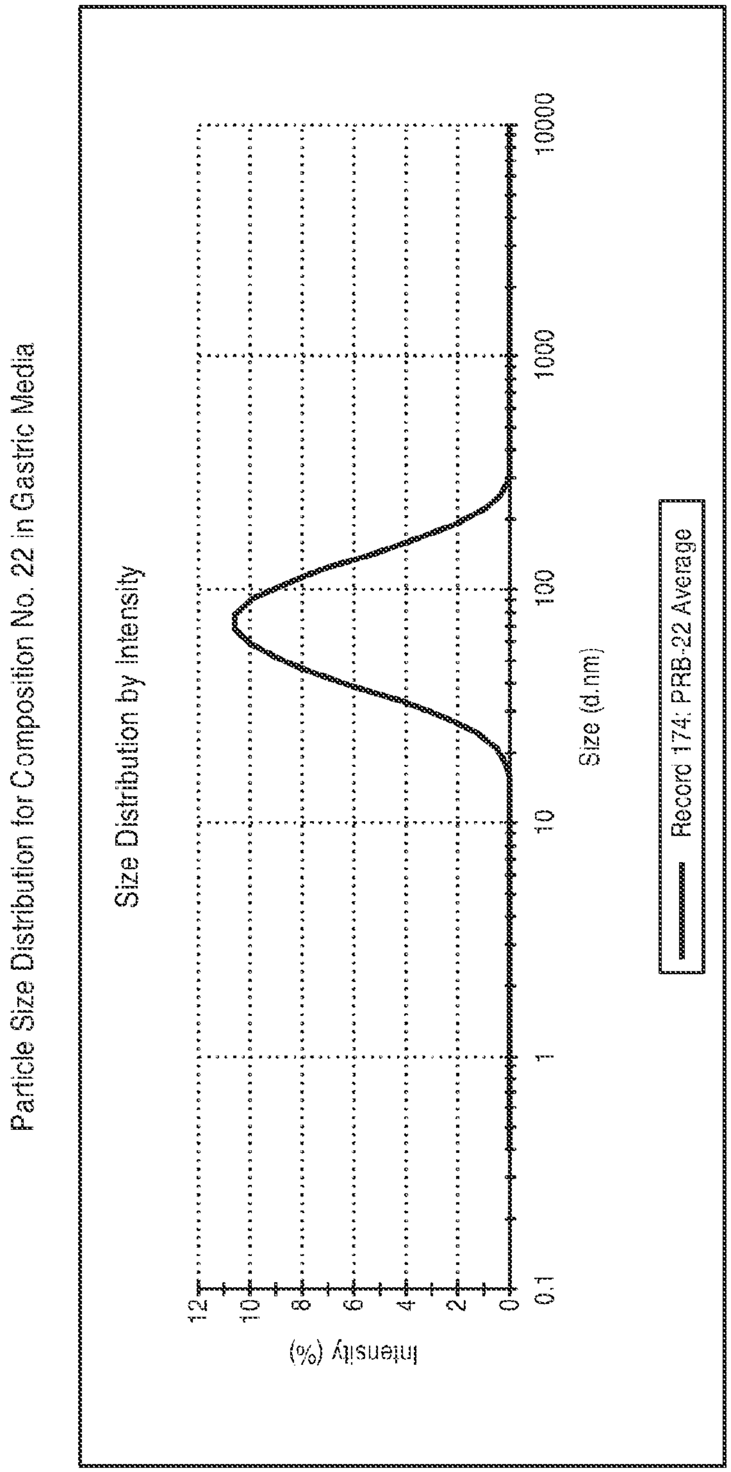
FIG. 3 shows particle size distributions for Composition Nos. 22-25 and 27.
Figure 3:
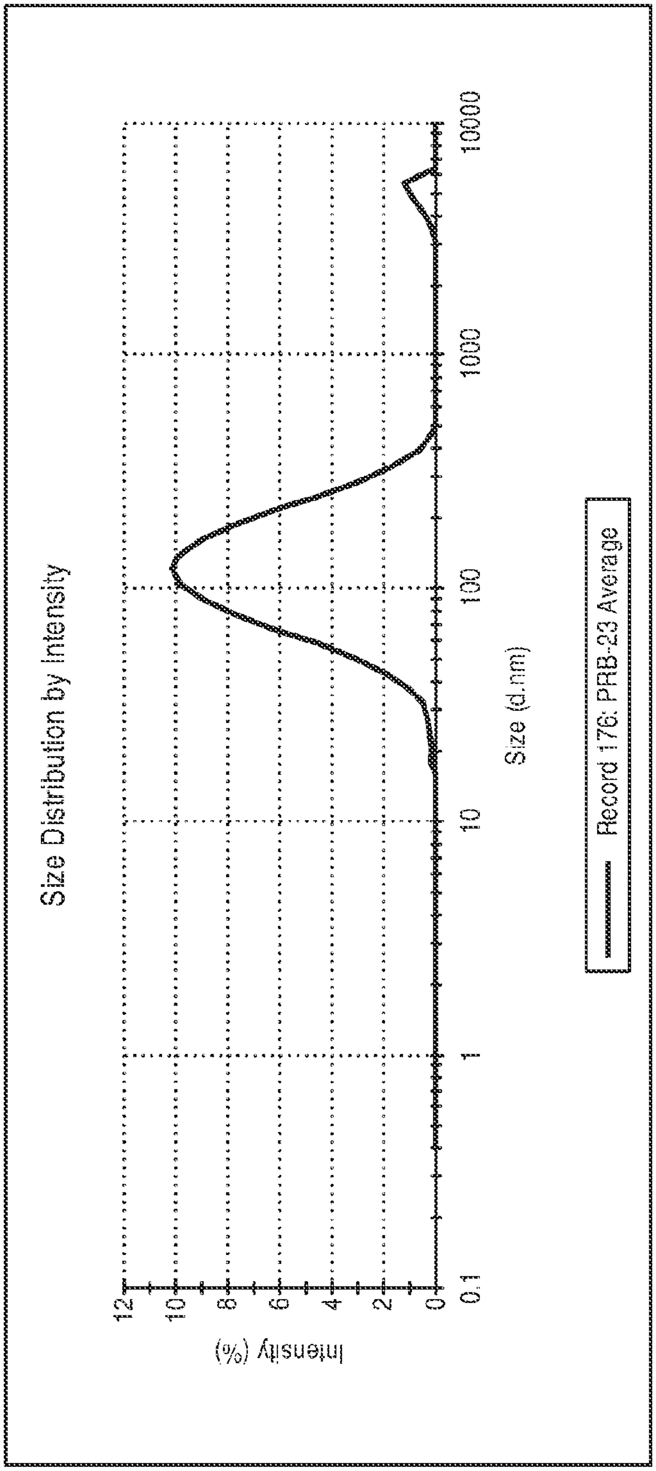
Figure 3:
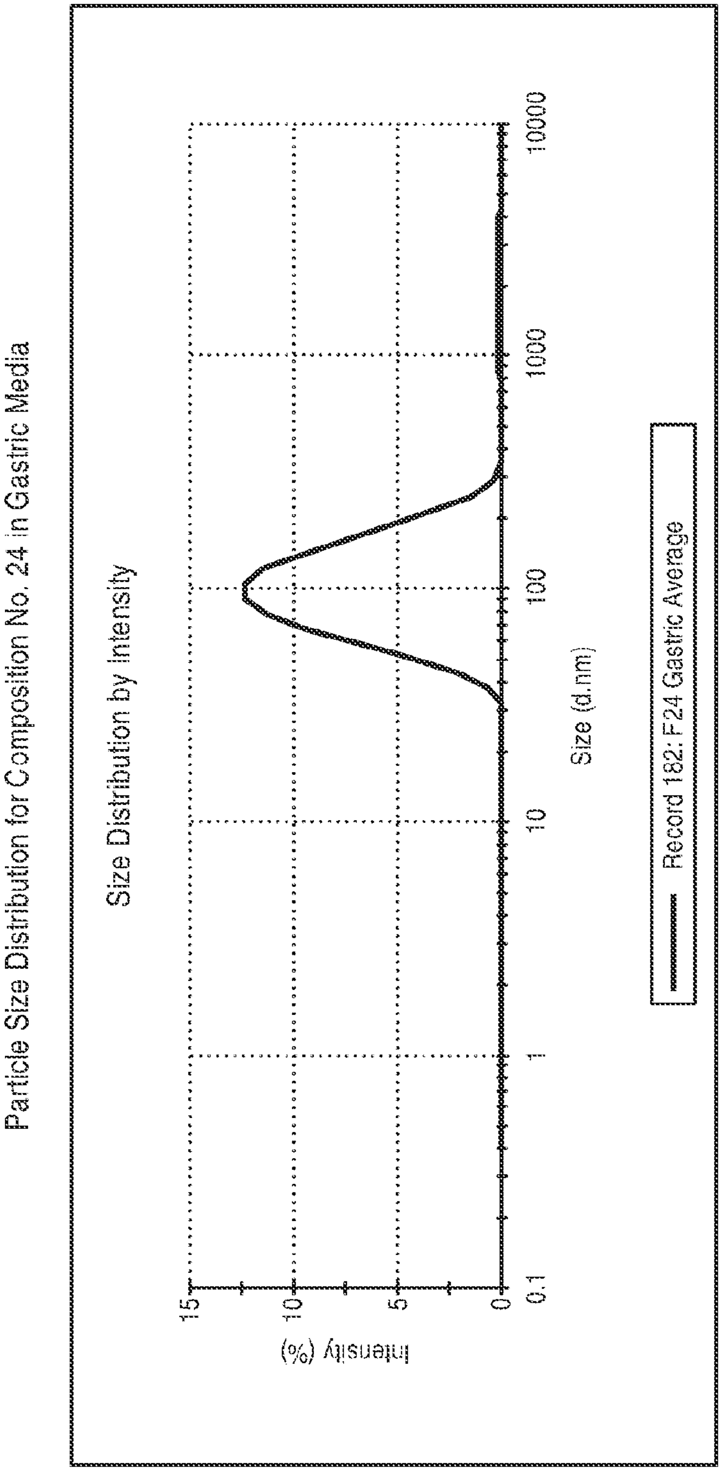
Figure 3:
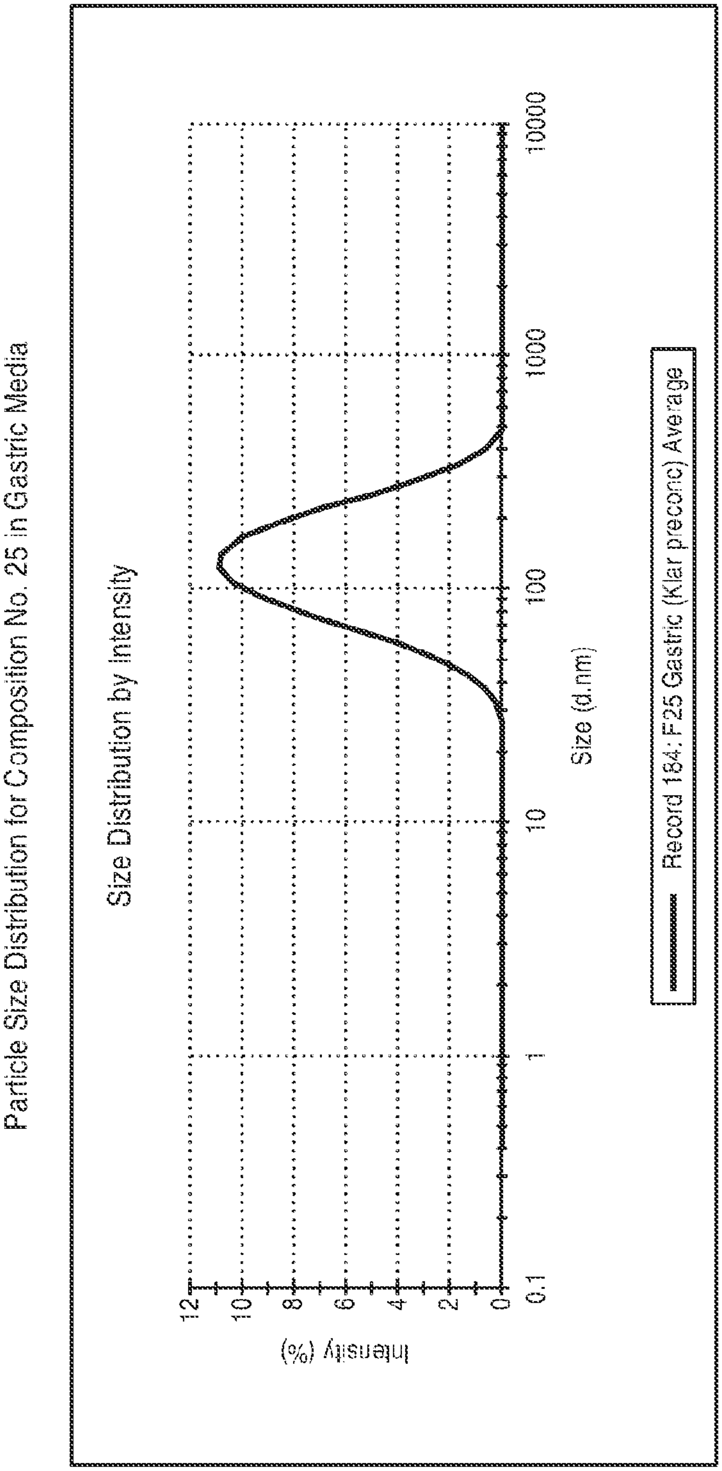
Figure 3:
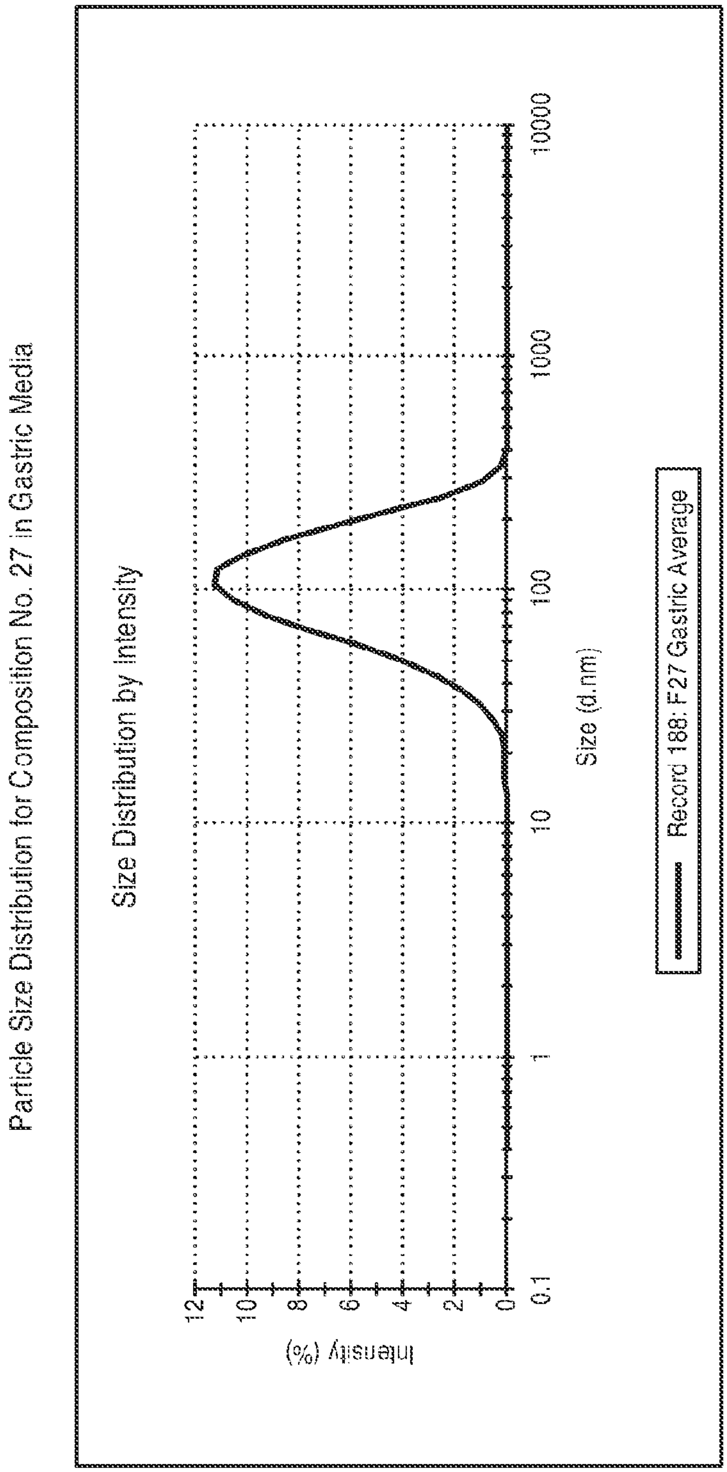
Figure 3:
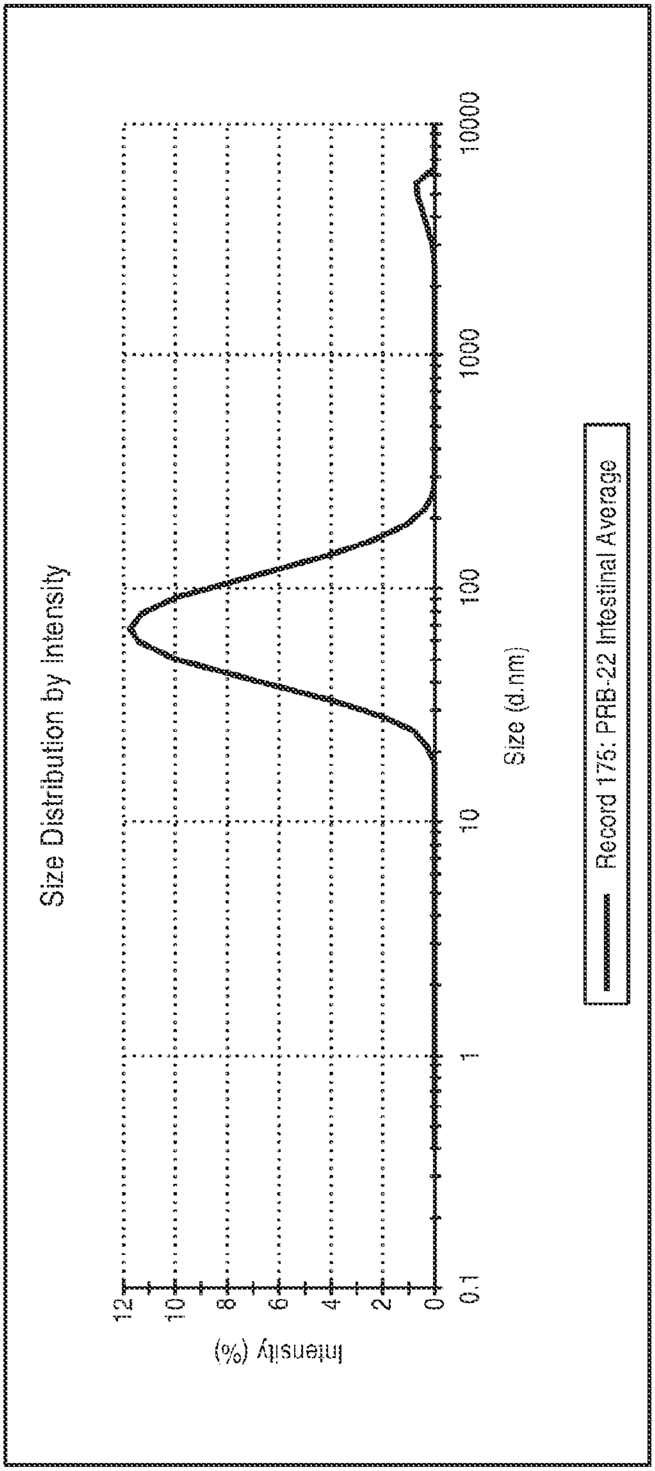
Figure 3:
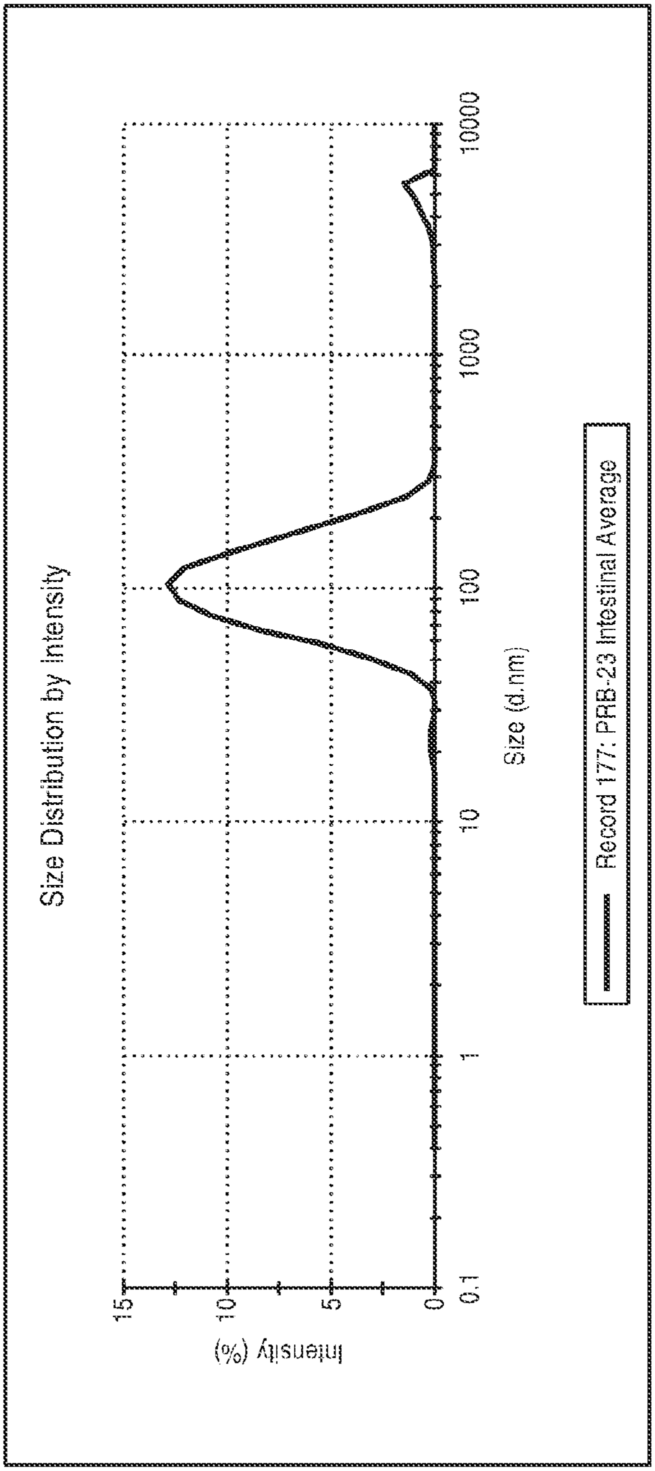
Figure 3:
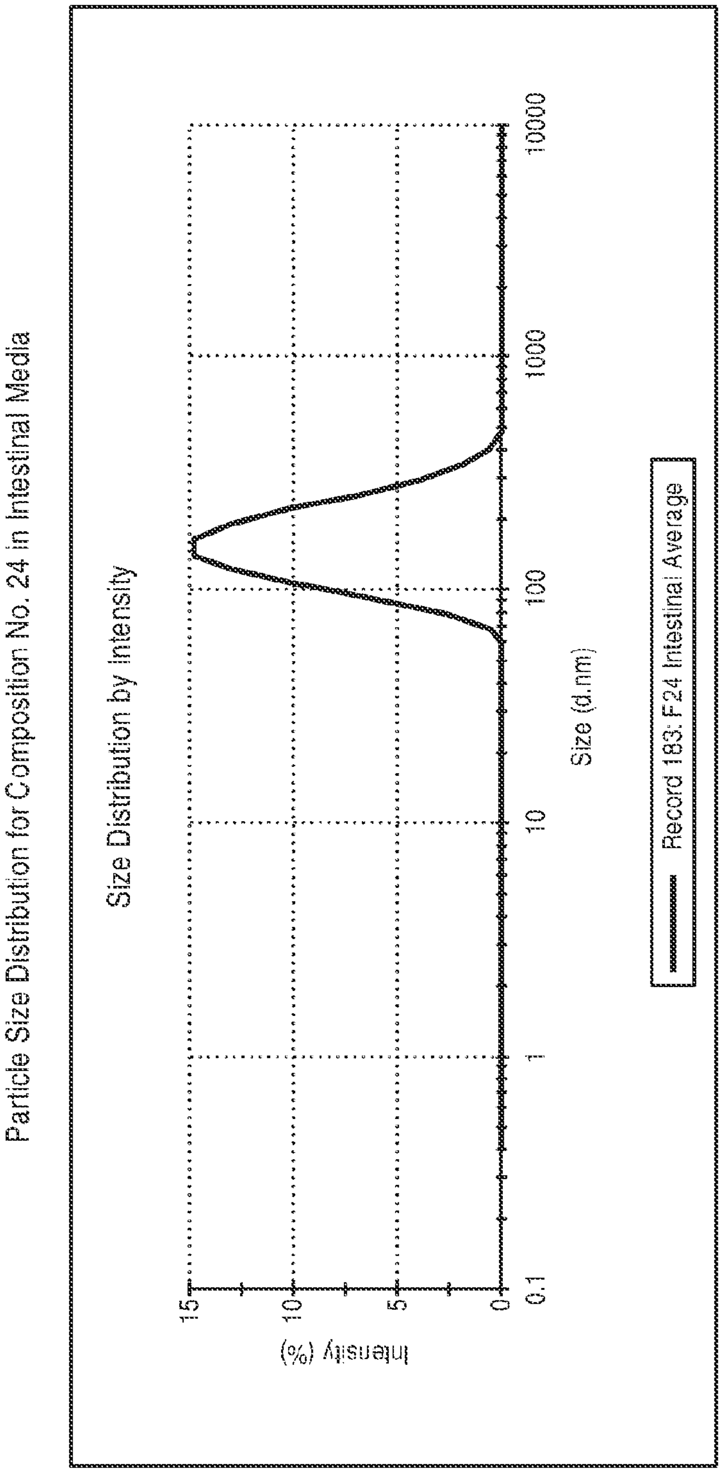
Figure 3:
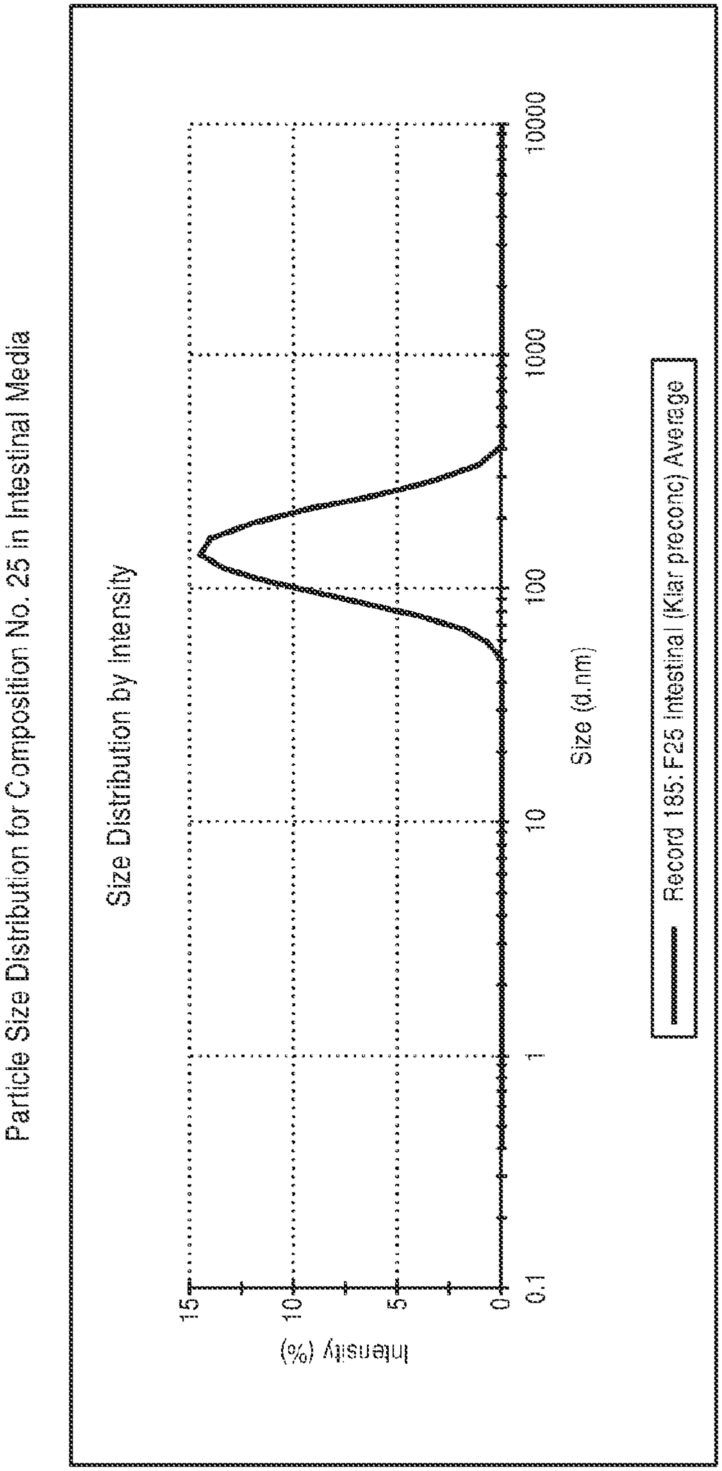
Figure 3:
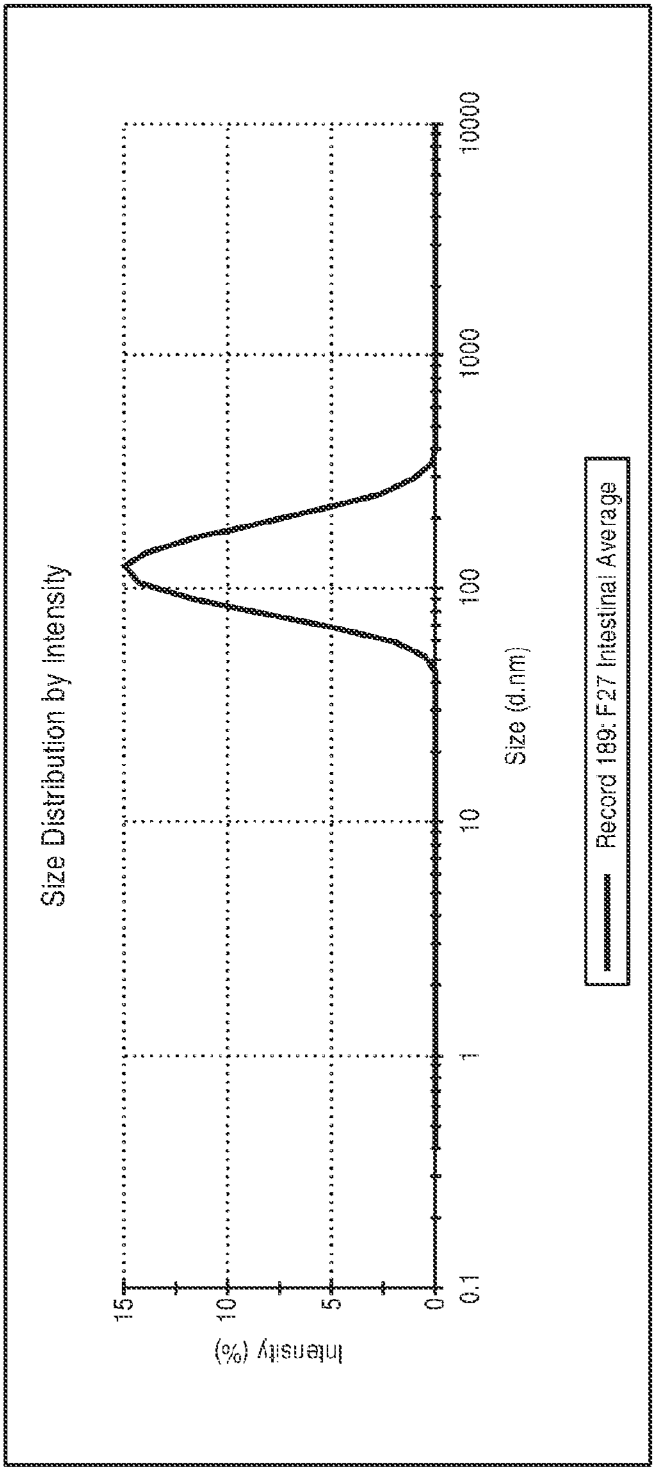

Compositions were prepared and emulsions were evaluated using the general procedures described above. Emulsions of Composition Nos. 1-28 were formed using water as the aqueous media. The results are given in Table 10 below. Emulsions of Composition Nos. 9, 14, 17, 18, 22, 23, 24, 25 and 27 were formed using both gastric media and intestinal media as the aqueous media (in separate experiments). Particle size distribution for Composition Nos. 1-8 in water is shown in FIG. 1. Particle size distribution for Composition Nos. 9, 14, 17 and 18 in gastric and intestinal media is shown in FIG. 2. Particle size distribution for Composition Nos. 22, 23, 24, 25 and 27 in gastric and intestinal media is shown in FIG. 3.

TABLE 10

Compositions and Emulsions

| No | Tween-20 (mg) | Tween-80 (mg) | Solutol HS 15 (mg) | Migly ol (mg) | PEG 400 (mg) | *Active ingredient (mg) | wt % act. ingr. | Pre-conc. | Emulsion Appearance In water |
|---|---|---|---|---|---|---|---|---|---|
| 1 | | 300 | 100 | 400 | 100 | 150 | 14.3 | Clear | Transparent, fully emulgated |
| 2 | | 300 | 100 | 400 | 100 | 300 | 25.0 | Clear | Transparent, some separation |
| 3 | | 300 | 100 | 400 | 100 | 400 | 30.8 | Clear | Milky, with little "cream on top" |
| 4 | | 300 | 100 | 400 | 50 | 350 | 29.2 | Clear | Milky/blueish, clear separation |
| 5 | | 300 | 100 | 400 | 0 | 400 | 33.3 | Clear | Milky, with little "cream on top" |
| 6 | | 300 | 100 | 350 | 0 | 300 | 28.6 | Clear | Transparent, fully emulgated |
| 7 | | 300 | 100 | 300 | 0 | 350 | 33.3 | Clear | Milky, with little "cream on top" |
| 8 | | 300 | 100 | 300 | 50 | 350 | 31.8 | Clear | Milky, with little "cream on top" |
| 9 | 300 | | 100 | 400 | 100 | 150 | 14.3 | Clear | Transparent, fully emulgated |
| 10 | 300 | | 100 | 400 | 100 | 300 | 25.0 | Clear | Milky, fully emulgated |
| 11 | 300 | | 100 | 400 | 100 | 400 | 30.8 | Clear | Milky, with little "cream on top" |
| 12 | 300 | | 100 | 400 | 50 | 350 | 29.2 | Clear | Milky, with little "cream on top" |
| 13 | 300 | | 100 | 400 | 0 | 400 | 33.3 | Clear | Milky, with little "cream on. top" |
| 14 | 300 | | 100 | 350 | 0 | 300 | 28.6 | Clear | Milky, clear separation |
| 15 | 300 | | 100 | 300 | 0 | 350 | 33.3 | Clear | Milky, with little "cream on top" |
| 16 | 300 | | 100 | 300 | 50 | 350 | 31.8 | Clear | Milky, clear separation |
| 17 | | 300 | 100 | 350 | 0 | 150 | 16.7 | Clear | Transparent, fully emulgated |
| 18 | | 300 | 100 | 350 | 0 | 250 | 25.0 | Clear | Whiteish/blueish/Transparent, fully emulgated |
| 19 | | 300 | 100 | 350 | 0 | 325 | 30.2 | Clear | Milky, with little "cream on top" |
| 20 | | 400 | 0 | 350 | 0 | 300 | 28.6 | Clear | Milky, with little "cream on top" |
| 21 | | 0 | 400 | 350 | 0 | 300 | 28.6 | Clear | Milky/blueish, clear separation |
| 22 | 300 | | 100 | 350 | 0 | 150 | 16.7 | Clear | Transparent, fully emulgated |
| 23 | 300 | | 100 | 350 | 0 | 250 | 25.0 | Clear | Milky/blueish, fully emulgated |
| 24 | 300 | | 100 | 350 | 0 | 325 | 30.2 | Clear | Milky, fully emulgated |
| 25 | 400 | | 0 | 350 | 0 | 300 | 28.6 | Clear | Milky, fully emulgated |
| 26 | 0 | | 400 | 350 | 0 | 300 | 28.6 | Clear | Blueish, clear separation |
| 27 | 400 | | 0 | 300 | 0 | 300 | 30.0 | Clear | Milky, fully emulgated |
| 28 | 400 | | 0 | 350 | 0 | 350 | 31.8 | Clear | Milky, with little "cream on top" |

*2-((5Z,8Z,11Z,14Z,17Z)-icosa-5,8,11,14,17-pentaenyloxy)butanoic acid

From a number of experiments it was possible to conclude that several compositions, e.g. Nos. 22-25 and 27, demonstrated that emulsion was formed quickly in water and their appearances in water indicated fully emulgated mixtures.

Example 2: Additional Compositions

Figure 4:
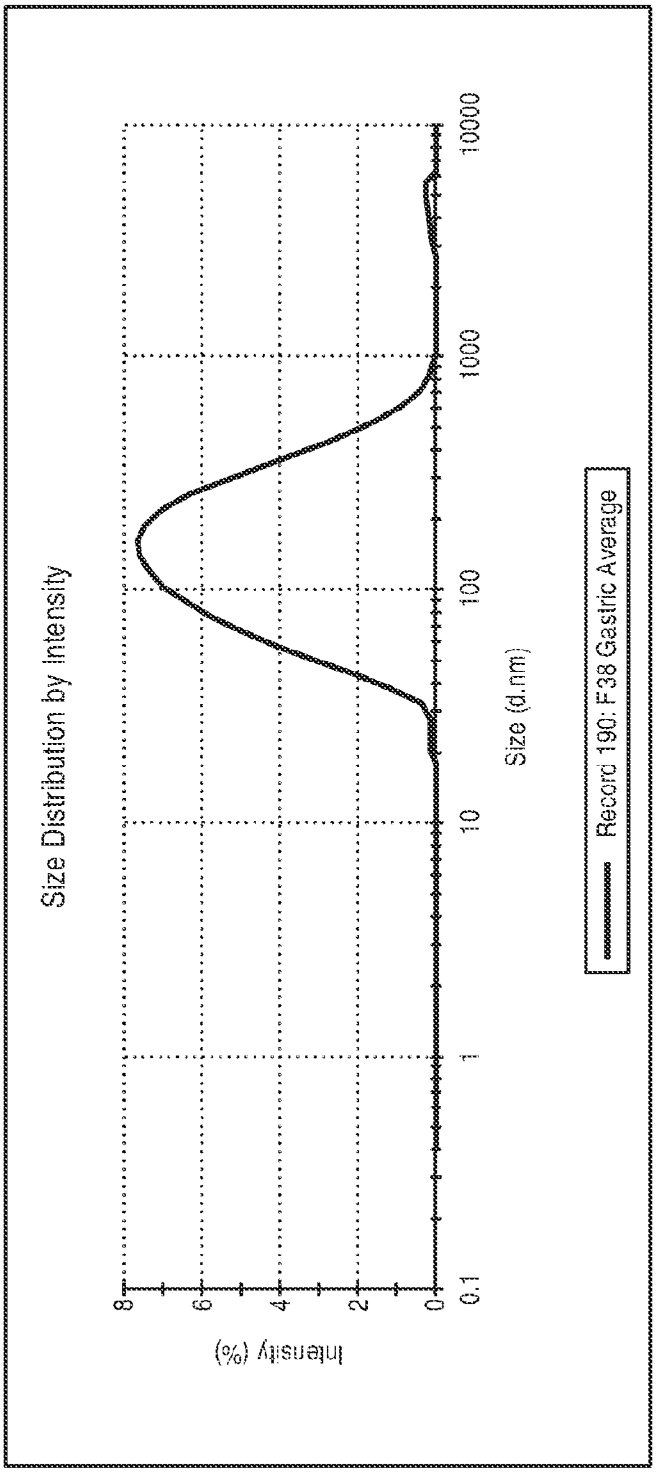
FIG. 4 shows particle size distributions for Composition Nos. 38 and 44.
Figure 4:
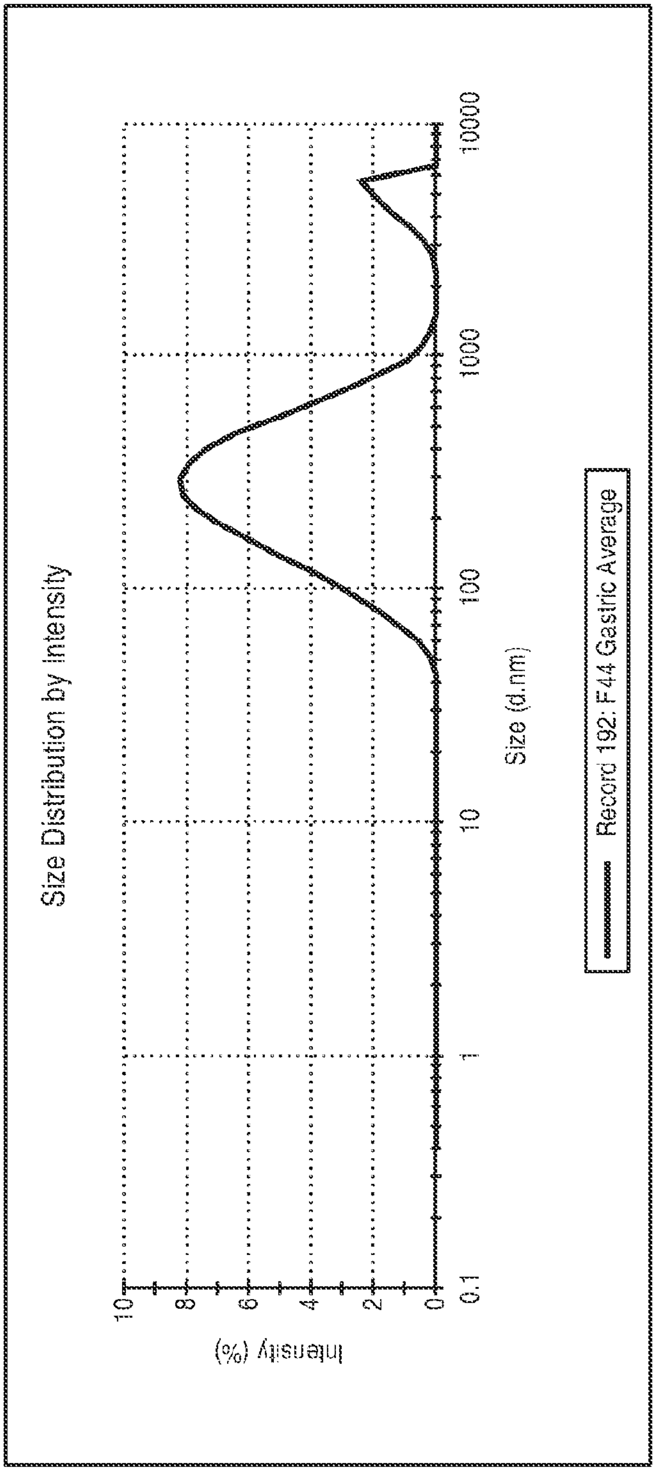
Figure 4:
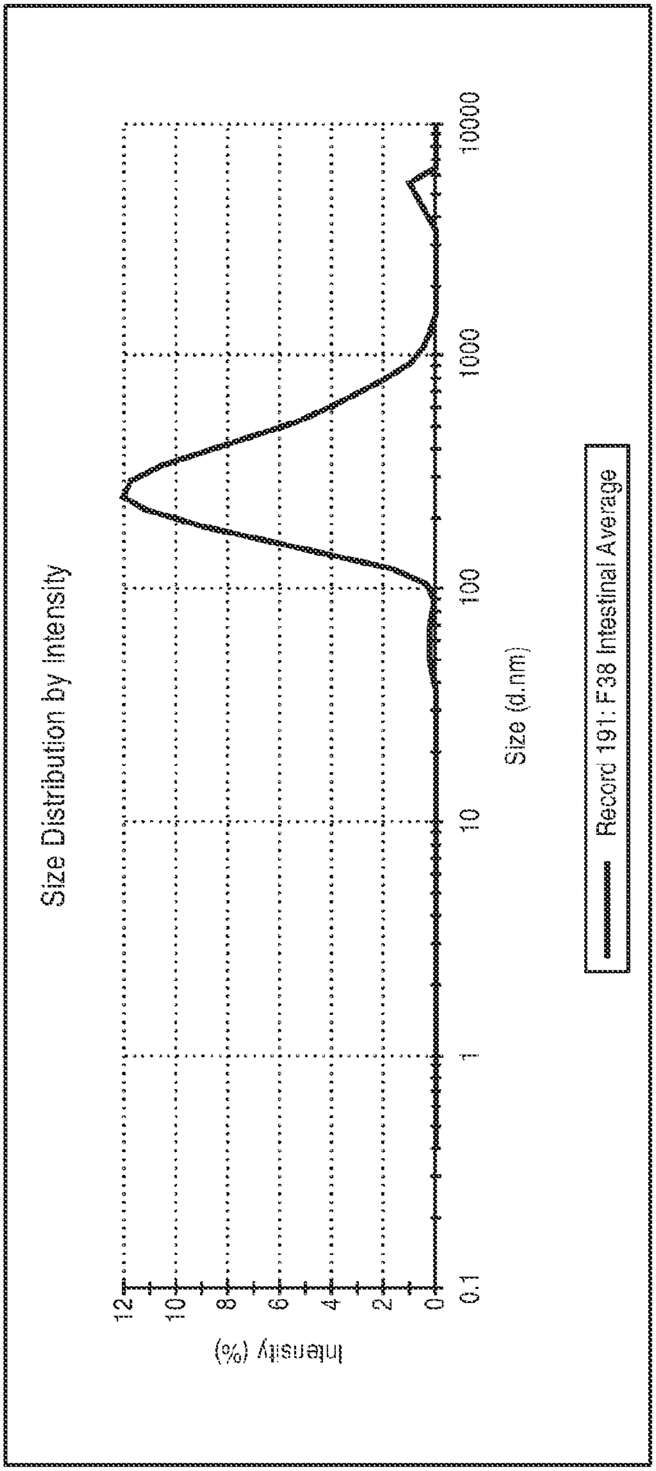
Figure 4:
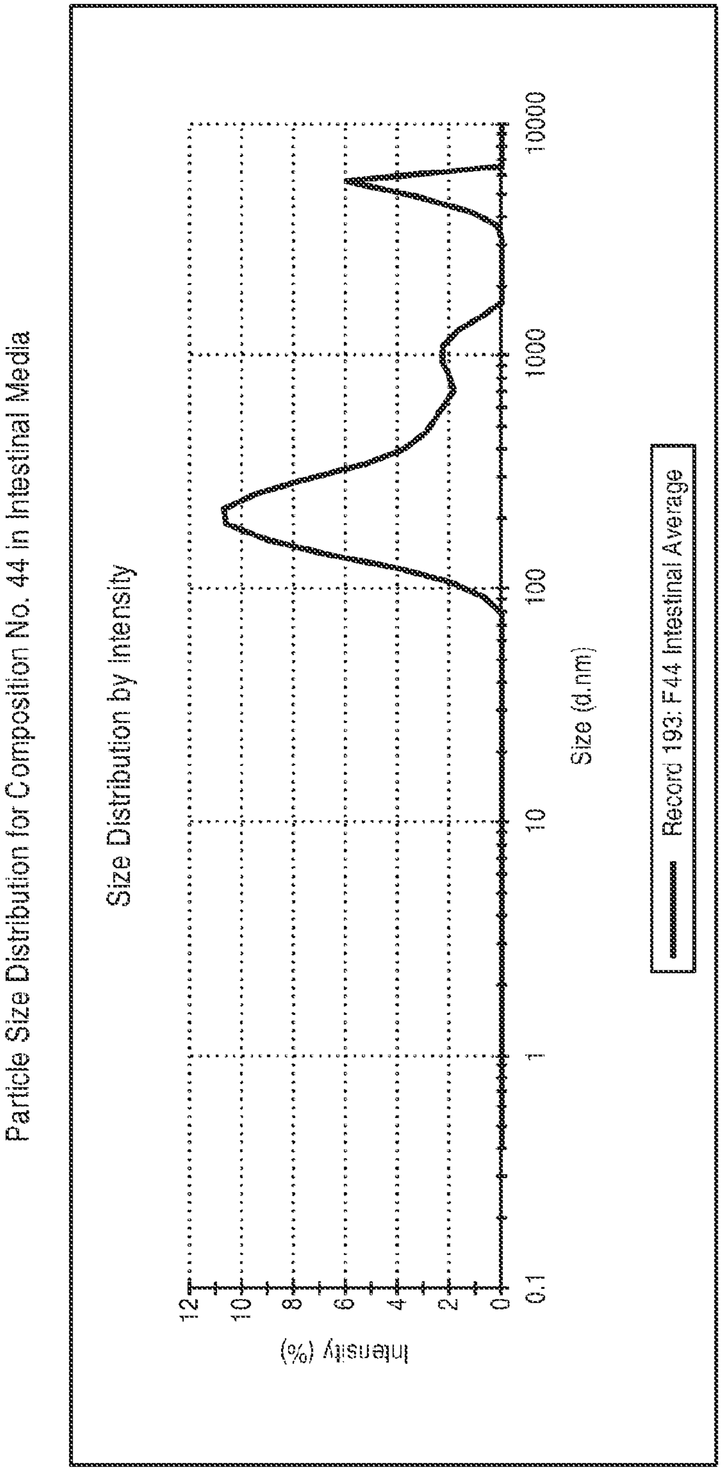

Compositions with different amounts of active ingredient (2-((5Z,8Z,11Z,14Z,17Z)-icosa-5,8,11,14,17-pentaenyloxy) butanoic acid), different types and amounts of triglycerides, and different types and amounts of surfactants were prepared as shown in Table 11. In Table 11 MCT means Miglyol 812 N, and SBO means soybean oil. Emulsions of Composition Nos. 38 and 44 were formed using both gastric media and intestinal media as the aqueous media (in separate experiments). Particle size distribution for Composition Nos. 38 and 44 is shown in FIG. 4. The scale given below was used to describe the observations.

1: Highly transparent nanoemulsion, with bluish tinge, stable. Particle size 10-50 nm.

2: Transparent nanoemulsion, with bluish tinge, stable. Particle size 50-100 nm.

3: Partly transparent emulsion, white, stable. Particle size 100-150 nm.

4: Partly transparent emulsion, white, minor separation and settlement of particles. Particle size 100-150 nm.

5: Partly transparent emulsion, white, medium separation and settlement of particles. Particle size 100-150 nm.

6: Partly transparent emulsion, white, major separation and settlement of particles. Particle size 100-150 nm.

7: Non-transparent emulsion, white emulsion, stable. Particle size >150 nm.

8: Non-transparent emulsion, white emulsion, minor separation and settlement of particles. Particle size >150 nM.

9: Non-transparent emulsion, white emulsion, medium separation and settlement of particles. Particle size >150 nM.

10: Non-transparent emulsion, white emulsion, major separation and settlement of particles. Particle size >150 nM.

11: No emulsion formed.

TABLE 11

Additional Compositions and Emulsions

| No. | Tween-20 (mg) | Tween-40 (mg) | Tween-60 (mg) | Tween-80 (mg) | Triglyceride (mg) | *Active ingredient (mg) | wt % act. ingr. | Pre-conc. | Emulsion In water appearance |
|---|---|---|---|---|---|---|---|---|---|
| | | | | | SBO | | | | |
| 32 | 400 | | | | 300 | 300 | 30.0 | Clear | 8 |
| 33 | 400 | | | | 350 | 300 | 28.6 | Clear | 8 |
| 34 | 400 | | | | 350 | 350 | 31.8 | Clear | 9 |
| | | | | | MCT | | | | |
| 27 | 400 | | | | 300 | 300 | 30.0 | Clear | 3 |
| 35 | 400 | | | | 275 | 300 | 30.8 | Clear | 4 |
| 36 | 400 | | | | 250 | 300 | 31.6 | Clear | 4 |
| 37 | 400 | | | | 275 | 325 | 32.5 | Clear | 4 |
| 38 | 400 | | | | 250 | 350 | 35.0 | Clear | 5 |
| | | | | | MCT | | | | |
| 39 | | 400 | | | 300 | 300 | 30.0 | Clear | 5 |
| 40 | | | 400 | | 300 | 300 | 30.0 | Clear | 5 |
| 41 | | | | 400 | 300 | 300 | 30.0 | Clear | 5 |
| | | | | | SBO | | | | |
| 42 | | 400 | | | 300 | 300 | 30.0 | Clear | 8 |
| 43 | | | 400 | | 300 | 300 | 30.0 | Clear | 8 |
| 44 | | | | 400 | 300 | 300 | 30.0 | Clear | 8 |

| No. | Surfactant (mg) | Tween-80 (mg) | Triglyceride (mg) | *Active ingredient (mg) | wt % act. ingr. | Pre-conc. | Emulsion In water appearance |
|---|---|---|---|---|---|---|---|
| | Brij '97 | | MCT | | | | |
| 48 | 400 | | 300 | 300 | 30.0 | Clear | 9 |
| | | | SBO | | | | |
| 50 | 400 | | 300 | 300 | 30.0 | Clear | 8 |
| | Chremophor EL | | | | | | |
| 52 | 400 | | 300 | 300 | 30.0 | Clear | 10 |
| | Span80 | | | | | | |
| 53 | 400 | | 300 | 300 | 30.0 | NH | 11 |
| | Triacetin | | | | | | |
| 54 | 300 | 200 | 200 | 300 | 30.0 | Clear | 11 |
| 55 | 400 | 200 | | 400 | 40.0 | Clear | 11 |

*2-((5Z,8Z,11Z,14Z,17Z)-icosa-5,8,11,14,17-pentaenyloxy)butanoic acid

Based upon these additional experiments it was possible to conclude that a number of compositions, e.g. Nos. 35-41 as well as No 27, could be used to form fully emulgated emulsions in water with particle size less than 150 nm. All of these compositions contained at least 30% active ingredient.

Example 3: Compatibility of Compositions with Co-Solvents

The compatibility of Composition No. 27 with co-solvents was examined. Co-solvent (50 mg) was added to pre-concentrate (950 mg), prepared from a solution of Tween-20 (3 g), MCT (2.2 g), and active ingredient (2-((5Z, 8Z,11Z,14Z,17Z)-icosa-5,8,11,14,17-pentaenyloxy)butanoic acid, 2.4 g). The results from this compatibility study are shown in Table 12. The composition is compatible with a wide range of co-solvents. The high content of the active ingredient allows the addition of hydrophilic co-solvents into this composition. The dispersion rate indicates the rate of occurrence of a mixture and/or an emulsion. The following scale was used: 1=fast, 2=medium, 3=slow.

TABLE 12

Co-solvent Compatibility Studies

| No. | Co-solvent | Pre-concentrate | Dispersion rate | Appearance In water |
|---|---|---|---|---|
| 56 | Ethanol | homogeneous | 1 | Milky as 27 |
| 57 | Triacetine | homogeneous | 2 | Milky as 27 |
| 58 | Tetraglycol | homogeneous | 2 | More transparent than 27 |
| 59 | Solutol HS15 | homogeneous | 3 | Milky as 27 |
| 60 | PEG 400 | homogeneous | 3 | Milky as 27 |
| 61 | Benzylalcohol | homogeneous | 3 | Milky as 27 |

Figure 5:
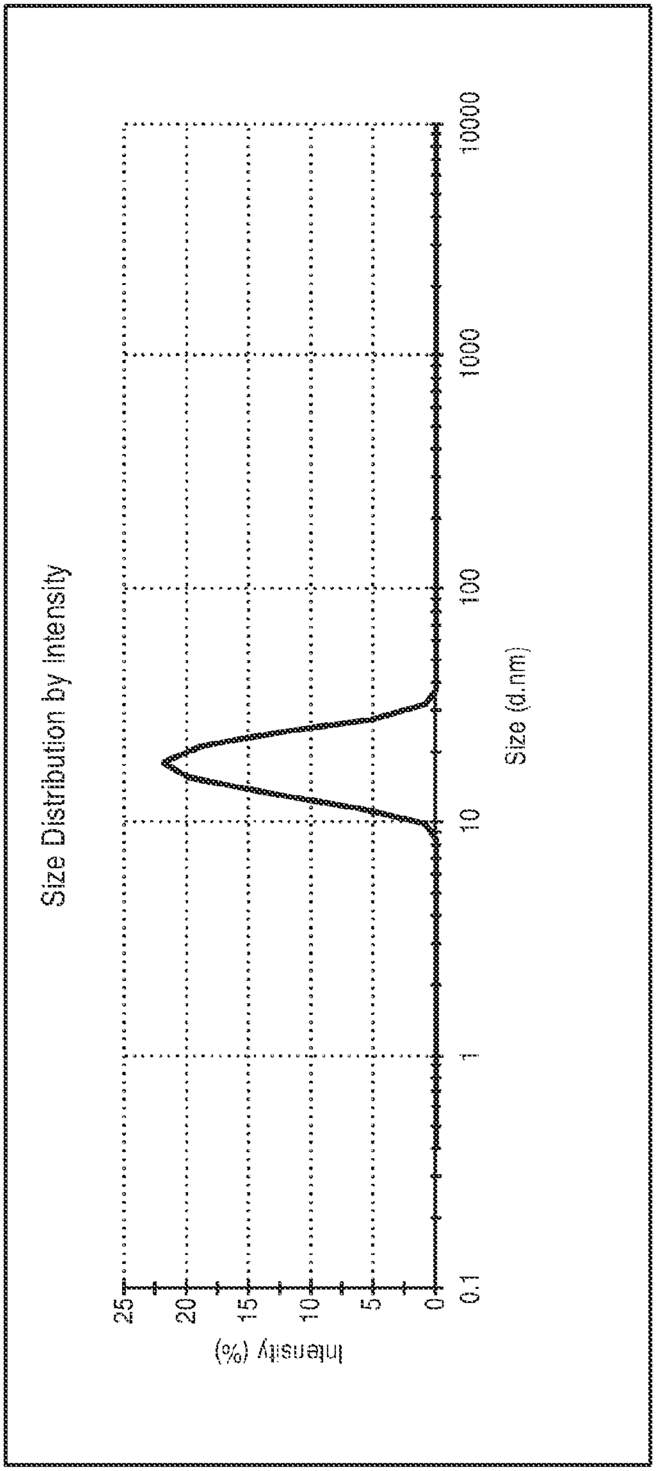
FIG. 5 shows particle size distributions for Composition Nos. 73-77.
Figure 5:
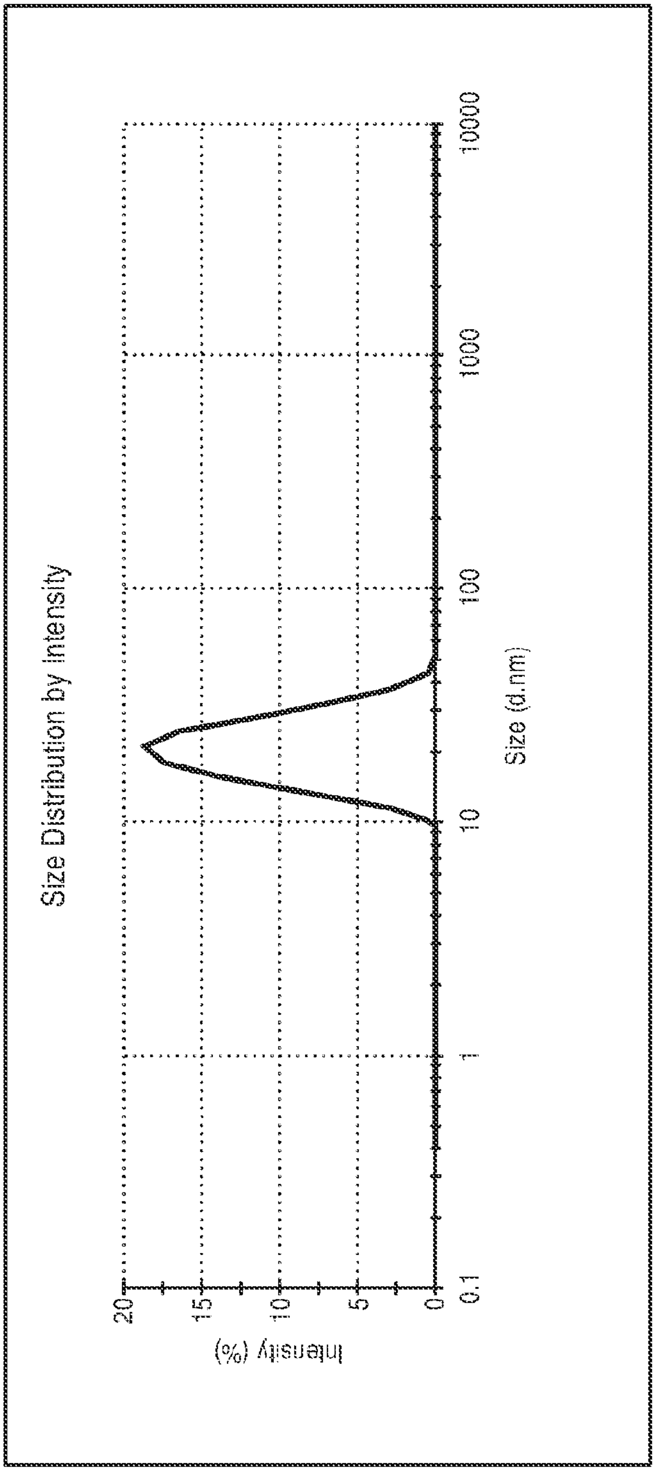
Figure 5:
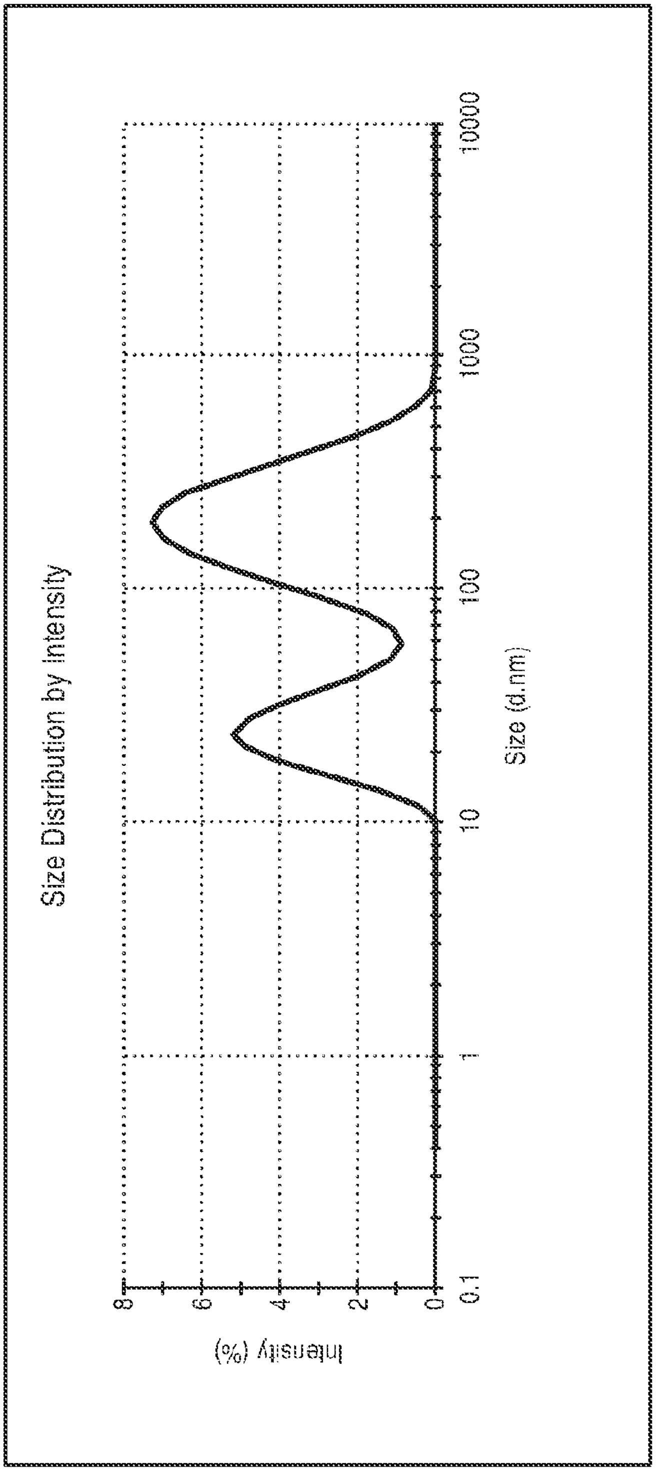
Figure 5:
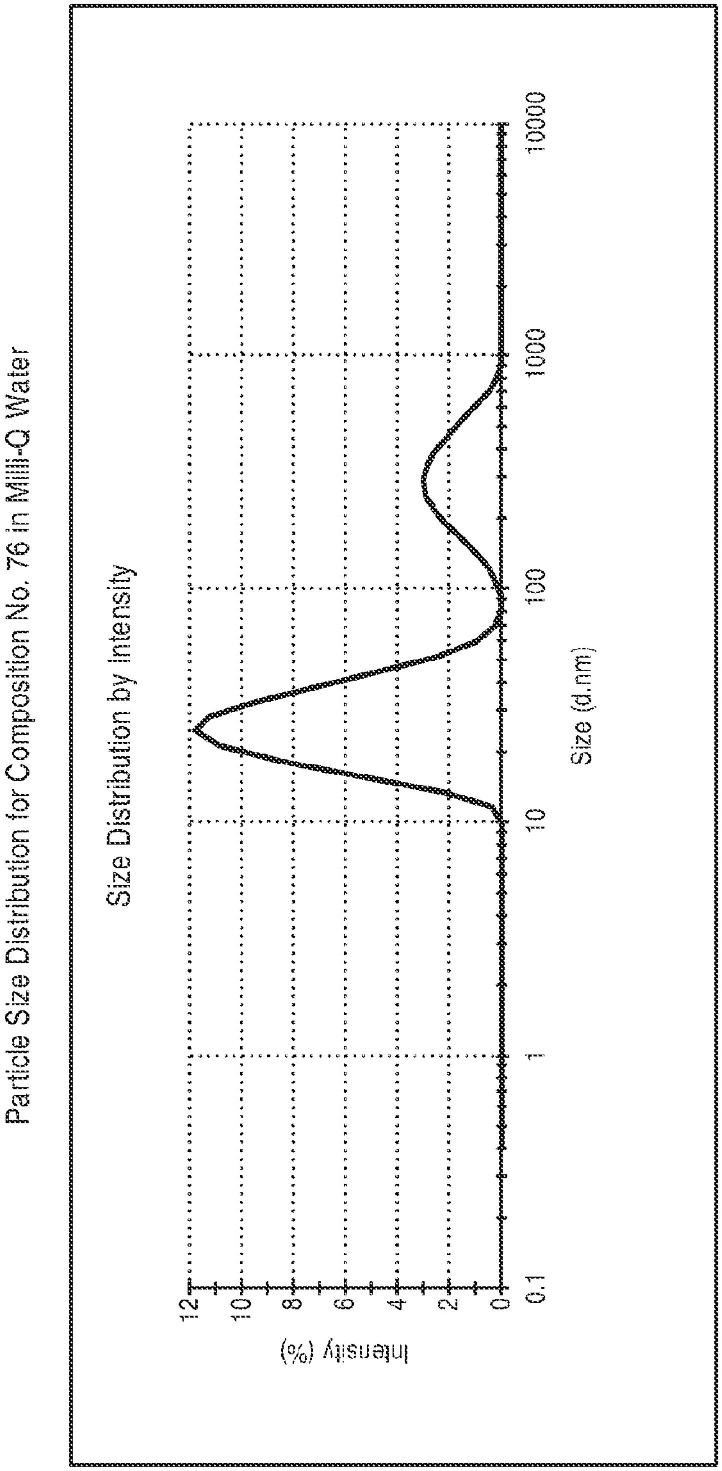
Figure 5:
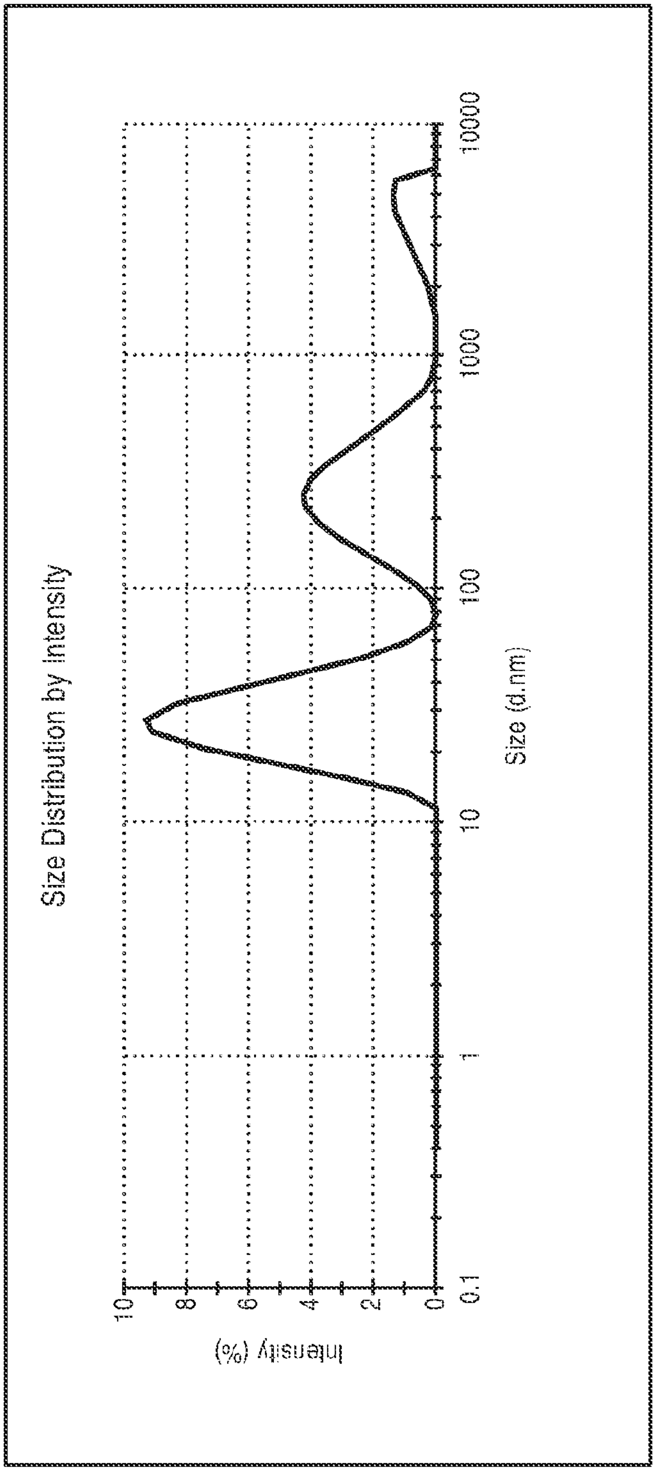
Figure 6:
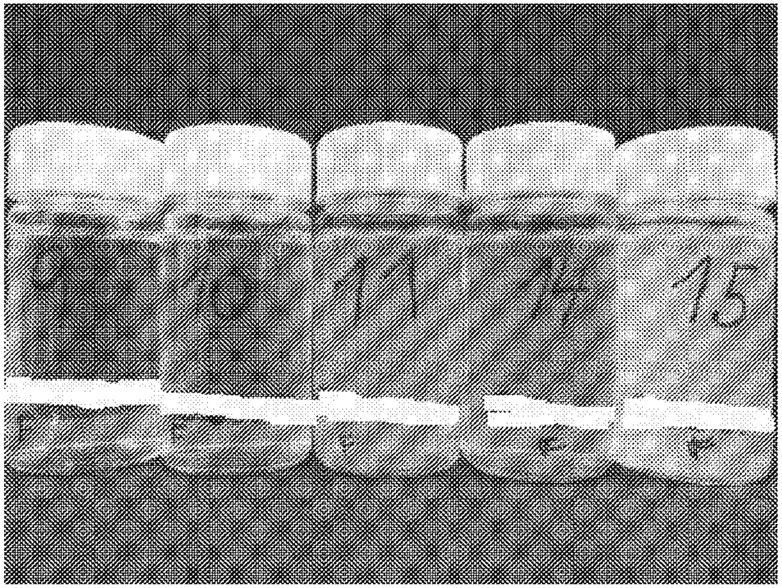
FIG. 6 shows emulsions formed for Composition Nos. 73-77.

Example 4: Additional Compositions with Varied Amounts of MCT and Active Ingredient Additional compositions were prepared with Tween-20, Tween-80, Solutol HS 15, and varied amounts of MCT oil (Miglyol 812N) and active ingredient (2-((5Z,8Z,11Z,14Z,17Z)-icosa-5,8,11,14,17-pentaenyloxy)butanoic acid). Emulsions of Composition Nos. 73-77 were formed using water as the aqueous medium. Results are shown in Table 13 and FIGS. 5 and 6.

TABLE 13

Additional Compositions and Emulsions

| No. | Tween-20 (mg) | Tween-80 (mg) | Solutol HS 15 (mg) | MCT oil (mg) | Active ingredient (mg) | % act. ingr. | Pre. Conc | Emulsion appearance In water |
|---|---|---|---|---|---|---|---|---|
| 73 | 300 | 100 | 400 | 100 | 150 | 14.3 | Clear | (Vial 9) Highly transparent, fully emulgated |
| 74 | 300 | 100 | 400 | 100 | 200 | 19.1 | Clear | (Vial 10) Highly transparent, fully emulgated |
| 75 | 300 | 100 | 400 | 100 | 250 | 21.7 | Clear | (Vial 11) Translucent/milky, fully emulgated |
| 76 | 300 | 100 | 400 | 150 | 250 | 20.8 | Clear | (Vial 14) Translucent/milky, fully emulgated |
| 77 | 300 | 100 | 400 | 175 | 275 | 22 | Clear | (Vial 15) Translucent/milky, fully emulgated |

Example 5: Substitution of LCT for MCT

Figure 7:
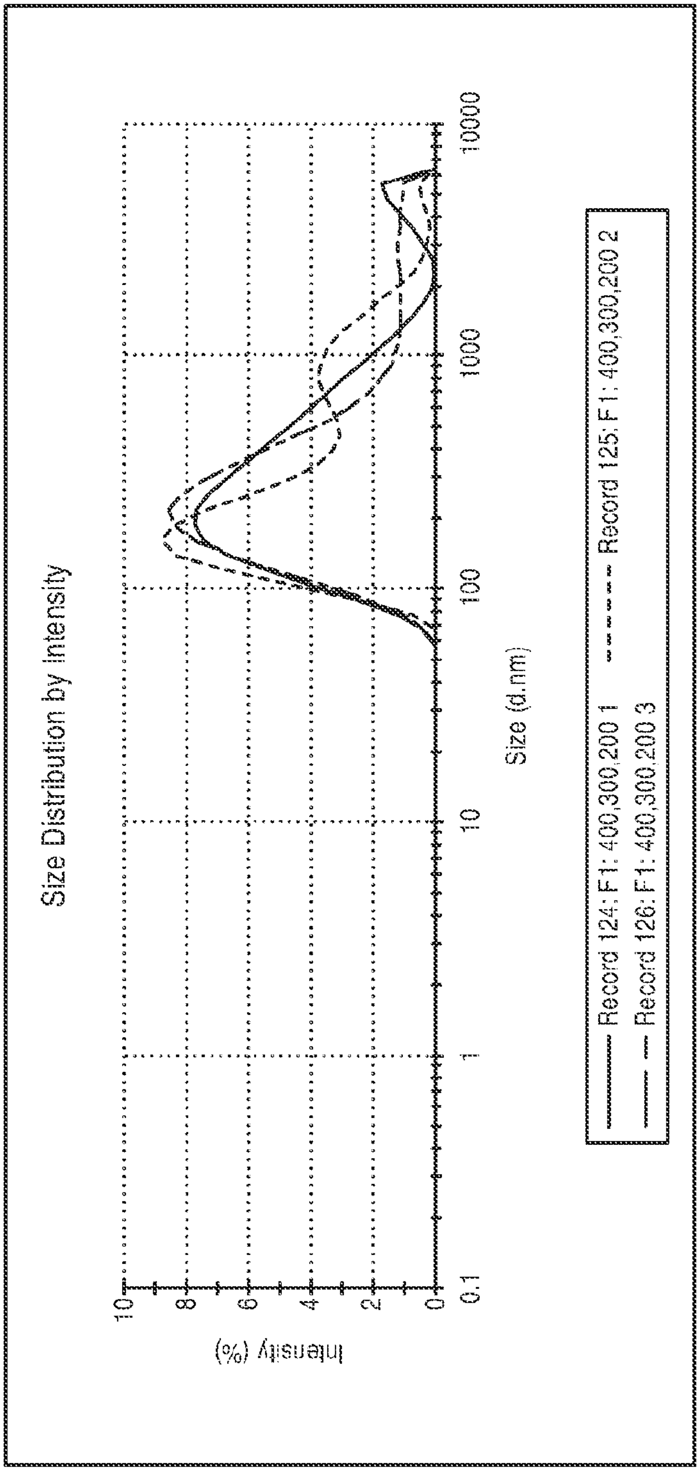
FIG. 7 shows particle size distributions for Composition Nos. 62-65.
Figure 7:
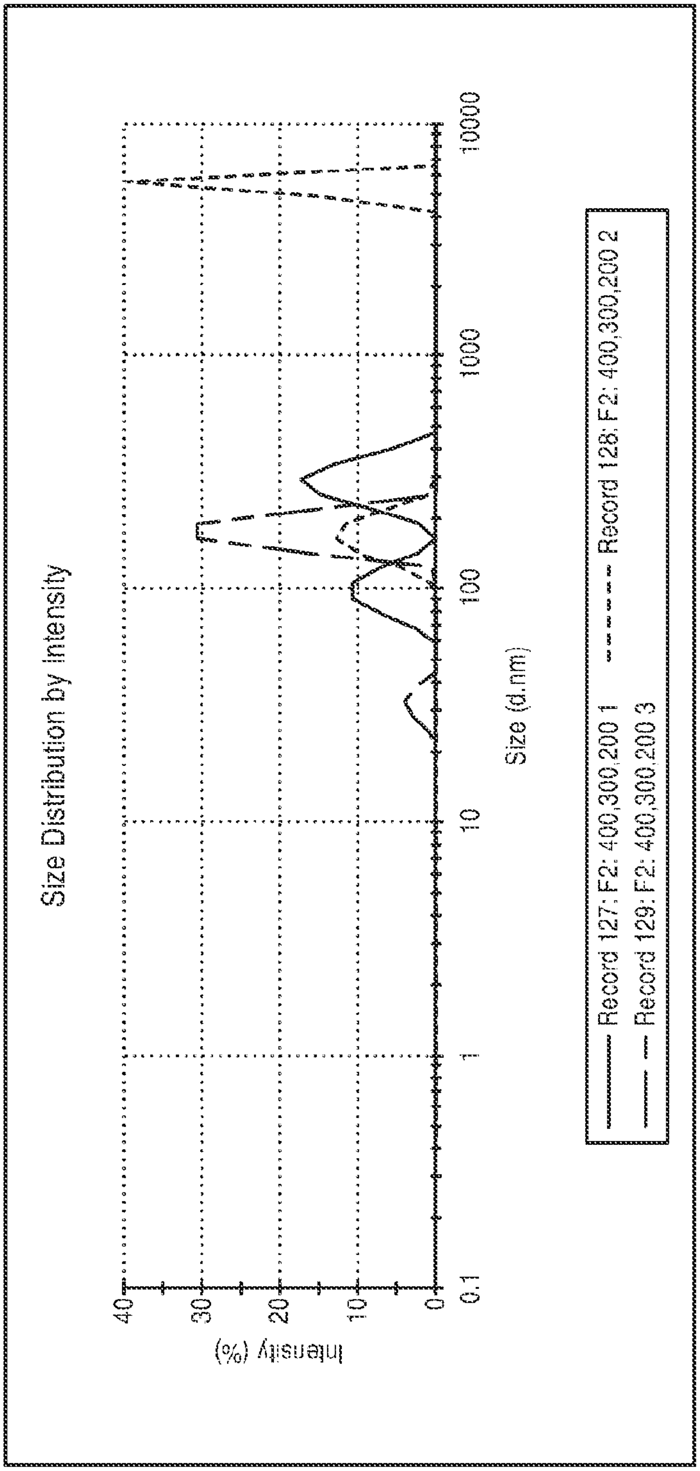
Figure 7:
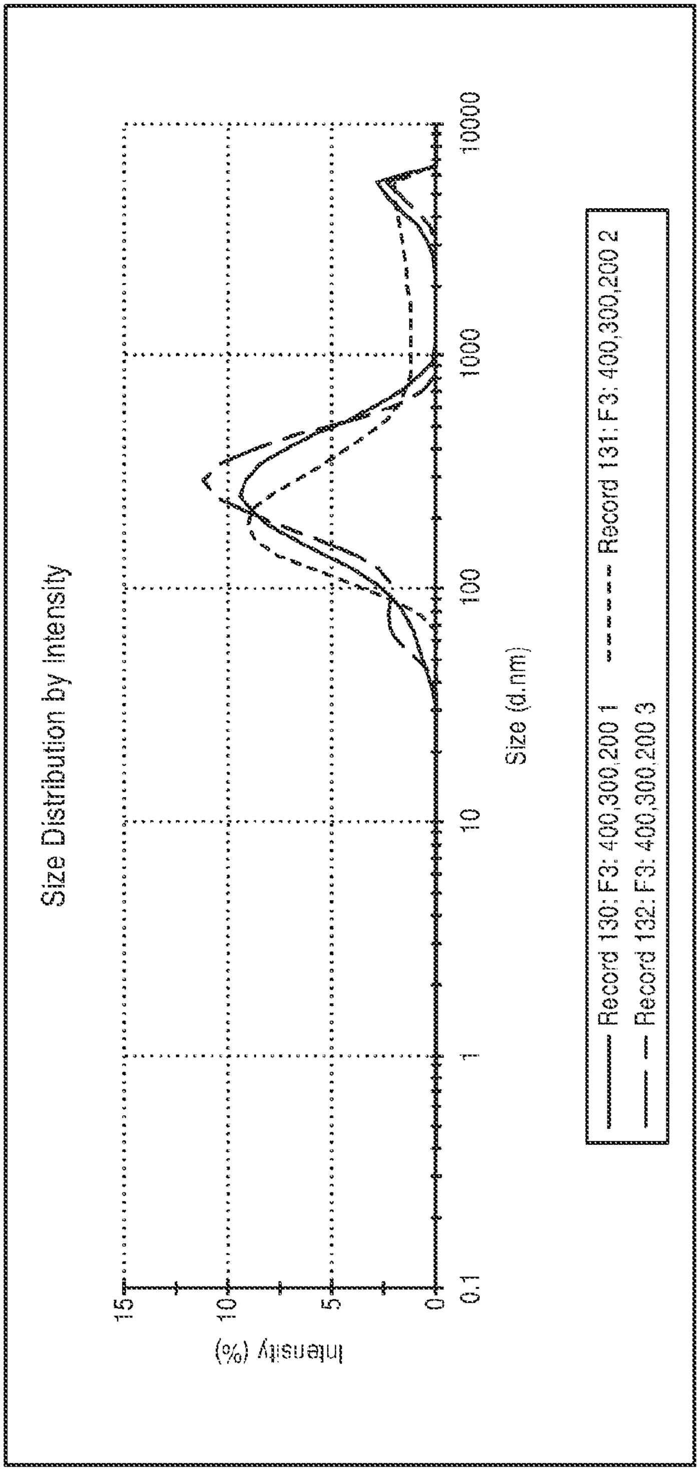
Figure 7:
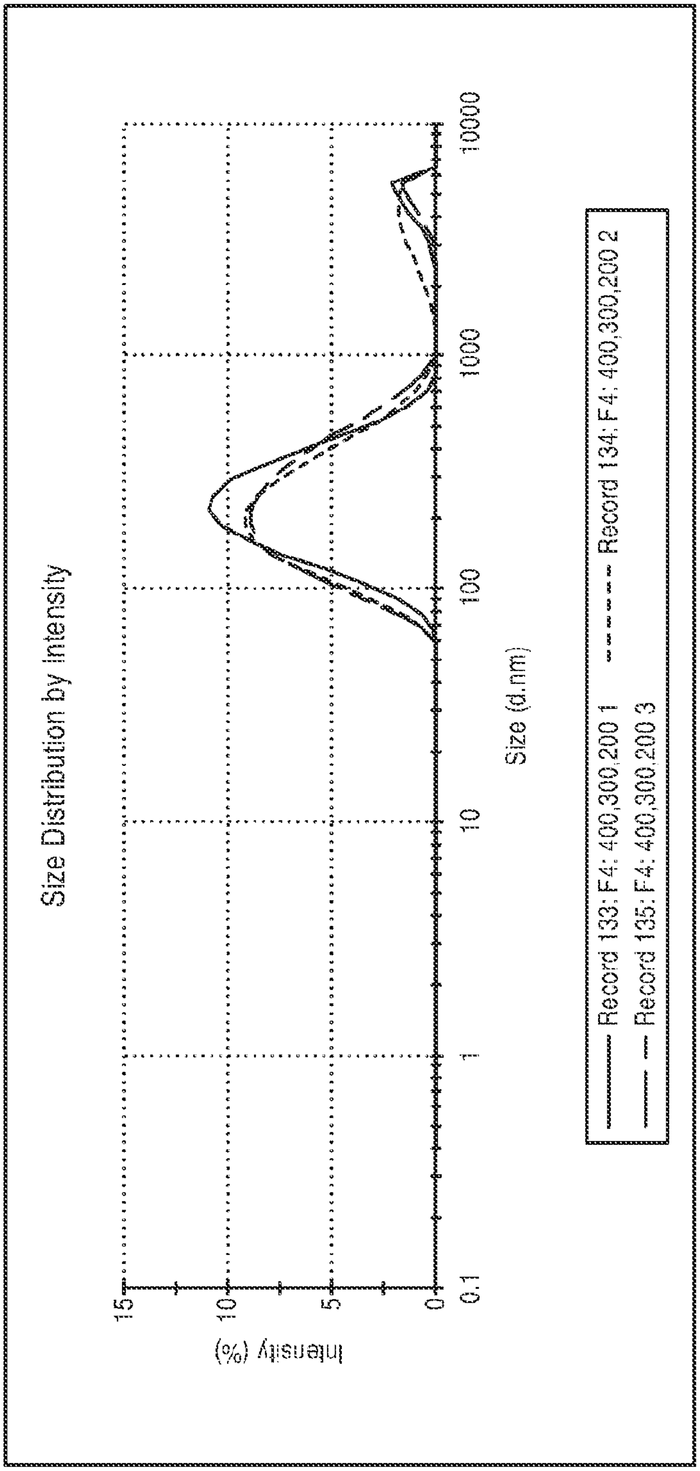

Substitution of various LCT oils for the MCT oil in Composition No. 27 was evaluated. Initial studies indicated that a composition composed of Tween-20/Active ingredient/LCT in a 400/300/200 ratio was the maximum concentration of LCT that could be reached. Increasing the LCT fraction to 235 resulted in non-homogeneous pre-concentrates. Emulsions of Composition Nos. 62-65 were formed using water as the aqueous medium. The composition of the preconcentrates are shown in Table 14 and the particle size distributions for the emulsions formed in water are shown in FIG. 7.

TABLE 14

Substitution of LCT for MCT in Composition 27

| No. | Tween-20 (mg) | Active ingredient (mg) | LCT oil (200 mg) |
|---|---|---|---|
| 62 | 400 | 300 | Sesame oil |
| 63 | 400 | 300 | Castor oil |
| 64 | 400 | 300 | Soybean oil |
| 65 | 400 | 300 | Safflower seed oil |

Example 6: Optimization of Sesame Oil Amount

Figure 8:
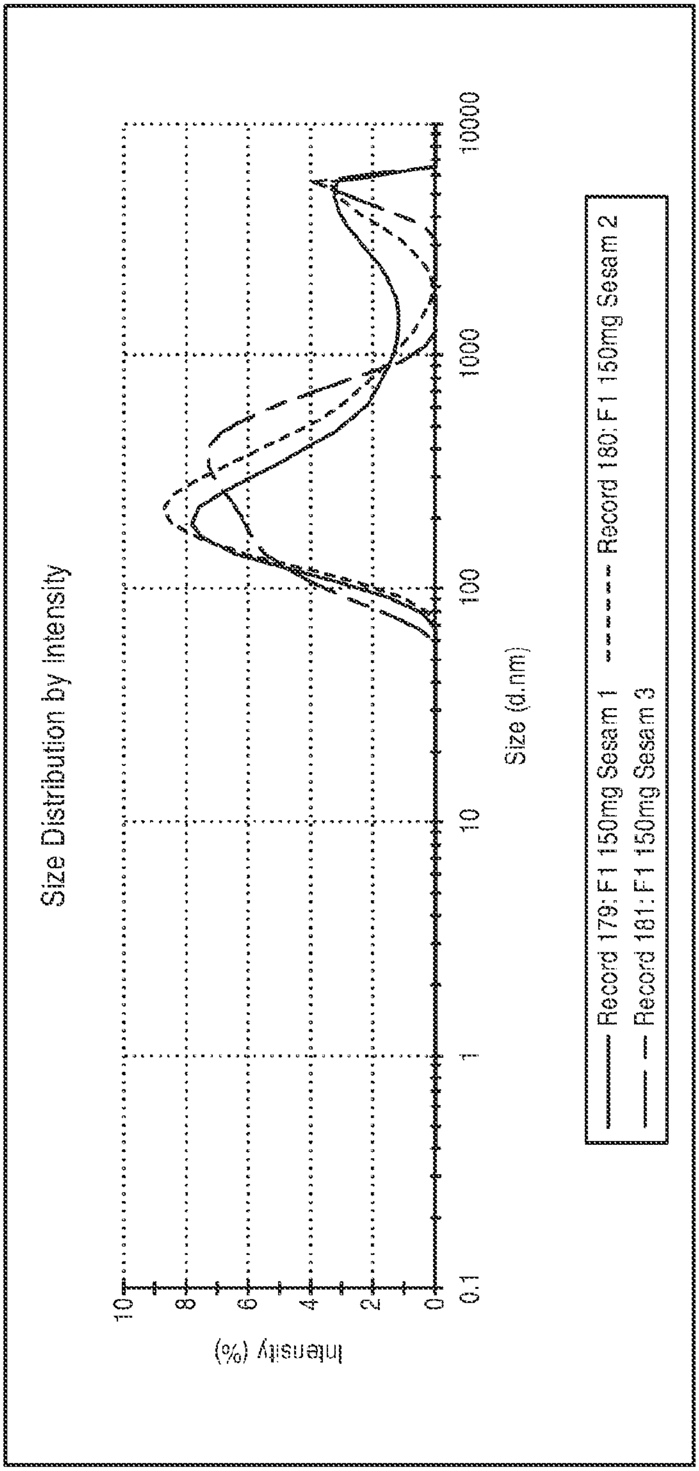
FIG. 8 shows particle size distributions for Composition Nos. 66-72.
Figure 8:
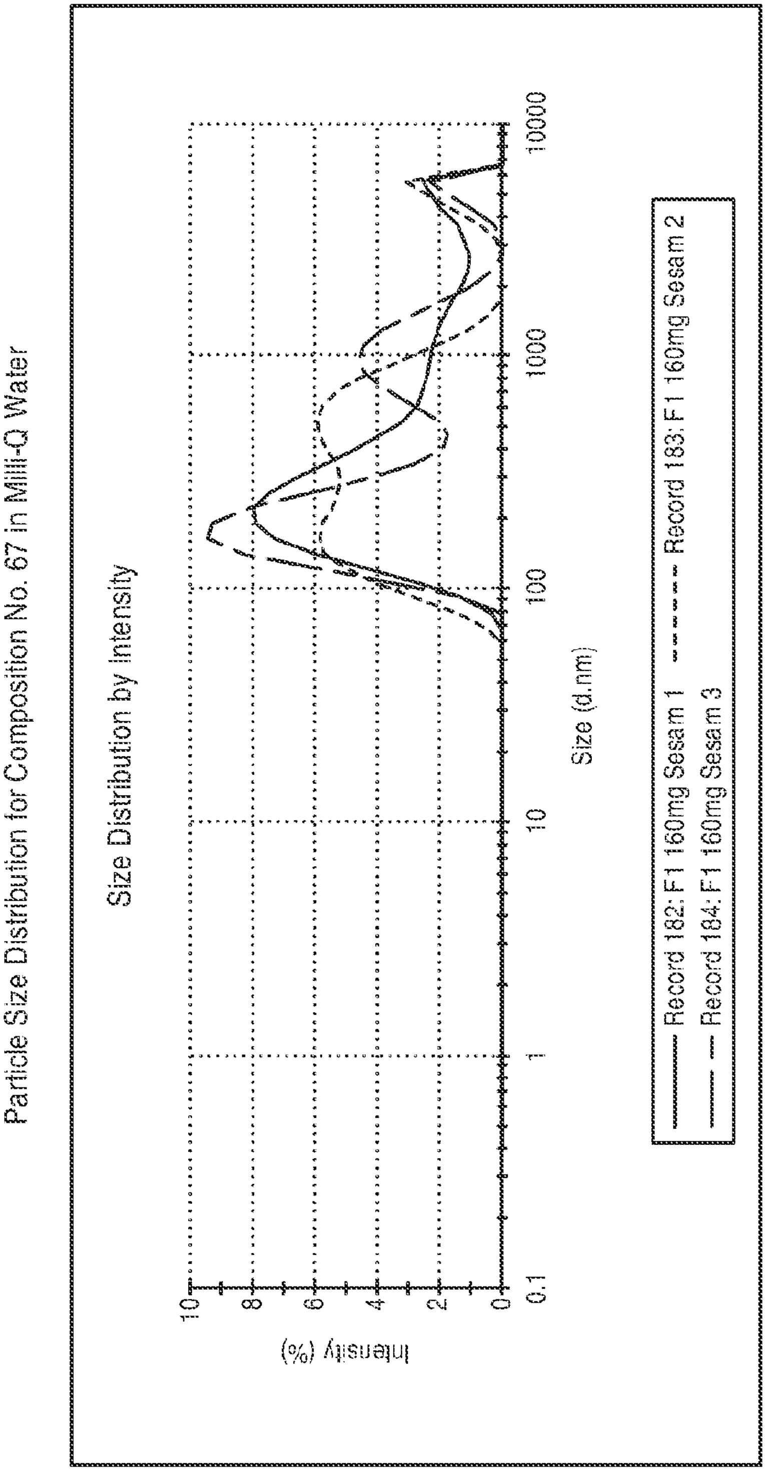
Figure 8:
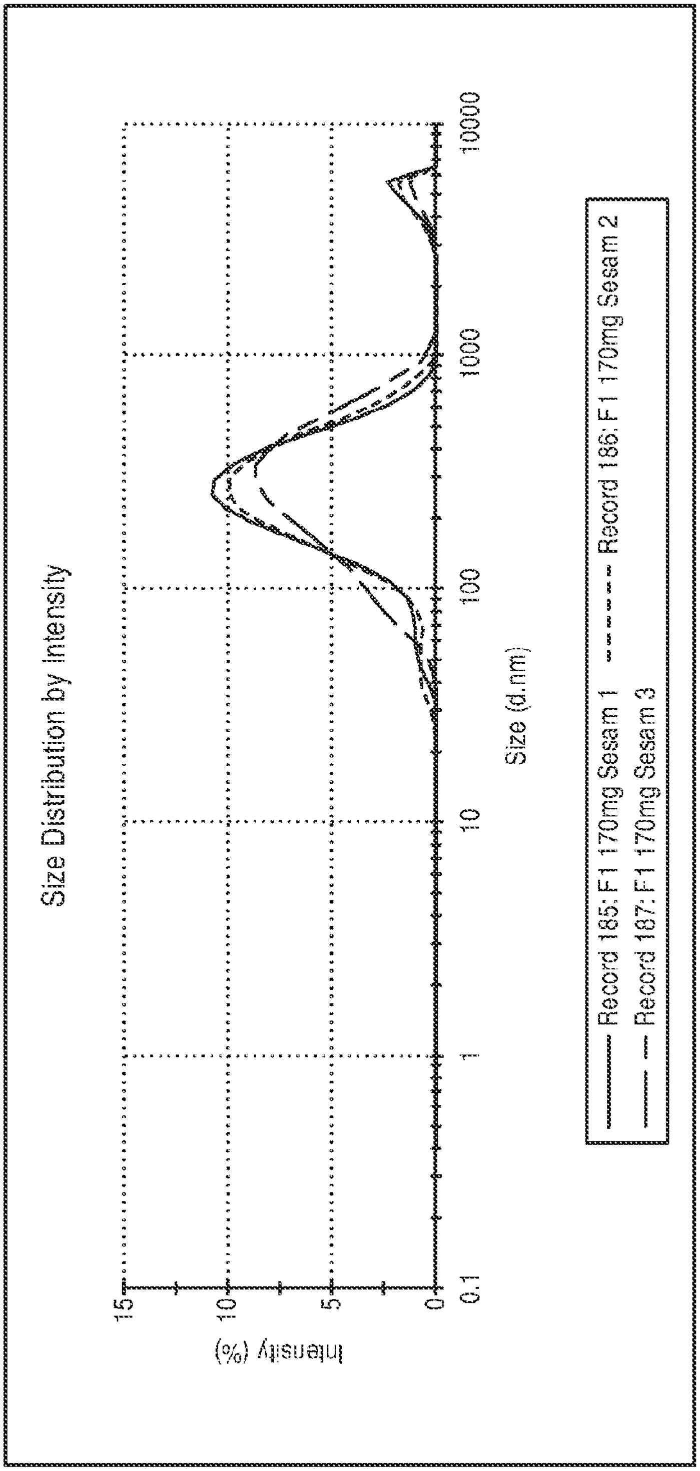
Figure 8:
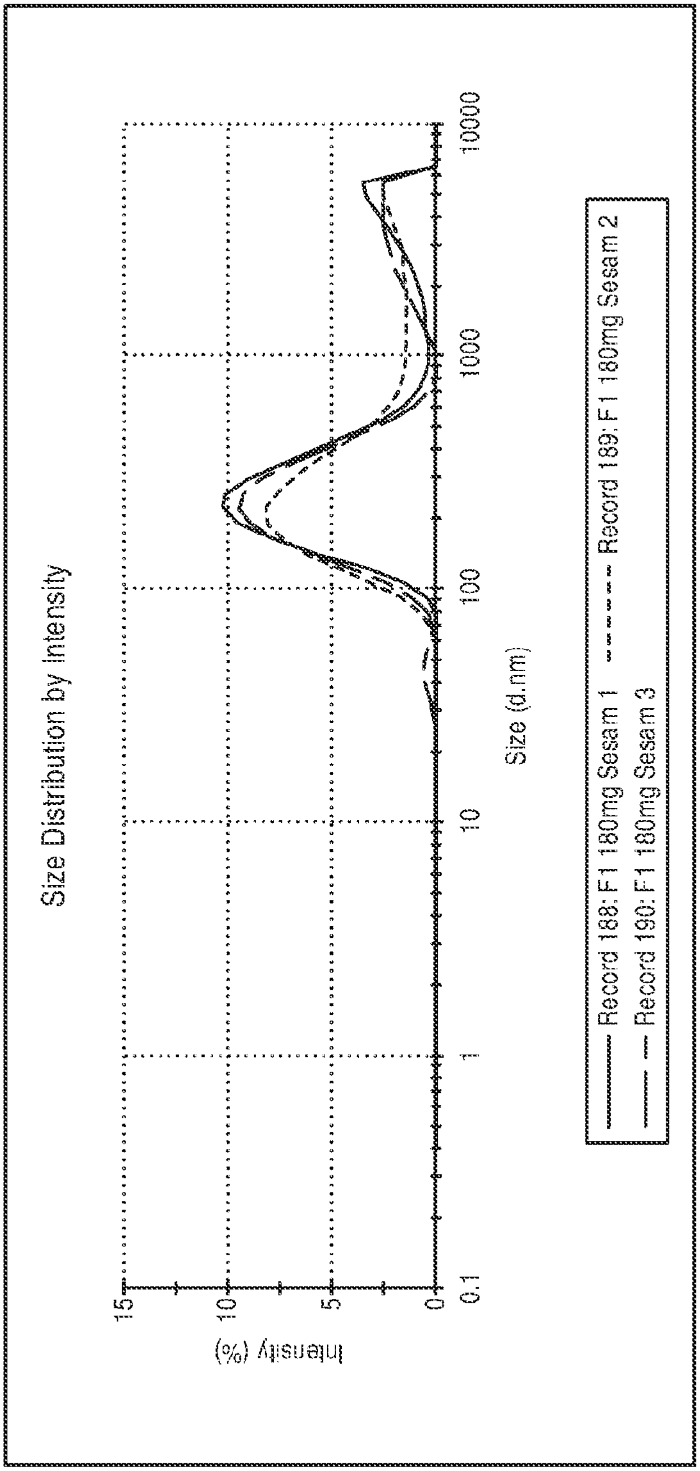
Figure 8:
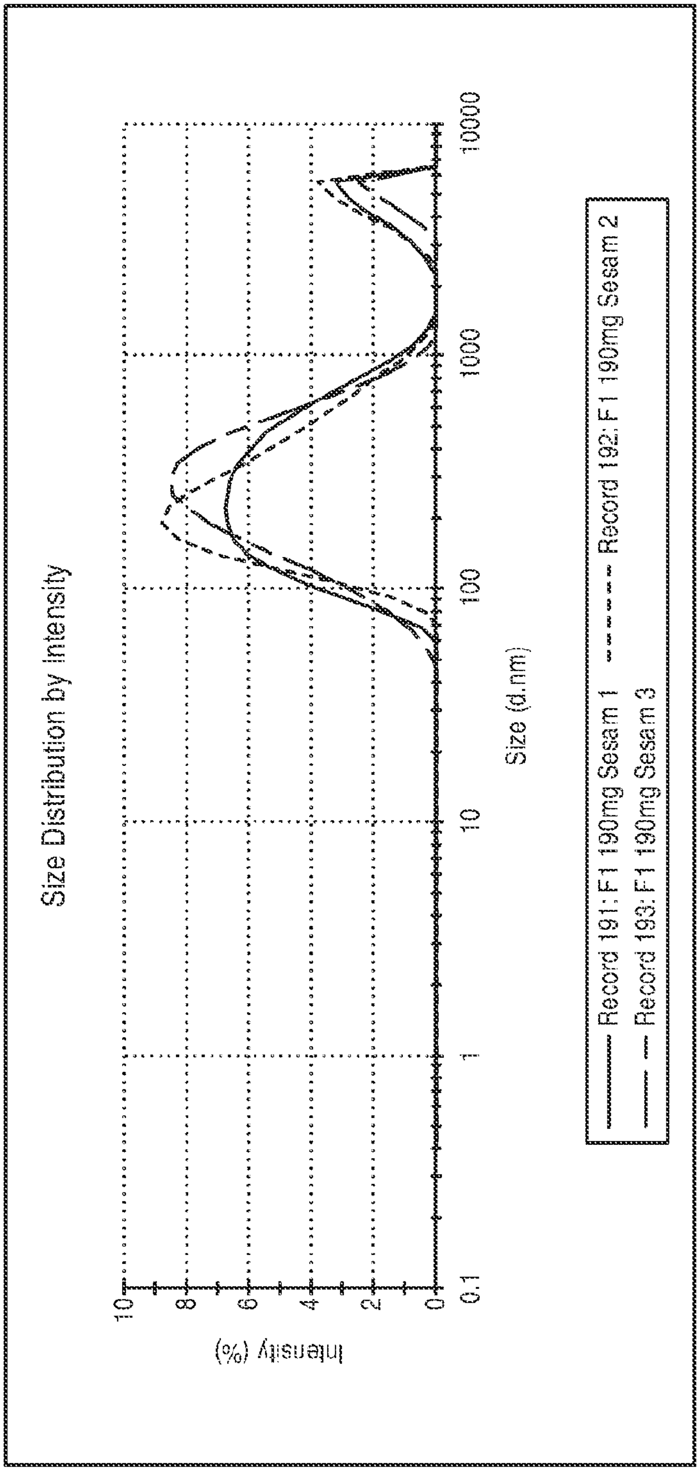
Figure 8:
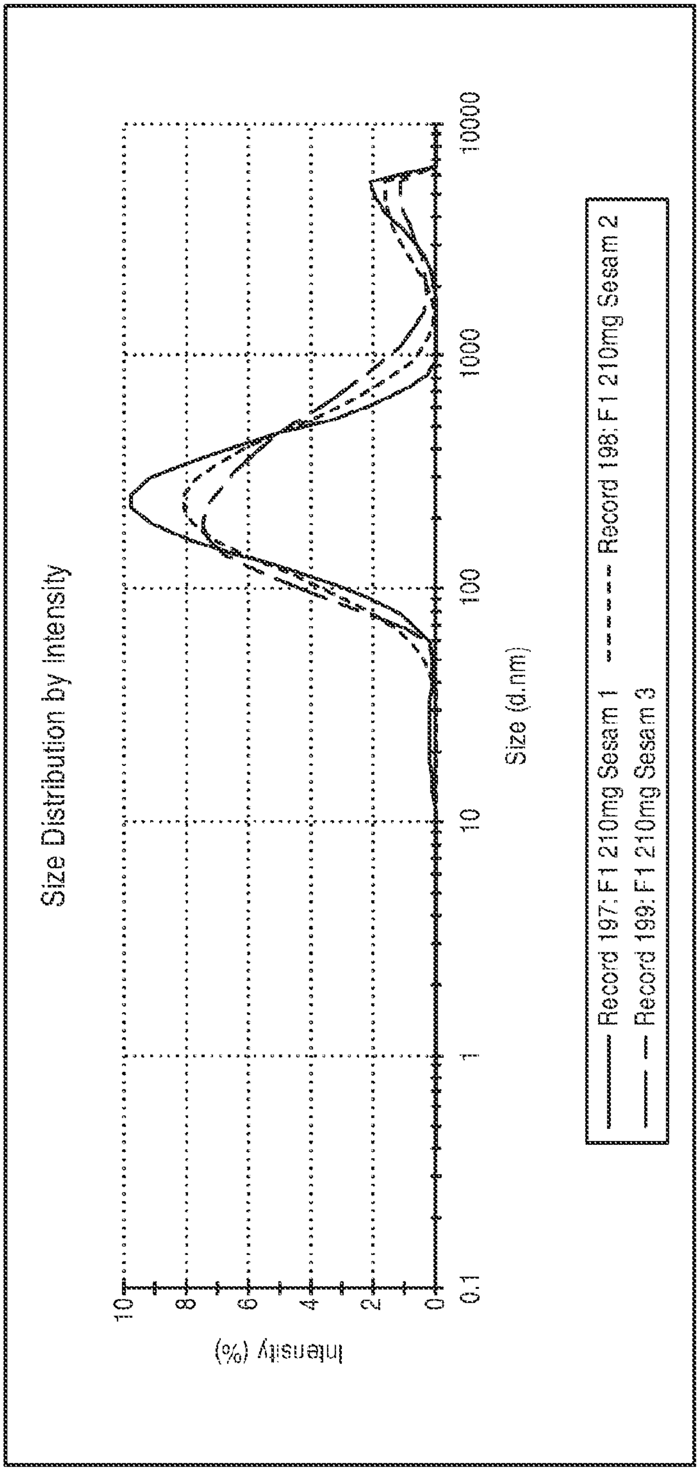
Figure 8:
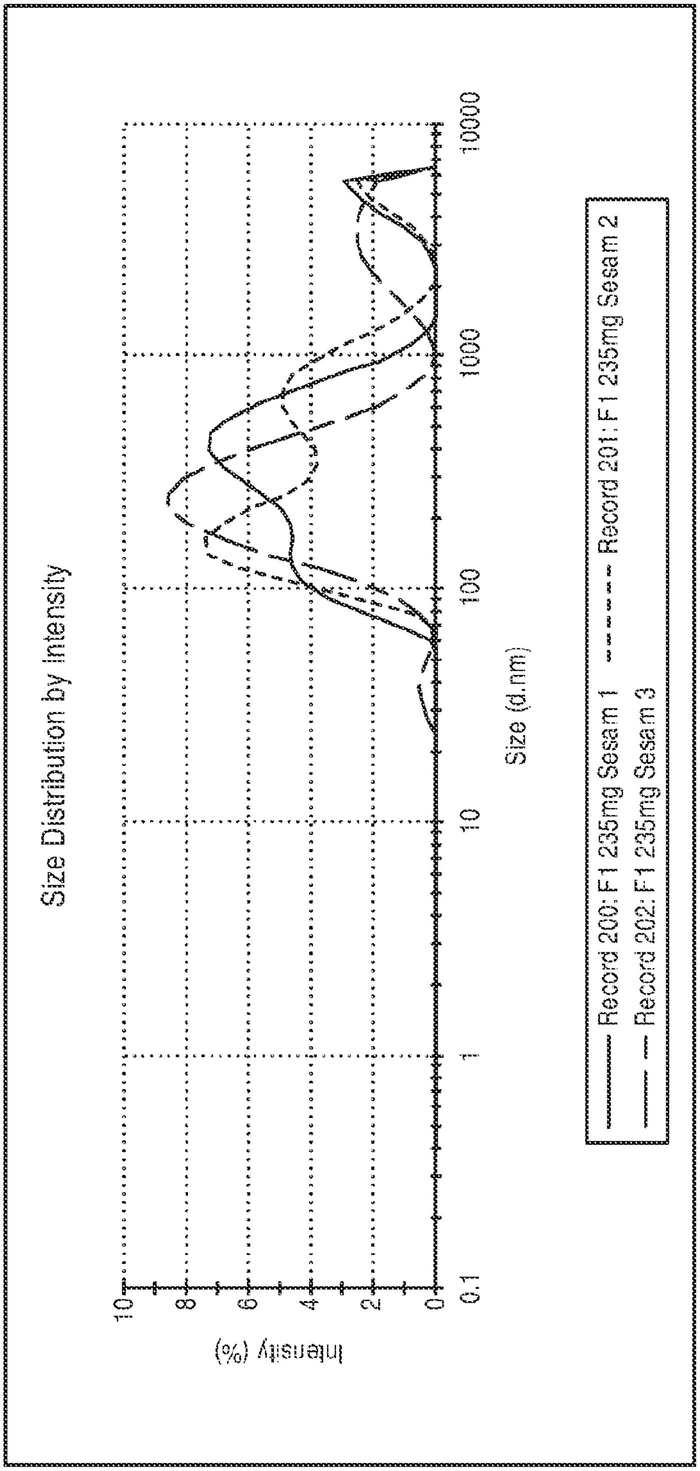

Various amounts of sesame oil were investigated as the LCT oil in the composition. Emulsions of Composition Nos. 66-72 were formed using water as the aqueous medium. The composition of the pre-concentrates is shown in Table 15 and the particle size distributions for the emulsions formed in water are shown in FIG. 8. The optimal composition was Composition No. 89.

TABLE 15

Optimization of Sesame Oil Amount

| No. | Tween-20 (mg) | Active ingredient (mg) | Sesame oil (mg) |
|---|---|---|---|
| 66 | 400 | 300 | 150 |
| 67 | 400 | 300 | 160 |

TABLE 15-continued

| Optimization of Sesame Oil Amount | | | |
|---|---|---|---|
| No. | Tween-20 (mg) | Active ingredient (mg) | Sesame oil (mg) |
| 68 | 400 | 300 | 170 |
| 69 | 400 | 300 | 180 |
| 70 | 400 | 300 | 190 |
| 89 | 400 | 300 | 210 |
| 72 | 400 | 300 | 235 |

Example 7: SMEDDS Prepared from Salts

Salts prepared from monovalent counter ions are all highly soluble in surfactants according to the present disclosure and excellent pre-concentrates and SMEDDS can be prepared. The magnesium salt shows medium solubility in surfactants and co-solvents, and excellent emulsions can be prepared, which are more stable than SMEDDS made with monovalent ions.

Preparation of magnesium 2-((5Z,8Z,11Z,14Z,17Z)-icosa-5,8,11,14,17-pentaenyloxy)butanoate (2-((5Z,8Z,11Z,14Z,17Z)-icosa-5,8,11,14,17-pentaenyloxy)butanoic acid (3.74 g) was mixed with $MgCO_3$ (420 mg, Sigma-Aldrich, Catalog no. M7179). Water (2.0 ml) was added and the mixture was stirred with mechanical stirring at room temperature (RT) overnight. $CO_2$ develops and thick homogeneous pasta is formed. Ethanol (20 ml) was added to the reaction flask under stirring. The magnesium salt formed from (2-((5Z,8Z,11Z,14Z,17Z)-icosa-5,8,11,14,17-pentaenyloxy)butanoic acid goes into solution upon addition of ethanol. The solution was filtered and evaporated to dryness in vacuo. The crude viscous oil was evaporated two times with 96% ethanol to remove traces of water. The oil was stored under nitrogen at room temperature and does not change in color over after storage for several weeks.

Preparation of Compositions

Compositions were prepared by mixing the components shown for each sample in Table 16. The compositions were scored as unclear (separates into phases in short time), cloudy (close to being transparent, and do not separate into phases) and clear (homogenous transparent pre-concentrates). The compositions contained Tween 80, MCT oil (Miglyol 812N) and the magnesium salt of (2-((5Z,8Z,11Z,14Z,17Z)-icosa-5,8,11,14,17-pentaenyloxy)butanoic acid. As shown in Table 16 compositions forming clear preconcentrates are formed comprising about 20-50% by weight of the total composition of API, about 45-60% by weight of the total composition of MCT oil and about 5-25% by weight of the total composition of Tween 80. The best compositions were formed having about 50% by weight of the total composition of MCT oil, about 30% by weight of the total composition of magnesium salt of 2-((5Z,8Z,11Z,14Z,17Z)-icosa-5,8,11,14,17-pentaenyloxy)butanoic acid and about 20% by weight of the total composition of Tween 80.

TABLE 16

Compositions prepared from Tween 80, Miglyol 812N and magnesium (2-((5Z,8Z,11Z,14Z,17Z)-icosa-5,8,11,14,17-pentaenyloxy)butanoate

| Sample No. | Tween 80 (mg) | Mg salt (mg) | MCT oil (mg) | wt % Mg salt | pre-conc. |
|---|---|---|---|---|---|
| 101 | 500 | 1500 | 500 | 60.0 | unclear |
| 102 | 750 | 1500 | 1750 | 37.5 | unclear |
| 103 | 50 | 300 | 50 | 75.0 | unclear |
| 104 | 100 | 300 | 100 | 60.0 | unclear |
| 405 | 300 | 300 | 600 | 25.0 | unclear |
| 106 | 300 | 300 | 700 | 23.1 | cloudy |
| 107 | 300 | 300 | 750 | 22.2 | cloudy |
| 108 | 300 | 300 | 800 | 21.4 | clear |
| 109 | 50 | 300 | 300 | 46.2 | unclear |
| 110 | 50 | 300 | 250 | 50.0 | unclear |
| 111 | 20 | 300 | 100 | 71.4 | unclear |
| 112 | 60 | 300 | 550 | 33.0 | unclear |
| 113 | 80 | 300 | 600 | 30.6 | unclear |
| 114 | 100 | 300 | 600 | 30.0 | unclear |
| 115 | 120 | 300 | 600 | 29.4 | unclear |
| 116 | 140 | 300 | 600 | 28.8 | cloudy |
| 117 | 160 | 300 | 600 | 28.3 | clear |
| 118 | 160 | 300 | 650 | 27.0 | unclear |
| 119 | 160 | 300 | 700 | 25.9 | unclear |
| 120 | 180 | 300 | 700 | 25.4 | unclear |
| 121 | 260 | 300 | 700 | 23.8 | clear |

| No. | Tween 80 | Mg salt | MCT oil | Wt % Mg salt | Wt % Tween 80 | Wt % MCT | pre-conc. |
|---|---|---|---|---|---|---|---|
| 122 | 100 | 400 | 500 | 40.0 | 10.0 | 50.0 | unclear |
| 123 | 120 | 400 | 600 | 35.7 | 10.7 | 53.6 | unclear |
| 124 | 140 | 400 | 800 | 29.9 | 10.4 | 59.7 | cloudy |
| 125 | 140 | 400 | 850 | 28.8 | 10.1 | 61.2 | cloudy |
| 126 | 180 | 350 | 700 | 28.5 | 14.6 | 56.9 | clear |
| 127 | 210 | 350 | 800 | 25.7 | 15.4 | 58.8 | clear |
| 128 | 210 | 350 | 850 | 24.8 | 14.9 | 60.3 | cloudy |
| 129 | 240 | 350 | 1000 | 22.0 | 15.1 | 62.9 | unclear |
| 130 | 240 | 350 | 1050 | 21.3 | 14.6 | 64.0 | unclear |
| 131 | 200 | 300 | 500 | 30.0 | 20.0 | 50.0 | cloudy |
| 132 | 240 | 350 | 600 | 29.4 | 20.2 | 50.4 | cloudy |
| 133 | 240 | 350 | 650 | 28.2 | 19.4 | 52.4 | clear |
| 134 | 280 | 350 | 750 | 25.4 | 20.3 | 54.3 | cloudy |
| 135 | 200 | 300 | 280 | 38.5 | 25.6 | 35.9 | unclear |
| 136 | 200 | 300 | 300 | 37.5 | 25.0 | 37.5 | unclear |
| 137 | 200 | 300 | 350 | 35.3 | 23.5 | 41.2 | unclear |
| 138 | 200 | 300 | 400 | 33.3 | 22.2 | 44.4 | cloudy |
| 139 | 200 | 300 | 450 | 31.6 | 21.1 | 47.4 | clear |

Example 8: Improvement of Portal Vein Uptake

The absorption profile of a formulation including Tween 20 (40 wt %), Miglyol 812N (30 wt %) and 2-((5Z,8Z,11Z,14Z,17Z)-icosa-5,8,11,14,17-pentaenyloxy)butanoic acid (API, 30 wt %) was investigated. The API was mixed with the other components of the composition as described under "General procedures." The formulation used in this example corresponds to composition No. 27 of Example 1. The absorption was studied in groups of 4 male Sprague-Dawley rats following administration of a single oral dose of API at 50 mg/kg/body weight.

Rats were fasted overnight prior to use and are supplemented with 2 ml/rat 0.9% saline 30 min before dosing. The formulation was administered by oral gavage and blood was withdrawn via portal vein catheter and lymph fluid via mesenteric lymph duct. Samples were obtained at indicated time points post administration up to 24 hour. The API concentration in both plasma and lymph were analyzed. Amount absorbed per time unit was determined as AUC times flow, see Table 17.

TABLE 17

| Portal vein and mesenteric lymph absorption after single oral dose of API at 50 mg/kg/BW in SD rat | | | |
|---|---|---|---|
| | API in Tween 20 and Miglyol 812 | | |
| Formulation | $C_{max}$ (μg/mL) | AUC * flow | $T_{max}$ (h) |
| Portal vein | 19 | 715 | 2 |
| Mesenteric lymph | 7.7 | 66 | 4 |

It is concluded that the formulation provided much higher uptake by the portal vein as compared with lymphatic route. Thus, the systemic exposure is reduced and as a result may also reduce possible systemic side effects of the API.

Example 9: Improved Bioavailability

The pharmacokinetic profile of two different formulations (corn oil or Tween 20/Miglyol 812) of 2-((5Z,8Z,11Z,14Z,17Z)-icosa-5,8,11,14,17-pentaenyloxy)butanoic acid (API) was studied in groups of 4 male Gottingen minipigs following administration of a single oral dose at 276 mg/animal (in corn oil) or 309 mg/animal (Tween 20/Miglyol 812 formulation). The formulation according to the present disclosure included Tween 20 (40 wt %), Miglyol 812N (30 wt %) and API (30 wt %). The API was mixed with the other components of the composition as described under "General procedures." The composition in this example corresponds to composition No. 27 of Example 1. Both formulations were administered to the minipigs by oral gavage.

Plasma levels of API increased to reach a maximum between 1 and 3 hours post-dose with both formulations (Table 18). Plasma concentrations then decreased to low or undetectable levels at the last time-point of 36 hours after dosing. The formulation of API in Tween 20 and Miglyol 812 showed a 56% improvement of bioavailability compared to that of API in corn oil.

TABLE 18

| Pharmacokinetic parameters of API after a single oral administration to minipigs | | | | | |
|---|---|---|---|---|---|
| Formulation | Dose (mg/kg) | $C_{max}$ (μg/mL) | Relative $AUC_{0-24h}$ (μg · h/mL) | $T_{max}$ (h) | $t_{1/2}$ (h) |
| API in corn oil | 15.5 | 1.97 | 1 | 2.8 | 10.2 |
| API in Tween 20 and Miglyol 812N | 17.3 | 3.82 | 1.56 | 1.3 | 9.11 |

For the formulation according to the present disclosure the absolute systemic bioavailability was determined to be 32% relative to an intravenous administration whereas total amount of API related material excreted by the urinary route was 60%.

It is concluded that the formulation according to the present disclosure improved both systemic and total bioavailability most probably by improving absorption via the portal vein.

Example 10: Improvement of Food Effect

Phase 1 study of 2-((5Z,8Z,11Z,14Z,17Z)-icosa-5,8,11,14,17-pentaenyloxy)butanoic acid (API) assessing the safety, tolerability, PK, and pharmacodynamics (PD) have been performed in healthy individuals. Each group consisted of 6 healthy subjects. The formulation according to the present disclosure included Tween 20 (40 wt %), Miglyol 812N (30 wt %) and API (30 wt %). The API was mixed with other components of the composition as described under "General procedures." The formulation of this example corresponds to composition No. 27 of Example 1. The premix was filled into capsules and administered orally to humans.

Figure 9:
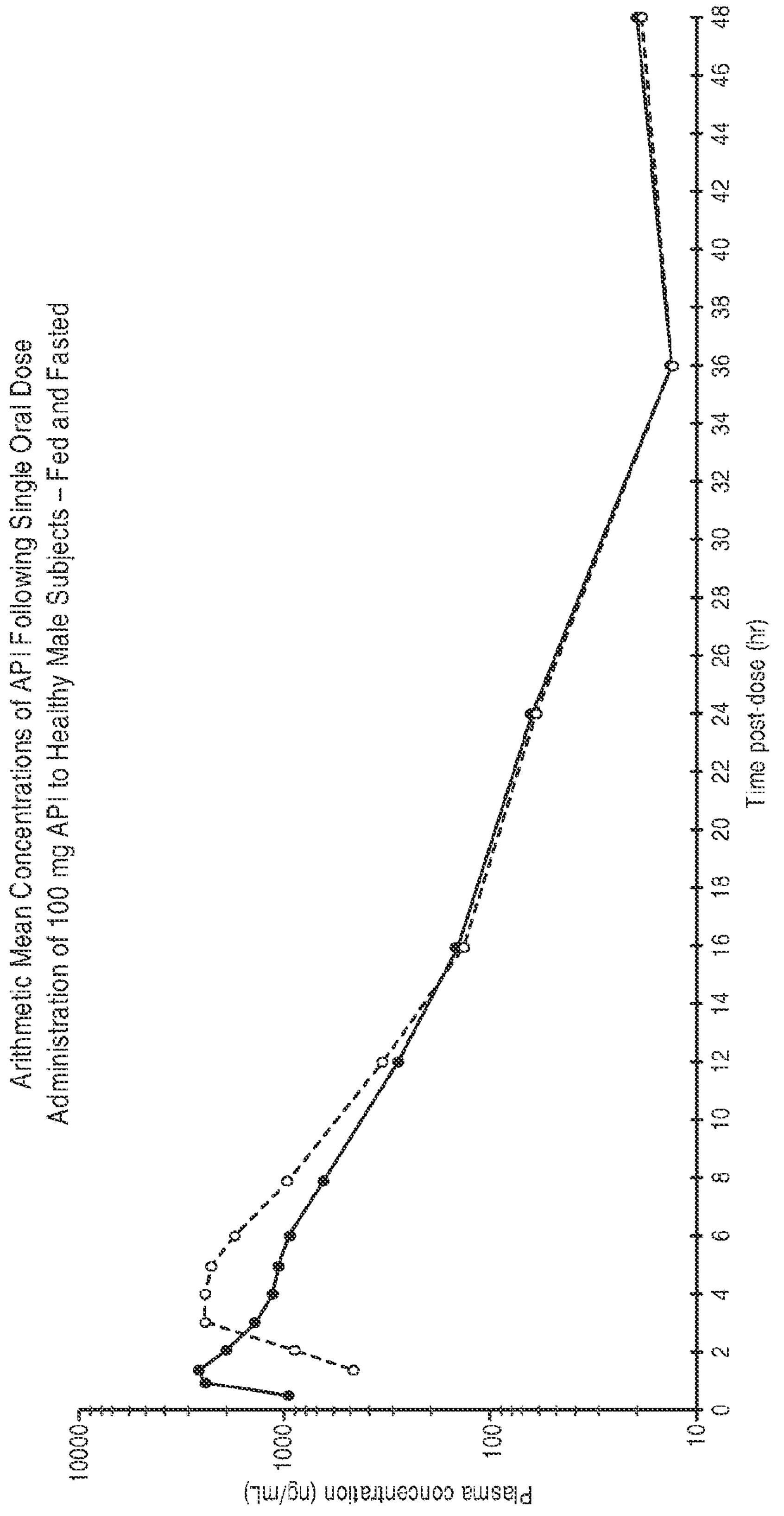
FIG. 9 shows improvement on food effect following administration of formulation according to the present disclosure to healthy male subjects in fed and fasted state.

Data reported demonstrate that the API is rapidly absorbed into the blood stream with mean $T_{max}$ values of approximately 1 to 2 hours in healthy male and female subjects receiving single doses. The food effect study carried out, with a minimum of 10 days intervene before each dose, demonstrated that there is no significant food effect on the bioavailability of the API using the SMEDDS formulation according the present disclosure. $T_{max}$ was delayed by approximately 1.5 hour when the SMEDDS formulation was co-administered with food, see Table 19 and FIG. 9. FIG. 9 shows the arithmetic mean concentrations of API following single oral dose administration of 100 mg of API to healthy male subjects in fed and fasted state.

The API demonstrates both low solubility in water and low permeability. Thus, low bioavailability is expected. Surprisingly it is concluded that the SMEDDS composition according to the present disclosure decreases the food effect on the bioavailability.

TABLE 19

| PK parameters following single oral dose administration of 100 mg API in fasted and fed states | | | | |
|---|---|---|---|---|
| State | AUC0-24 h (μg · h/mL) | $C_{max}$ (ng/mL) | $T_{max}$ (hours) | $t_{1/2}$ (hours) |
| Fed | 15 | 2.7 | 3.6 | 6.29 ± 2.13 |
| Fasted | 14 | 2.8 | 1.4 | 6.36 ± 3.13 |

Example 10: Demonstrating Linear Pharmacokinetics

Phase 1 study of 2-((5Z,8Z,11Z,14Z,17Z)-icosa-5,8,11,14,17-pentaenyloxy)butanoic acid (API) assessing the safety, tolerability, PK, and pharmacodynamics (PD) has been performed in healthy individuals. Each dose group consisted of 6 healthy subjects. The initial dose of API received was 5 mg, and the maximum dose of API was 600 mg. The API was mixed with other components of the formulations according to Table 20, the premix was filled into capsules and administered orally to humans.

TABLE 20

| Composition of API in capsules | | |
|---|---|---|
| Amount API (mg) | Miglyol 812 (wt %) | Tween 20 (wt %) |
| 5 | 42 | 56 |
| 50 | 36 | 49 |
| 100 | 30 | 40 |

Figure 10:
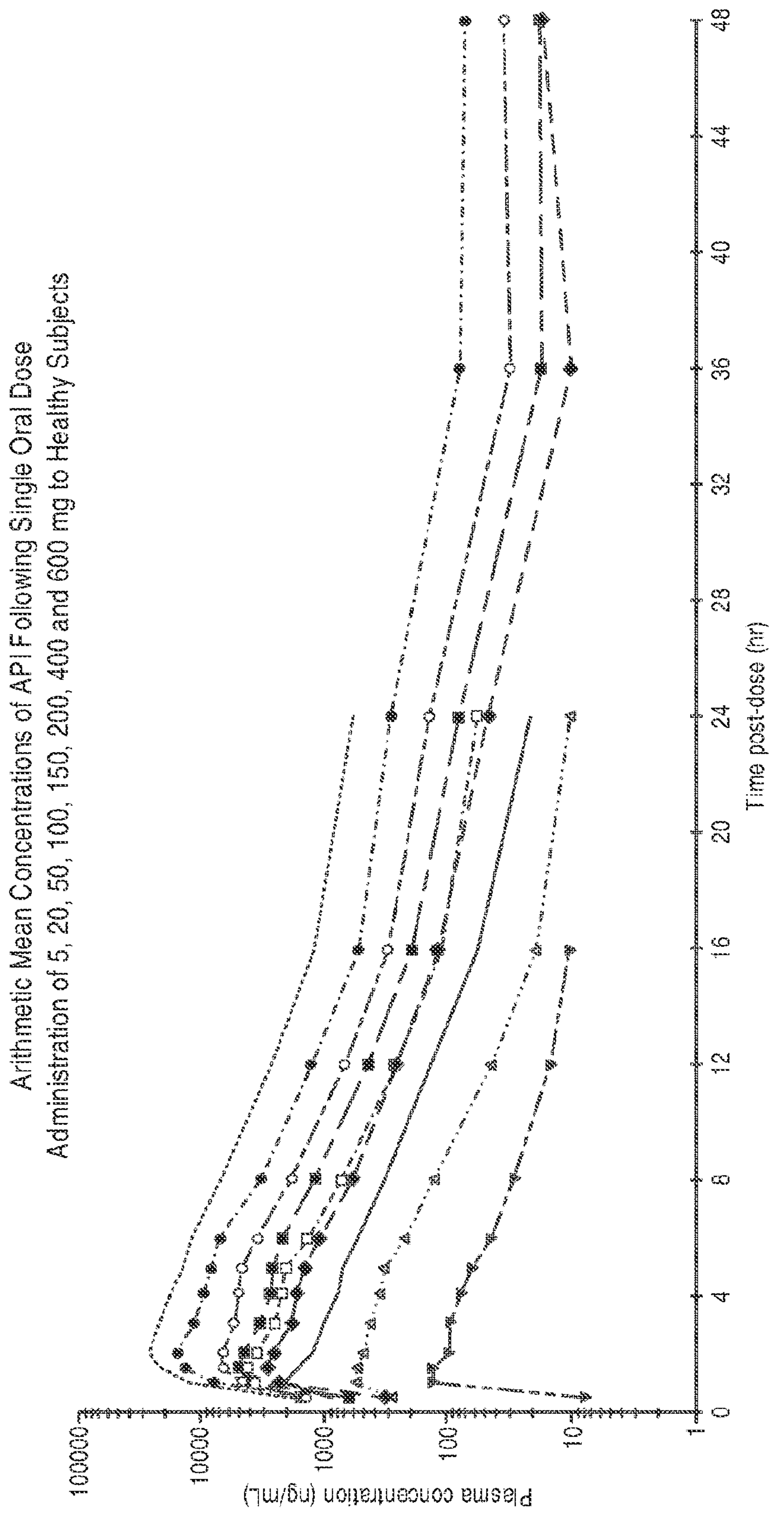
FIG. 10 demonstrates linear pharmacokinetics following administration of formulations according to the present disclosure to healthy subjects.

A minimum of 10 days intervene before each dose escalation. Escalating doses are administered to the groups sequentially. Exposure based on maximum plasma concentration ($C_{max}$) and area under the curve 0 to 24 hours ($AUC_{0-24}$) increased in a higher than dose-proportional manner between 5 to 600 mg. FIG. 10 shows arithmetic mean concentrations of API following single oral dose administration of 5, 20, 50, 100, 150, 200, 400 and 600 mg to healthy subjects.

It is concluded that the SMEDDS formulation according to the present disclosure may provide dose independent linear pharmacokinetics.

Example 11: Demonstrating Low Individual Variability in Pharmacokinetics

Figure 11:
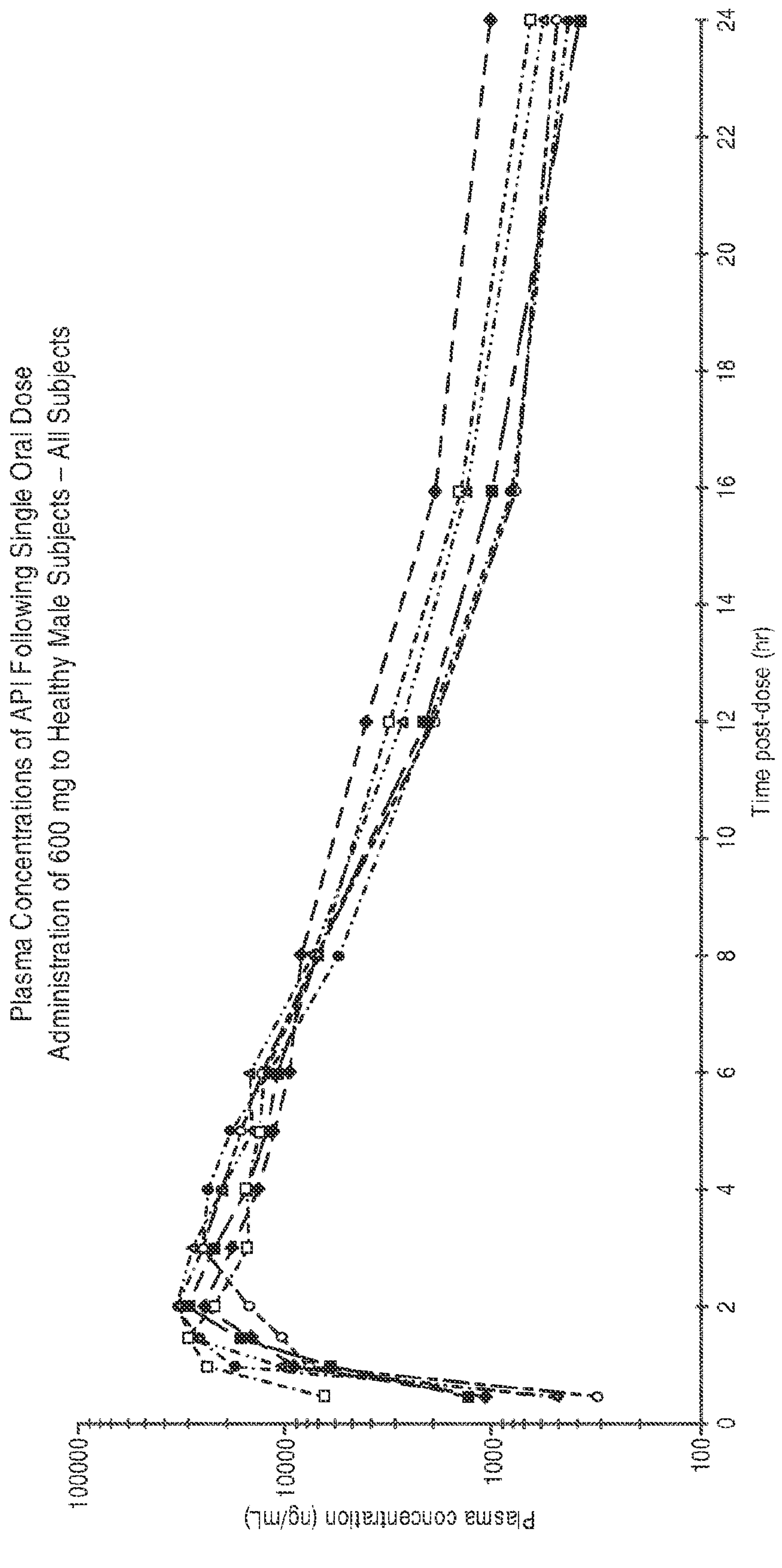
FIG. 11 demonstrates low individual variability in pharmacokinetics following administration of a formulation according to the present disclosure.

Phase 1 study of 2-((5Z,8Z,11Z,14Z,17Z)-icosa-5,8,11,14,17-pentaenyloxy)butanoic acid (API) assessing the safety, tolerability, PK, and pharmacodynamics (PD) has been performed in healthy individuals. Each dose group consisted of 6 healthy subjects. The initial dose API received was 5 mg, and the maximum dose was 600 mg. Data presented here are with an API dose of 600 mg. This formulation included Tween 20 (40 wt %), Miglyol 812N (30 wt %) and API (30 wt %). The API was mixed with other components of the composition as described under "General procedures." The formulation for this example corresponds to composition No. 27 of Example 1. A minimum of 10 days intervene before each dose escalation. Escalating doses were administered to the groups sequentially. Exposure based on maximum plasma concentration ($C_{max}$) and area under the curve 0 to 24 hours ($AUC_{0-24}$) demonstrated unexpectedly low individual variability in pharmacokinetics with a % CV (relative variability) of approximately 10 and 15% respectively. FIG. 11 demonstrates plasma concentrations of API for all subjects following a single oral dose administration of 600 mg to healthy male subjects.

It is concluded that the SMEDDS formulation according to the present disclosure may result in low individual variability in pharmacokinetics.

Example 12: Demonstrating No Gender Differences in Pharmacokinetics

Phase 1 study of 2-((5Z,8Z,11Z,14Z,17Z)-icosa-5,8,11,14,17-pentaenyloxy)butanoic acid (API) assessing the safety, tolerability, PK, and pharmacodynamics (PD) has been performed in healthy individuals. Each dose group consisted of 6 healthy subjects. An API dose of 300 mg b.i.d was given orally to males and females for 14 consecutive days. The formulation given included Tween 20 (40 wt %), Miglyol 812N (30 wt %) and API (30 wt %). The API was mixed with other components in the formulation as described under "General procedures." The formulation of this example corresponds to composition No. 27 of Example 1. Exposure based on maximum plasma concentration ($C_{max}$) and area under the curve 0 to 24 hours ($AUC_{0-24}$) demonstrated the there is no gender differences in pharmacokinetics. Table 21 demonstrates pharmacokinetics in male and female for all subjects following a single oral dose administration of 300 mg b.i.d to healthy subjects.

TABLE 21

Pharmacokinetics in male and female for all subjects following a single oral dose administration of 300 mg b.i.d to healthy subjects.

| | | | Geometric mean | | AUC Ratio | $C_{max}$ Ratio |
|---|---|---|---|---|---|---|
| Treatment | Gender | Day | $AUC_{0-\tau}$ | $C_{max}$ | E/M | E/M |
| 300 mg | Male | 14 | 80900 | 14100 | 0.937 | 1.12 |
| | Female | | 75800 | 15800 | | |

Example 13: Demonstrating Stability of Composition for More than 9 Months

The formulation according to the present disclosure included Tween 20 (40 wt %), Miglyol 812N (30 wt %) and API (30 wt %) and was mixed as described under "General procedures." This formulation corresponds to composition No. 27 of Example 1. The premix was filled into capsules, and the capsules placed in standard condition for stability testing, i.e. 25° C./60% RH. Data presented in Table 22 demonstrate that the total composition in gelatin capsules are stable for more than 9 months.

TABLE 22

Stability data of composition No 27 of Example 1

| | Specification | T0M | T3M | T6M | T9M |
|---|---|---|---|---|---|
| Assay API | 90-110 mg/capsule | Complies | Complies | Complies | Complies |
| BHA | NLT 63 μg/capsule[2] | Complies | Complies | Complies | Complies |
| Related imputities | NMT 0.5 area %[1] | Complies | Complies | Complies | Complies |
| | NMT 30 min (min-max, in min)[1] | Complies | Complies | Complies | Complies |

[1]NMT = not more than
[2]NLT = not less than

Example 14: Compositions with High Wt % of API

Compositions with different amounts of active ingredient (2-((5Z,8Z,11Z,14Z,17Z)-icosa-5,8,11,14,17-pentaenyloxy) butanoic acid), Miglyol 812N as triglycerides, and different types and amounts of surfactants were prepared as shown in Table 23.

TABLE 23

Compositions with high wt % of 2-((5Z,8Z,11Z,14Z,17Z)-icosa-5,8,11,14,17-pentaenyloxy)butanoic acid

| Sample No | API | Miglyol 812 N | Tween 20 | % API | % Miglyol 812 N | % surfactant | pre-conc. |
|---|---|---|---|---|---|---|---|
| 1 | 300 | 300 | 400 | 30.0 | 30.0 | 40.0 | clear |
| 2 | 300 | 250 | 333.0 | 34.0 | 28.3 | 37.7 | clear |
| 3 | 300 | 200 | 266.0 | 39.2 | 26.1 | 34.7 | clear |
| 4 | 300 | 150 | 200.0 | 46.2 | 23.1 | 30.8 | clear |
| 5 | 300 | 100 | 133.0 | 56.3 | 18.8 | 25.0 | clear |
| Sample No | API | Miglyol 812 N | Tween 80 | % API | % Miglyol 812 N | % surfactant | pre-conc. |
| 6 | 300 | 300 | 400 | 30.0 | 30.0 | 40.0 | clear |
| 7 | 300 | 250 | 333.0 | 34.0 | 28.3 | 37.7 | clear |
| 8 | 300 | 200 | 266.0 | 39.2 | 26.1 | 34.7 | clear |
| 9 | 300 | 150 | 200.0 | 46.2 | 23.1 | 30.8 | clear |
| 10 | 300 | 100 | 133.0 | 56.3 | 18.8 | 25.0 | clear |
| Sample No | API | Miglyol 812 N | Tween 40 | % API | % Miglyol 812 N | % surfactant | pre-conc. |
| 11 | 300 | 300 | 400 | 30.0 | 30.0 | 40.0 | clear |
| 12 | 300 | 250 | 333.0 | 34.0 | 28.3 | 37.7 | clear |
| 13 | 300 | 200 | 266.0 | 39.2 | 26.1 | 34.7 | clear |
| 14 | 300 | 150 | 200.0 | 46.2 | 23.1 | 30.8 | clear |
| 15 | 300 | 100 | 133.0 | 56.3 | 18.8 | 25.0 | clear |

TABLE 23-continued

Compositions with high wt % of 2-((5Z,8Z,11Z,14Z,17Z)-icosa-5,8,11,14,17-pentaenyloxy)butanoic acid

| Sample No | API | Miglyol 812 N | Chreomophor EL | % API | % Miglyol 812 N | % surfactant | pre-conc. |
|---|---|---|---|---|---|---|---|
| 16 | 300 | 300 | 400 | 30.0 | 30.0 | 40.0 | clear |
| 17 | 300 | 250 | 333.0 | 34.0 | 28.3 | 37.7 | clear |
| 18 | 300 | 200 | 266.0 | 39.2 | 26.1 | 34.7 | clear |
| 19 | 300 | 150 | 200.0 | 46.2 | 23.1 | 30.8 | clear |
| 20 | 300 | 100 | 133.0 | 56.3 | 18.8 | 25.0 | clear |
| Sample No | API | Miglyol 812 N | Solutol HS15 | % API | % Miglyol 812 N | % surfactant | pre-conc. |
| 21 | 300 | 300 | 400 | 30.0 | 30.0 | 40.0 | clear |
| 22 | 300 | 250 | 333.0 | 34.0 | 28.3 | 37.7 | clear |
| 23 | 300 | 200 | 266.0 | 39.2 | 26.1 | 34.7 | clear |
| 24 | 300 | 150 | 200.0 | 46.2 | 23.1 | 30.8 | clear |
| 25 | 300 | 100 | 133.0 | 56.3 | 18.8 | 25.0 | clear |

What is claimed is:

1. A method for the treatment of a disease or condition chosen from:

a dyslipidemic condition; and/or elevated triglyceride levels, non-HDL cholesterol levels, LDL cholesterol levels, and/or VLDL cholesterol levels; in a subject in need thereof, comprising administering to the subject a pharmaceutically active amount of a composition comprising from 5% to 60% by weight of the total composition of 2-((5Z,8Z,11Z,14Z,17Z)-icosa-5,8,11,14,17-pentaenyloxy)butanoic acid, and ester derivative, or a pharmaceutically acceptable salt thereof;

from 15% to 60% by weight of the total composition of a medium-chain triglyceride (MCT) oil; and from 10% to 60% by weight of the total composition of a nonionic surfactant.

2. The method according to claim 1, wherein the dyslipidemic condition is chosen from hypertriglyceridemia (HTG), dyslipidemia, and mixed dyslipidemia.

3. A method for the treatment of a disease or condition chosen from an inflammatory disease or condition and/or atherosclerosis in a subject in need thereof, comprising administering to the subject a pharmaceutically active amount of a composition comprising from 5% to 60% by weight of the total composition of 2-((5Z,8Z,11Z,14Z,17Z)-icosa-5,8,11,14,17-pentaenyloxy)butanoic acid, and ester derivative, or a pharmaceutically acceptable salt thereof;

from 15% to 60% by weight of the total composition of a medium-chain triglyceride (MCT) oil; and from 10% to 60% by weight of the total composition of a nonionic surfactant.

4. A method for the treatment of a disease or condition chosen from peripheral insulin resistance, a diabetic condition, and/or type 2 diabetes in a subject in need thereof, comprising administering to the subject a pharmaceutically active amount of a composition comprising from 5% to 60% by weight of the total composition of 2-((5Z,8Z,11Z,14Z,17Z)-icosa-5,8,11,14,17-pentaenyloxy)butanoic acid, and ester derivative, or a pharmaceutically acceptable salt thereof;

from 15% to 60% by weight of the total composition of a medium-chain triglyceride (MCT) oil; and from 10% to 60% by weight of the total composition of a nonionic surfactant.

5. The method according to claim 1, wherein the total dose of 2-((5Z,8Z,11Z,14Z,17Z)-icosa-5,8,11,14,17-pentaenyloxy)butanoic acid, an ester derivative, or a pharmaceutically acceptable salt thereof, administered per day as a total dose ranges from about 50 mg to about 800 mg.

6. The method according to claim 3, wherein the total dose of 2-((5Z,8Z,11Z,14Z,17Z)-icosa-5,8,11,14,17-pentaenyloxy)butanoic acid, an ester derivative, or a pharmaceutically acceptable salt thereof, administered per day as a total dose ranges from about 50 mg to about 800 mg.

7. The method according to claim 4, wherein the total dose of 2-((5Z,8Z,11Z,14Z,17Z)-icosa-5,8,11,14,17-pentaenyloxy)butanoic acid, an ester derivative, or a pharmaceutically acceptable salt thereof, administered per day as a total dose ranges from about 50 mg to about 800 mg.

8. The method according to claim 1, wherein the composition is administered once daily.

9. The method according to claim 3, wherein the composition is administered once daily.

10. The method according to claim 4, wherein the composition is administered once daily.

11. The method according to claim 1, wherein the medium chain triglyceride oil consists essentially of $C_8$-$C_{10}$ triglycerides.

12. The method according to claim 1, wherein the medium chain triglyceride oil is derived from capric acid and caprylic acid.

13. The method according to claim 3, wherein the medium chain triglyceride oil consists essentially of $C_8$-$C_{10}$ triglycerides.

14. The method according to claim 3, wherein the medium chain triglyceride oil is derived from capric acid and caprylic acid.

15. The method according to claim 4, wherein the medium chain triglyceride oil consists essentially of $C_8$-$C_{10}$ triglycerides.

16. The method according to claim 4, wherein the medium chain triglyceride oil is derived from capric acid and caprylic acid.

17. The method according to claim 1, wherein the nonionic surfactant is chosen from polyoxyethylene (20) sorbitan monooleate with an HLB value of 15.0 (TWEEN 80) and polyoxyethylene (20) sorbitan monolaurate with an HLB value of 16.0 (TWEEN 20).

18. The method according to claim 3, wherein the nonionic surfactant is chosen from polyoxyethylene (20) sorbitan monooleate with an HLB value of 15.0 (TWEEN 80) and polyoxyethylene (20) sorbitan monolaurate with an HLB value of 16.0 (TWEEN 20).

19. The method according to claim 4, wherein the nonionic surfactant is chosen from polyoxyethylene (20) sorbitan monooleate with an HLB value of 15.0 (TWEEN 80) and polyoxyethylene (20) sorbitan monolaurate with an HLB value of 16.0 (TWEEN 20).

20. The method according to claim 2, wherein the wherein the medium chain triglyceride oil is derived from capric acid and caprylic acid and the nonionic surfactant is chosen from polyoxyethylene (20) sorbitan monooleate with an HLB value of 15.0 (TWEEN 80) and polyoxyethylene (20) sorbitan monolaurate with an HLB value of 16.0 (TWEEN 20).

* * * * *